(12) United States Patent
Oshiyama et al.

(10) Patent No.: US 8,178,214 B2
(45) Date of Patent: May 15, 2012

(54) MATERIAL FOR ORGANIC ELECTROLUMINESCENCE ELEMENT, ORGANIC ELECTROLUMINESCENCE ELEMENT, DISPLAY DEVICE AND ILLUMINATION DEVICE

(75) Inventors: Tomohiro Oshiyama, Hachioji (JP); Hiroshi Kita, Hachioji (JP); Yoshio Inoue, Sendai (JP); Shuichi Oi, Sendai (JP)

(73) Assignee: Konica Minolta Holdings, Inc., Tokyo (JP)

( * ) Notice: Subject to any disclaimer, the term of this patent is extended or adjusted under 35 U.S.C. 154(b) by 1572 days.

(21) Appl. No.: 10/590,158

(22) PCT Filed: Feb. 16, 2005

(86) PCT No.: PCT/JP2005/002317
§ 371 (c)(1),
(2), (4) Date: Aug. 21, 2006

(87) PCT Pub. No.: WO2005/083033
PCT Pub. Date: Sep. 9, 2005

(65) Prior Publication Data
US 2007/0184301 A1  Aug. 9, 2007

(30) Foreign Application Priority Data

Feb. 26, 2004  (JP) ................. 2004-051538

(51) Int. Cl.
*H01L 51/54* (2006.01)
*C09K 11/06* (2006.01)

(52) U.S. Cl. ........ 428/690; 428/917; 313/504; 313/506; 252/301.16; 257/40; 257/102; 257/E51.044; 546/4; 546/10

(58) Field of Classification Search ............ 257/E51.044
See application file for complete search history.

(56) References Cited

U.S. PATENT DOCUMENTS

| 2002/0086180 A1* | 7/2002 | Seo et al. .................... 428/690 |
| 2003/0054198 A1* | 3/2003 | Tsuboyama et al. .......... 428/690 |
| 2003/0059646 A1* | 3/2003 | Kamatani et al. ............ 428/690 |
| 2003/0068535 A1* | 4/2003 | Takiguchi et al. ............ 428/704 |
| 2003/0091861 A1* | 5/2003 | Okada et al. ................. 428/690 |
| 2003/0218418 A9* | 11/2003 | Sato et al. .................... 313/504 |
| 2004/0058194 A1* | 3/2004 | Stossel et al. ................ 428/690 |
| 2004/0086743 A1* | 5/2004 | Brown et al. ................. 428/690 |
| 2004/0086745 A1* | 5/2004 | Iwakuma et al. ............. 428/690 |
| 2005/0147843 A1* | 7/2005 | Kobayashi et al. ........... 428/690 |

FOREIGN PATENT DOCUMENTS

| JP | 8-88083 | 4/1996 |
| JP | 2001-160488 | 6/2001 |
| JP | 2003-73665 | 3/2003 |
| JP | 2003/109758 A | * 4/2003 |
| JP | 2003/342284 A | * 12/2003 |
| JP | 2004-281296 | 10/2004 |
| WO | WO 03/084973 A1 | * 10/2003 |

OTHER PUBLICATIONS

Machine translation of JP 2003/342284 A.*
Machine translation of JP 2003/109758 A.*

* cited by examiner

*Primary Examiner* — Jennifer Chriss
*Assistant Examiner* — Michael H Wilson
(74) *Attorney, Agent, or Firm* — Holtz, Holtz, Goodman & Chick, PC

(57) ABSTRACT

A material for an organic electroluminescence element, characterized in that it comprises a platinum complex formed from a platinum ion and a ligand having at least one aryl group being not capable of free rotation or at least one aromatic heterocyclic group being not capable of free rotation; a display device, characterized in that it comprises said material for an organic electroluminescence element and exhibits high luminous efficiency and long luminous life; and an illumination device, characterized in that it comprises said material for an organic electroluminescence element and exhibits high luminous efficiency and long luminous life.

14 Claims, 3 Drawing Sheets

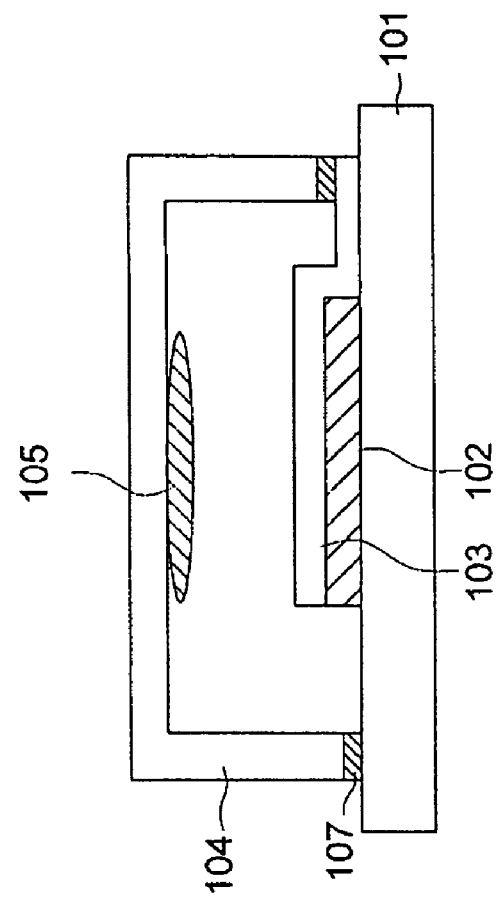
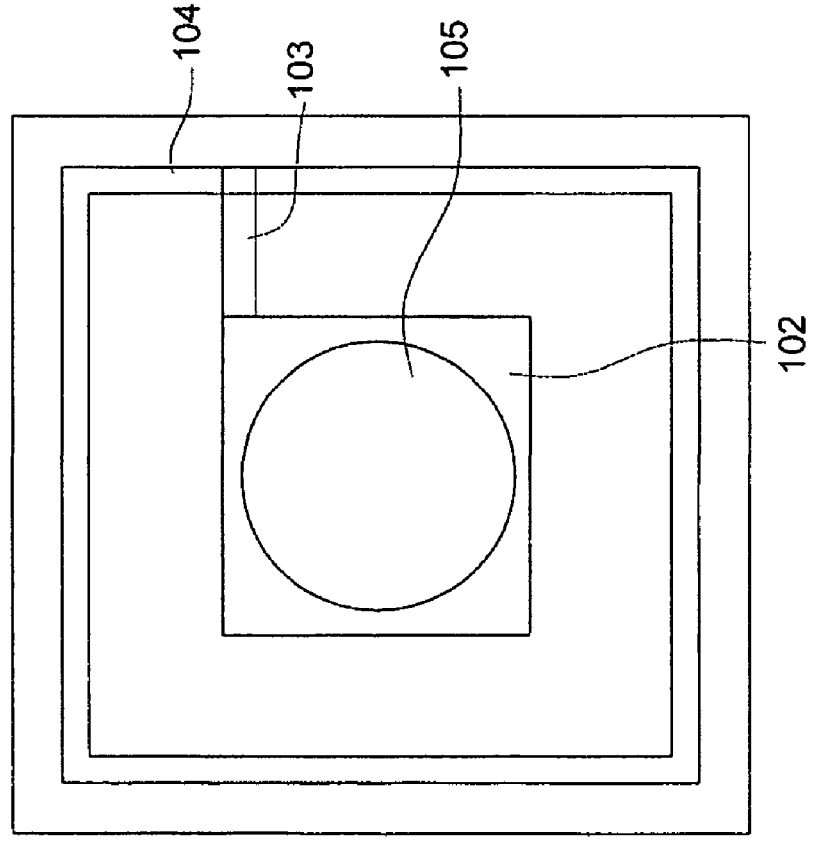
FIG. 6 (a)
FIG. 6 (b)

MATERIAL FOR ORGANIC ELECTROLUMINESCENCE ELEMENT, ORGANIC ELECTROLUMINESCENCE ELEMENT, DISPLAY DEVICE AND ILLUMINATION DEVICE

This application is the United States national phase application of International Application PCT/JP2004/002317 filed Feb. 16, 2005.

TECHNICAL FIELD

The present invention relates to a material for an organic electroluminescence element, an organic electroluminescence element, a display device and an illumination device.

BACKGROUND

As an emission type electronic displaying device, an electroluminescence device (hereinafter, referred to as ELD) is known. Elements constituting the ELD include an inorganic electroluminescence element and an organic electroluminescence element (hereinafter referred to also as an organic EL element). Inorganic electroluminescence element has been used for a plane light source, however, a high voltage alternating current has been required to drive the element. An organic EL element has a structure in which a emission layer containing a light emitting compound is arranged between a cathode and an anode, and an electron and a hole were injected into the emission layer and recombined to form an exciton. The element emits light, utilizing light (fluorescent light or phosphorescent light) generated by inactivation of the exciton, and the element can emit light by applying a relatively low voltage of several volts to several tens of volts. The element has a wide viewing angle and a high visuality since the element is of self light emission type. Further, the element is a thin, complete solid element, and therefore, the element is noted from the viewpoint of space saving and portability.

A practical organic EL element to be used in the future is required to emit light of high luminance with a high efficiency at a lower power.

For example, in Japanese Patent No. 3093796, disclosed is an organic EL element exhibiting higher luminance of emitting light with a longer life in which a stilbene derivative, a distyrylarylene derivative or a tristyrylarylene derivative doped with a slight amount of a fluorescent compound is employed.

In Japanese Patent Publication Open to Public Inspection (hereafter referred to as JP-A) No. 63-264692, disclosed is an element which has an organic emission layer containing 8-hydroxyquinoline aluminum complex as a host compound doped with a slight amount of a fluorescent compound. In JP-A No. 3-255190, disclosed is an element which has an organic emission layer containing 8-hydroxyquinoline aluminum complex as a host compound doped with a quinacridone type dye.

When light emitted through excited singlet state is used in the element disclosed in the above Patent documents, the upper limit of the external quantum efficiency ($\eta$ext) is considered to be at most 5%, because the generation probability of excited species capable of emitting light is 25%, since the generation ratio of singlet excited species to triplet excited species is 1:3, and further, external light emission efficiency is 20%.

Since an organic EL element, employing phosphorescence through the excited triplet, was reported by Prinston University (see M. A. Baldo et al., nature, 395, 151-154(1998)), studies on materials emitting phosphorescence at room temperature have been actively carried.

Such an examples include those reported in M. A. Baldo et al., nature, 403(17), 750-753(2000) and disclosed in U.S. Pat. No. 6,097,147.

As the upper limit of the internal quantum efficiency of the excited triplet is 100%, the light emission efficiency of the exited triplet is theoretically four times that of the excited singlet. Accordingly, light emission employing the excited triplet exhibits almost the same performance as a cold cathode tube, and can be applied to an illumination device.

For example, many kinds of heavy metal complexes such as iridium complexes have been synthesized and studied, for example reported in S. Lamansky et al., J. Am. Chem. Soc., 123, 4304 (2001).

An example employing tris(2-phenylpyridine)iridium as a dopant has been studied in the abovementioned M. A. Baldo et al., nature, 403(17), 750-753(2000).

As other examples, M. E. Tompson et al. have reported, in The 10th International Workshop on Inorganic and Organic Electroluminescence (EL '00, Hamamatsu), a dopant L2Ir (acac) such as (ppy)2Ir(acac), and Moon-Jae Youn.0g, Tetsuo Tsutsui et al., have reported results of an examination using, for example, tris(2-(p-tolyl)pyridine)iridium ($Ir(ptpy)_3$) or tris(benzo[h]quinoline)iridium (Ir(bzq)3) as a dopant, also in The 10th International Workshop on Inorganic and Organic Electroluminescence (EL '00, Hamamatsu).

An example of preparing an element using varieties of iridium complexes has also been reported in abovementioned S. Lamansky et al., J. Am. Chem. Soc., 123, 4304 (2001).

A hole transport material has been used as a host of a phosphorescent compound in order to increase emission efficiency as has been reported by Ikai et al. in The 10th International Workshop on Inorganic and Organic Electroluminescence (EL '00, Hamamatsu). M. E. Thompson et al. have used varieties of electron transport materials as a host material of a phosphorescent compound and have doped a novel iridium complex into the host materials.

An ortho-metalated complex having platinum as a center metal instead of iridium has also attracted attention. Many examples of such complexes having a characteristic ligand have been known (for example, refer to Patent Documents 1-5 and Non-Patent Document 1).

In each case, the luminance and the emission efficiency have been notably improved since the emission is originated from a phosphorescent emission. However, there have been a problem that the emission life has been shorter.

On the other hand, an example has been known in which an emission of white light is obtained by using coexisting monomer emission and excimer emission (refer to Non-Patent Document 2).

However, there has been a problem in the above example that the emission life has been shorter than an organic EL element in which emission of white light is obtained by using a plurality of emission dopants, since the life of an excimer emission has not been long. In addition to that, the emission efficiency of the excimer emission has been below the practical level.

| | |
|---|---|
| Patent documents 1 | JP-A No. 2002-332291 |
| Patent documents 2 | JP-A No. 2002-332292 |
| Patent documents 3 | JP-A No. 2002-338588 |
| Patent documents 4 | JP-A No. 2002-226495 |
| Patent documents 5 | JP-A No. 2002-234894 |
| Nonpatent literature 1 | Inorganic Chemistry, 41(12), 3055-3066 (2002) |
| Nonpatent literature 2 | Advanced Materials., 14, 1032 (2002) |

DISCLOSURE OF THE INVENTION

An object of the present invention is to provide an organic EL element, an illumination device and a display device, exhibiting a high emission efficiency and a long emission life.

One of the aspects of the present invention is an organic electroluminescence element material comprising a platinum complex having a platinum ion and a ligand comprising an aryl group of which free rotation is blocked or an aromatic heterocycle group of which free rotation is blocked.

BRIEF DESCRIPTION OF THE DRAWINGS

FIG. 6 is a schematic drawing of an illumination device having an organic EL element.

DESCRIPTION OF THE PREFERRED EMBODIMENTS

Figure 1:
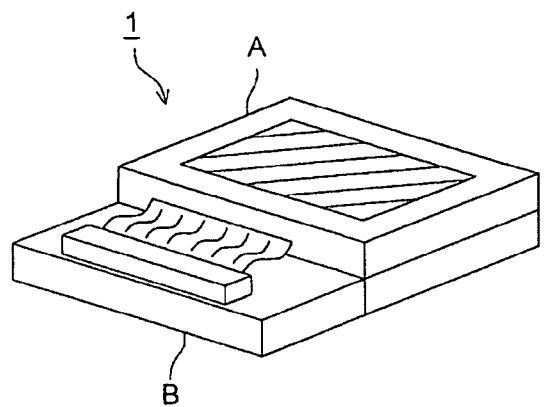
FIG. 1 is a schematic drawing of one example of a display device containing an organic EL element.

The above object of the present invention is achieved by the following structures.

(1) An organic electroluminescence element material comprising a platinum complex having a platinum ion and a ligand comprising an aryl group of which free rotation is blocked or an aromatic heterocycle group of which free rotation is blocked.

(2) The organic electroluminescence element material of Item (1), wherein the platinum complex is an ortho-metallated complex.

(3) The organic electroluminescence element material of Item (2), wherein the ortho-metallated complex is a platinum complex represented by Formula (1) or a tautomer of a compound represented by Formula (1):

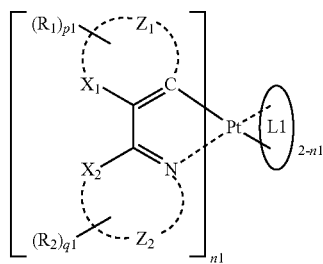

Formula (1)

wherein $R_1$ and $R_2$ each represent a hydrogen atom or a substituent, provided that one of $R_1$ and $R_2$ is the substituent; $X_1$ and $X_2$ each represent a carbon atom, a nitrogen atom, an oxygen atom, or a sulfur atom; $Z_1$ and $Z_2$ each represent a group of atoms necessary to form an aromatic hydrocarbon ring or an aromatic heterocycle; n1 represents an integer of 1 or 2, provided that, when n1 is 1, L1 represents a bidentate ligand; and p1 and q1 each represent an integer of 0-4.

(4) The organic electroluminescence element material of Item (2), wherein the ortho-metallated complex is a platinum complex represented by Formula (2) or a tautomer of a compound represented by Formula (2):

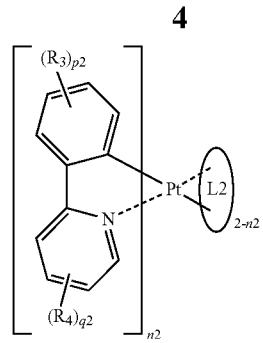

Formula (2)

wherein $R_3$ and $R_4$ each represent a hydrogen atom or a substituent, provided that one of $R_3$ and $R_4$ is the substituent; n2 represents an integer of 1 or 2, provided that, when n2 is 1, L2 represents a bidentate ligand; and p2 and q2 each represent an integer of 0-4.

(5) The organic electroluminescence element material of Item (2), wherein the ortho-metallated complex is a platinum complex represented by Formula (3) or a tautomer of a compound represented by Formula (3):

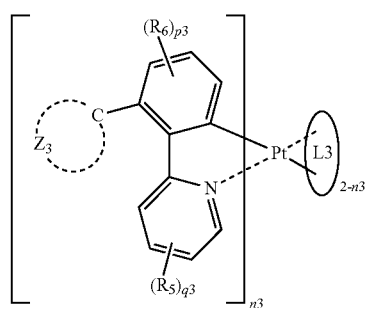

Formula (3)

wherein $R_5$ and $R_6$ each represent a hydrogen atom or a substituent; $Z_3$ represents a group of atoms necessary to form an aromatic hydrocarbon ring or an aromatic heterocycle; n3 represents an integer of 1 or 2, provided that, when n3 is 1, L3 represents a bidentate ligand; p3 represents an integer of 0-3; and q3 epresents an integer of 0-4.

(6) The organic electroluminescence element material of Item (2), wherein the ortho-metallated complex is a platinum complex represented by Formula (4) or a tautomer of a compound represented by Formula (4):

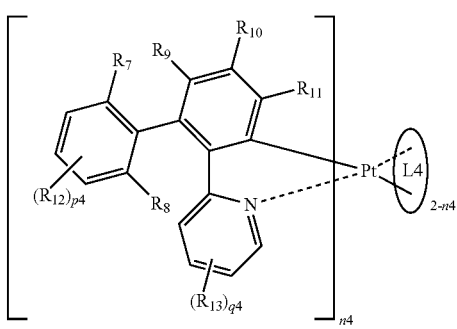

Formula (4)

wherein $R_7$ and $R_8$ each represent a hydrogen atom or a substituent; $R_9$-$R_{13}$ each represent a hydrogen atom or a substituent; n4 represents an integer of 1 or 2, provided that, when n4 is 1, L4 represents a bidentate ligand; p4 represents an integer of 0-3; and q4 represents an integer of 0-4.

(7) The organic electroluminescence element material of Item (2), wherein the ortho-metallated complex is a platinum complex represented by Formula (5) or a tautomer of a compound represented by Formula (5):

Formula (5)

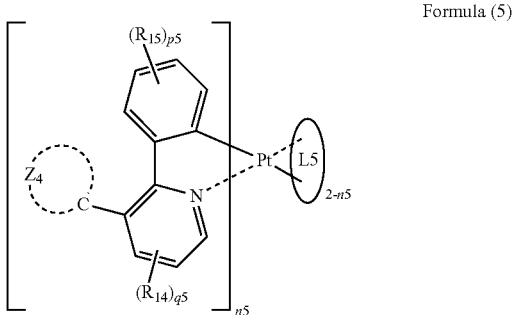

wherein $R_{14}$ and $R_{15}$ each represent a hydrogen atom or a substituent; $Z_4$ represents a group of atoms necessary to form an aromatic hydrocarbon ring or an aromatic heterocycle; n5 represents an integer of 1 or 2, provided that, when n5 is 1, L5 represents a bidentate ligand; p5 represents an integer of 0-4; and q5 represents an integer of 0-3.

(8) The organic electroluminescence element material of Item (2), wherein the ortho-metallated complex is a platinum complex represented by Formula (6) or a tautomer of a compound represented by Formula (6):

Formula (6)

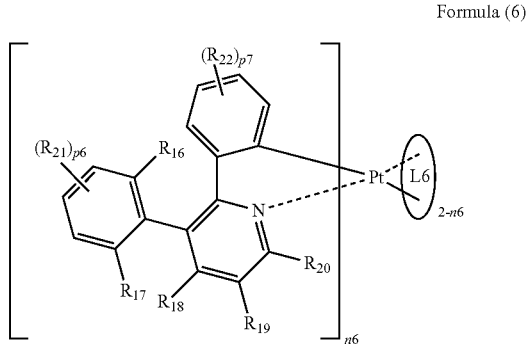

wherein $R_{16}$ and $R_{17}$ each represent a hydrogen atom or a substituent; $R_{18}$-$R_{22}$ each represent a hydrogen atom or a substituent; n6 represents an integer of 1 or 2, provided that, when n6 is 1, L6 represents a bidentate ligand; p6 represents an integer of 0-3; and p7 represents an integer of 0-4.

(9) The organic electroluminescence element material of Item (2), wherein the ortho-metallated complex is a platinum complex represented by Formula (7) or a tautomer of a compound represented by Formula (7):

Formula (7)

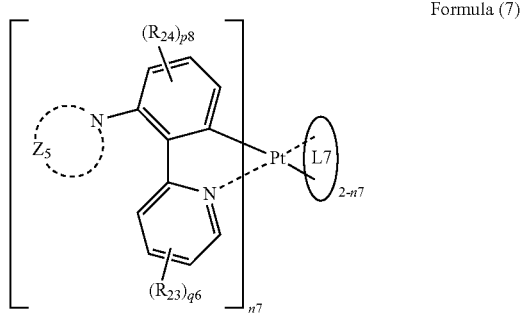

wherein $R_{23}$ and $R_{24}$ each represent a hydrogen atom or a substituent; $Z_5$ represents a group of atoms necessary to form an aromatic heterocycle containing a nitrogen atom; n7 represents an integer of 1 or 2, provided that, when n7 is 1, L7 represents a bidentate ligand; p8 represents an integer of 0-3; and q6 represents an integer of 0-4.

(10) The organic electroluminescence element material of Item (2), wherein the ortho-metallated complex is a platinum complex represented by Formula (8) or a tautomer of a compound represented by Formula (8):

Formula (8)

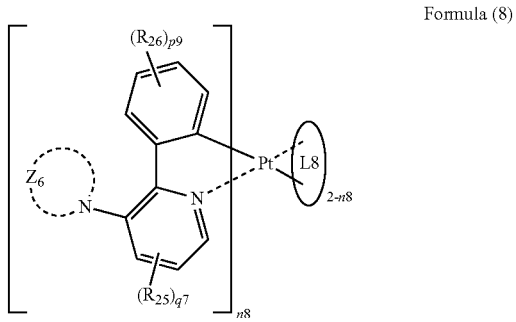

wherein $R_{25}$ and $R_{26}$ each represent a hydrogen atom or a substituent; $Z_6$ represents a group of atoms necessary to form an aromatic heterocycle containing a nitrogen atom; n8 represents an integer of 1 or 2, provided that, when n8 is 1, L8 represents a bidentate ligand; p9 represents an integer of 0-3; and q7 represents an integer of 0-4.

(11) The organic electroluminescence element material of Item (2), wherein the ortho-metallated complex is a platinum complex represented by Formula (9) or a tautomer of a compound represented by Formula (9):

Formula (9)

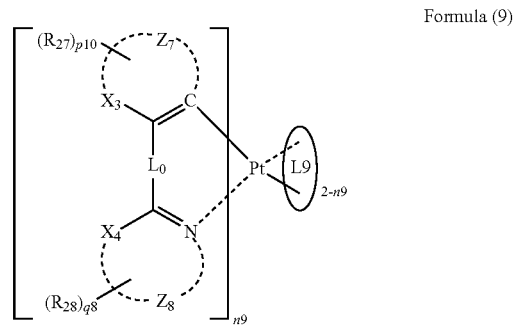

wherein $R_{27}$ and $R_{28}$ each represent a hydrogen atom or a substituent, provided that one of $R_{27}$ and $R_{28}$ is the substituent; $L_0$ represents a divalent linking group; $X_3$ and $X_4$ each represent a carbon atom, a nitrogen atom, an oxygen atom, or a sulfur atom; $Z_7$ and $Z_8$ each represent a group of atoms necessary to form an aromatic hydrocarbon ring or an aromatic heterocycle; n9 represents an integer of 1 or 2, provided that, when n9 is 1, L9 represents a bidentate ligand; and p10 and q8 each represent an integer of 0-4.

(12) The organic electroluminescence element material of any one of Items (1) to (11), wherein the aryl group of which free rotation is blocked is an aryl group having a substituent A and the aromatic heterocycle of which free rotation is blocked is an aromatic heterocycle having a substituent B.

(13) The organic electroluminescence element material of any one of Items (1) to (13), wherein the substituent A or the substituent B is a electron donating substituent.

(14) An organic electroluminescence element comprising the organic electroluminescence element material of any one of Items (1) to (13).

(15) An organic electroluminescence element comprising a emission layer as a constituting layer, wherein the emission layer comprises the organic electroluminescence element material of any one of Items (1) to (13).
(16) The organic electroluminescence element of Item (15), wherein the emission layer comprises a compound represented by Formula (10):

Formula (10)

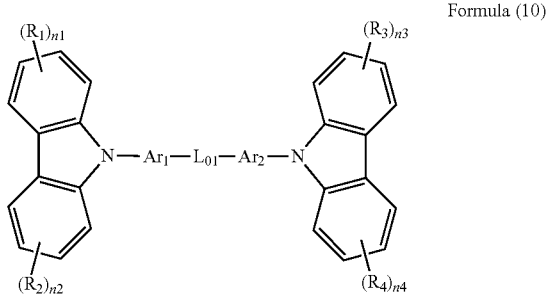

wherein $R_1$, $R_2$, $R_3$ and $R_4$ each represent a hydrogen atom or a substituent; n1, n2, n3, and n4 each represent an integer of 0-4; and $Ar_1$ and $Ar_2$ each represent an arylene group or a divalent aromatic heterocycle group; and $L_{01}$ represents a divalent linking group.
(17) The organic electroluminescence element of Item (15), wherein the emission layer comprises a compound represented by Formula (11):

Formula (11)

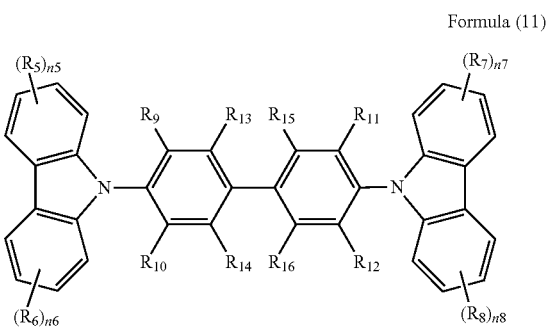

wherein $R_5$-$R_{16}$ each represent a hydrogen atom or a substituent, provided that one of $R_{13}$-$R_{16}$ represents the substituent; and n5-n8 each represent an integer of 0-4.
(18) The organic electroluminescence element of any one of Items (15) to (17), wherein the emission layer comprises a carboline derivative or a carboline derivative, one of carbon atoms of a hydrocarbon ring constituting a carboline ring of the carboline derivative being replaced with a nitrogen atom.
(19) The organic electroluminescence element of any one of Items (15) to (18) further comprising a hole blocking layer as a constituting layer, wherein the hole blocking layer comprises a carboline derivative or a carboline derivative, one of carbon atoms of a hydrocarbon ring constituting a carboline ring of the carboline derivative being replaced with a nitrogen atom.
(20) The organic electroluminescence element of any one of Items (15) to (19) further comprising a hole blocking layer as a constituting layer, wherein the hole blocking layer comprises a boron derivative.
(21) The organic electroluminescence element of Item (19) or (20) comprising a hole blocking layer as one of the constituting layers, wherein the hole blocking layer comprises the organic electroluminescence element material of any one of Iems (1) to (13).
(22) A display devise comprising the organic electroluminescence element of any one of Items (1) to (21).
(23) An illumination devise comprising the organic electroluminescence element of any one of Items (1) to (21).

Details of the present invention will be described below.

In the organic EL element material of the present invention, by having a structure of any one of Items (1)-(13), obtained is a platinum complex which exhibits a specific structure containing a ligand which has at least one aryl group of which free rotation is blocked or at least one aromatic heterocycle group of which free rotation is blocked.

It was found that the organic EL element having a structure described in any one of Items (14)-(21) exhibited a largely improved emission life while exhibiting a high emission efficiency which is one of the characteristics of the conventional platinum complex. By using the organic EL element of the present invention, a display device of claim 22 and an illumination device of Item (23) can be obtained.

Detail of each structural component of the present invention will be described sequentially.

As the results of intense investigation, it was found that the short emission life which has been one of the problems of the organic EL element prepared by using the conventional platinum complex was largely improved by an organic EL element containing a platinum complex having a platinum ion and a ligand containing an aryl group of which free rotation is blocked or an aromatic heterocycle group of which free rotation is blocked.

Among the platinum complexes, preferably utilized is an ortho-metallated complex, specifically ortho-metallated complexes represented by each of Formulae (1)-(9).

As the layer in which an abovementioned platinum complex is incorporated in an organic EL element, preferable are an emission layer (a light emission layer) and/or a hole blocking layer (an electron hole blocking layer). When the platinum compound was incorporated in an emission layer, it was used as an emission dopant in the emission layer, and elongation of emission life of the organic EL element was attained.

The reason why the emission life was prolonged when the abovementioned platinum complex was used as one of the organic EL element materials of the present invention is still under investigation, however, the present inventors assume that it is because the formation of excimer is suppressed by the loss of planarity, which is an intrinsic nature of a platinum complex, due to the steric hinderance caused by the ligand having an aryl group of which free rotation is blocked or an aromatic heterocycle group of which free rotation is blocked.
<<Platinum Complex>>

The platinum complex of the organic EL element material of the present invention will now be explained.

The platinum complex of the present invention is comprised of a platinum ion and a ligand comprising an aryl group of which free rotation is blocked or an aromatic heterocycle group of which free rotation is blocked.
<<Aryl Group of Which Free Rotation is Blocked, Aromatic Heterocycle Group of Which Free Rotation is Blocked>>

In the present invention, an aryl group of which free rotation is blocked and an aromatic heterocycle group of which free rotation is blocked each represent a substituent having a bond about which rotation is inhibited due to steric hinderance.

The state represented by "free rotate is blocked" definitely includes the case when the free rotation of an aryl group or an aromatic heterocycle group is physically inhibited because these groups are located closely to other substituent, while also included is the case when the free rotation of an aryl group or an aromatic heterocycle group is inhibited due to a rotation barrier originated from a conformation energy of the substituent bonded through a bond axis of an aryl group or an aromatic heterocycle group.

The conformation energy forming a bond-rotation barrier is preferably not less than $10^5$ kJ/mole.

In the present invention, preferable is an aryl group or an aromatic heterocycle group of which free rotation is physically blocked.

Examples of an aryl group which can be used as the aryl group of which free rotation is blocked include: a phenyl group, a tolyl group, a xylyl group, a biphenyl group, a naphthyl group, an anthryl group and a phenanthryl group.

Examples of an aromatic heterocycle group which can be used as the aromatic heterocycle group of which free rotation is blocked include: a furyl group, a thienyl group, a pyridyl group, a pyridazinyl group, a pyrimidinyl group, a pyrazinyl group, the triazinyl group, an imidazolyl group, a pyrazolyl group, a thiazolyl group, a quinazolinyl group, the phthalazinyl group A case in which the free rotation of a phenyl group is possible and a case in which the free rotation of a phenyl group is blocked will now be specifically explained below, using the following exemplified compounds (A), (B) and (C).

Exemplified Compound (A)

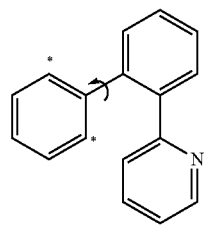

(A)

Exemplified Compound (B)

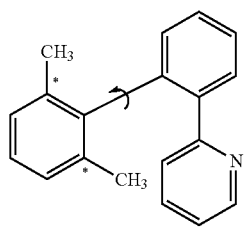

(B)

Exemplified Compound (C)

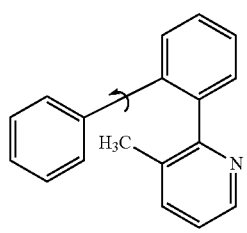

(C)

As substituents of a phenyl group of 2-phenylpyridine, exemplified compounds (A) and (B) represent non-substituted 2'-phenyl group and 2'-phenyl group substituted with two methyl groups on two neighboring carbon atoms of the bond axis, respectively.

In exemplified compound (A), the free rotation of the 2'-phenyl group is possible, while, in exemplified compound (B), free rotation of the 2'-phenyl group is blocked by the existence of two methyl groups.

In the present invention, "the aryl group of which free rotation is blocked" and "the aromatic heterocycle group of which free rotation is blocked" are preferably a substituted aryl group and a substituted aromatic heterocycle group, respectively.

However, the free rotation of the 2'-phenyl group of exemplified compound (C) is also inhibited due to the methyl group which exists in position 3 of pyridine even when it is a non-substituted 2'-phenyl group. This case can also be cited as one of the examples of an aryl group of which free rotation is blocked of the present invention.

Furthermore, the van der Waals (VDW) volume of the substituent (the non-substituted phenyl group in exemplified compound (A) or the 2'-phenyl group substituted with two methyl groups on two neighboring carbon atoms of the bond axis in exemplified compound (B), in the following examples) introduced into the location (the following * position) nearest to the parent moiety (2-phenylpyridine in the following example) is preferably 50 Å$^3$ or more.

The van der Waals (VDW) volume of the substituent is defined as a volume value determined by using the parameters obtained in the simulation soft Cerius 2 produced by Accelrys Software Inc., namely, the van der Waals (VDW) volume of the substituent is calculated using Connoly Surface by optimizing the molecular structure via MM calculation using Dreiding Force Field with a model in which a benzene ring is substituted with a substituent.

| Substituent | Å$^3$ |
|---|---|
| Methyl group | 25.4 |
| Ethyl group | 42.6 |
| Isopropyl group | 59.5 |
| tert-butyl | 76.2 |
| Phenyl group | 74.9 |
| Methoxy group | 34.0 |
| Amino group | 22.2 |
| Hydroxyl | 16.7 |
| Chlorine atom | 22.4 |
| Bromine atom | 26.5 |
| Fluorine atom | 13.3 |
| Trifluoro methyl group | 42.5 |

(Substituent A of an Aryl Group of which Free Rotation is Blocked and Substituent B of an Aromatic Heterocycle Group of which Free Rotation is Blocked)

The aryl group of which free rotation is blocked and the aromatic heterocycle group of which free rotation is blocked of the present invention may be substituted or may not be substituted, provided that the free rotation of each of the aryl group and the aromatic heterocycle group is blocked due to the steric configuration of the ligand of the platinum ion, while when the aryl group and the aromatic heterocycle group may have a substituent, each of substituent A and substituent B is preferably electron donating. In the present invention, "a substituent is electron donating" means that Hammett σp value described below is a negative value and such substituent has a larger tendency to donate electrons to the bonded atoms when compared with a Specific examples of an electron-donating substituent include: a hydroxyl group, a methoxy group, an acetyloxy-group, an amino group, a dimethylamino group, an acetylamino group, alkyl groups (for example, a methyl group, an ethyl group, a propyl group and tert-butyl), and aryl groups (for example, a phenyl group). The following literatures can be referred to for Hammett σp value, for example.

<<Hammett σp Value>>

Hammett σp value of the present invention represents Hammett substituent constant σp. Hammett σp value was determined from the electronic effect of the substituent exerted on hydrolysis of ethyl benzoate by Hammett et al. Groups shown in, for example, "Structure-activity relationship of a drug" (Nankodo Co., Ltd.: 1979), or "Substituent Constants for Correlation Analysis in chemistry and biology" (C. Hansch and A. Leo, John Wiley & Sons, New York, 1979) can be cited.

<<Ortho Metallated Complex>>

The ortho-metallated complex of the present invention will now be described.

As the platinum complex of the present invention, an ortho-metallated complex is preferably used, however, more preferable is the platinum complex described in any one of Formulae (1)-(9).

The ortho-metallated compound of the present invention represents the generic designation of the compounds described, for example, in "Organo-metal chemistry-fundamental and application", p 150, 232 Shokabo Publishing Co., Ltd. written by Akio Yamamoto, published in 1982; "Photochemistry and Photophysics of Coordination Compounds", p71-p77 and p135-p146 Springer-Verlag, written by H. Yersin, published in 1987. In the present invention, it is a metal complex formed with the dissociation of such as the C—H bond or the N—H bond of the ortho-position of an aryl group or an aromatic heterocycle group. Platinum is used as a central metal of the metal complex.

The platinum complex described in any one of Formulae (1)-(9) is characterized in that an aryl group of which free rotation is blocked or an aromatic heterocycle group of which free rotation is blocked is contained in an arbitrary location of a ligand. The organic EL element of the present invention produced using the organic EL element material containing the platinum complex having such physicochemical characteristics can exhibit high luminance while exhibiting a longer emission life, which is different from the conventional organic EL element.

<<Platinum Complex Represented by Formula (1)>>

The platinum complex represented by Formula (1) of the present invention will now be described. In the present invention, the tautomer of a compound represented by Formula (1) is also included.

In Formula (1), examples of a substituent represented by $R_1$ and $R_2$ include: alkyl groups (for example, a methyl group, an ethyl group, and an isopropyl group, a hydroxyethyl group, a methoxymethyl group, a trifluoromethyl group and t-butyl group); cycloalkyl groups (for example, a cyclopentyl group and a cyclohexyl group); aralkyl groups (for example, a benzyl group and a 2-phenethyl group); aryl groups (for example, a phenyl group, a p-chlorophenyl group, a mesityl group, and a tolyl group, a xylyl group, a biphenyl group, a naphthyl group, an anttryl group and a phenanthryl group); aromatic heterocycle groups (for example, a furyl group, a thienyl group, a pyridyl group, a pyridazinyl group, a pyrimidinyl group, a pyrazinyl group, the triazinyl group, an imidazolyl group, a pyrazolyl group, a thiazolyl group, a quinazolinyl group, a carbazolyl group and a phthalazinyl group); alkoxyl groups (for example, an ethoxy group, an isopropoxy group and a butoxy group); aryloxy groups (for example, a phenoxy group and a naphthyloxy group); a cyano group; a hydroxyl group; alkenyl groups (for example, a vinyl group); a styryl group; and halogen atoms (for example, a chlorine atom, a bromine atom, an iodine atom and a fluorine atom, etc.). These groups may be further substituted.

In Formula (1), examples of an aromatic hydrocarbon ring or an aromatic heterocycle represented by $Z_1$ include: a benzene ring, a naphthalene ring, a pyridine ring, a pyridazine ring, a pyrimidine ring, a pyrazine ring, a triazine ring, a furan ring, a thiophene ring, a pyrrole ring, an imidazole ring, a pyrazole ring, a triazole ring and a tetrazole ring. Of these, preferable is a benzene ring.

In Formula (1), examples of an aromatic hydrocarbon ring or an aromatic heterocycle represented by $Z_2$ include: a pyridine ring, a pyridazine ring, a pyrimidine ring, a pyrazine ring, a triazine ring, a benzimidazole ring, a benzothiazole ring, a benzoxazole ring, a quinazoline ring and a phthalazine ring. Of these, preferable is a pyridine ring.

In Formula (1), $n_1$ is an integer of 1 or 2, and when n1 is 1, L1 represents bidentate ligand. Examples of a bidentate ligand represented by L1 include: oxycarbolic acids, oxyaldehyde, and derivatives thereof (for example, salicyl aldehydato and oxyaceto phenonato); dioxy compounds (for example, biphenolato); diketones (for example, acetylacetonato, dibenzoylmethanato, diethylmalonato and ethylacetoacetato); oxyquinones (for example, pyromeconato, oxynaphtoquinonato and oxyanthraquinonato); tropolones (for example, troponato and hinokitiolato); N-oxide compound; aminocarboxylic acida and analogue (for example, glycinato, alaninato, anthranilato and picolinato); hydroxylamines (for example, aminophenolato, ethanolaminato, and mercaptoethylaminato), oxines (for example, 8-oxyquinolinato); and aldimines (for example, salicylaldiminato); oxyoximes (for example, benzoineoxymato and salicylaldoximato); oxyazo compounds (for example, oxyazobenzonato and phenylazonaphtolato); nitrosonaphthols (for example, β-nitroso-α-naphtolato), and triazenes (for urets (for example, biuretato and a polypeptide group); formazens; dithizones (for example, diphenylcarbazonato and diphenylthiocarbazonato); piguanides (for example, piguanidato); and glyoximes (for example, dimethylglyoximato).

Formulae and specific examples of a bidentate ligand preferably used in the present invention will be shown below, however, the present invention is not limited thereto.

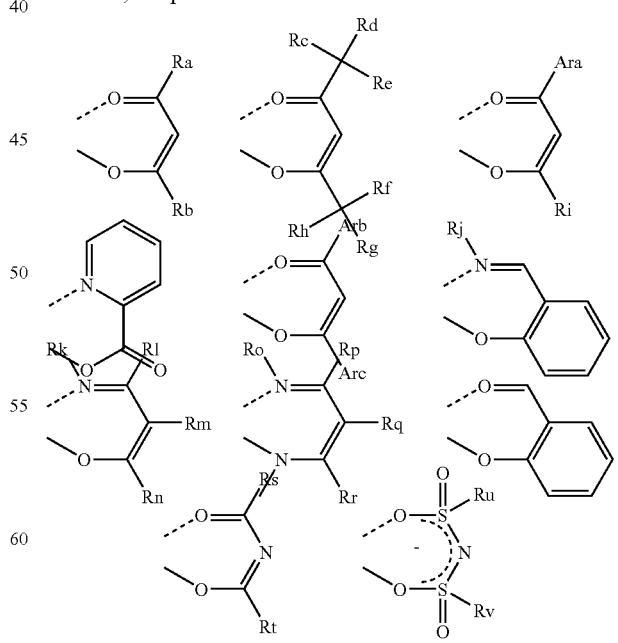

In the above formulae of the bidentate ligands, Ra-Rv each represents an alkyl group (for example, a methyl group, an ethyl group, an isopropyl group, a hydroxyethyl group, a methoxymethyl group, a trifluoromethyl group and a t-butyl group) or an alkylhalide group (for example, the above alkyl groups, at least one of the hydrogen atoms of each alkyl group being replaced with a fluorine atom, a chlorine atom, a bromine atom and an iodine atom).

In the above formulae of the bidentate ligands, Ara-Arc each represent an aryl group (for example, a phenyl group, a p-chlorophenyl group, a mesityl group, a tolyl group, a xylyl group, a biphenyl group, a naphthyl group, an anthryl group and a phenanthryl group) or an aromatic heterocycle group (for example, a furyl group and a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group and a phthalazinyl group).

<<Platinum Complex Represented by Formula (2)>>

The platinum complex represented by Formula (2) of the present invention will now be explained.

In Formula (2), the substituents represented by $R_3$ and $R_4$ are the same as the substituents defined by $R_1$ and $R_2$ in above Formula (1).

In Formula (2), the bidentate ligand represented by L2 is the same as the bidentate ligand defined by L1 in above Formula (1).

<<Platinum Complex Represented by Formula (3)>>

The platinum complex represented by Formula (3) of the present invention will now be explained.

In Formula (3), the substituents represented by $R_5$ and $R_6$ are the same as the substituents defined by $R_1$ and $R_2$ in above Formula (1).

In Formula (3), the bidentate ligand represented by L3 is the same as the bidentate ligand defined by L1 in above Formula (1).

In Formula (3), examples of an aromatic hydrocarbon ring formed by $Z_3$ and C (carbon atom) include: a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthracene ring, a naphthacene ring, a penthacene ring, a perylene ring, a pentaphene ring, a picene ring, a pyrene ring, a pyranthrene ring and an anthranthrene ring. Further, the above aromatic hydrocarbon rings each may have a substituent represented by $R_1$ or $R_2$ in Formula (1).

In Formula (3), examples of an aromatic heterocycle formed by $Z_3$ and C (carbon atom) include: a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring and a carboline ring in which one of carbon atoms of a hydrocarbon ring constituting the carboline ring is replaced with a nitrogen atom. Further, the above-mentioned aromatic heterocycles each may have a substituent represented by $R_1$ or $R_2$ in above Formula (1).

<<Platinum Complex Represented by Formula (4)>>

The platinum complex represented by Formula (4) of the present invention will now be explained.

In Formula (4), the substituents represented by $R_7$-$R_{13}$ are the same as the substituents defined by $R_1$ and $R_2$ in above Formula (1).

In Formula (4), the bidentate ligand represented by L4 is the same as the bidentate ligand defined by L1 in above Formula (1).

<<Platinum Complex Represented by Formula (5)>>

The platinum complex represented by Formula (5) of the present invention will now be explained.

In Formula (5), the substituents represented by $R_{14}$ and $R_{15}$ are the same as the substituents defined by $R_1$ and $R_2$ in above Formula (1).

In Formula (5), the bidentate ligand represented by L5 is the same as the bidentate ligand defined by L1 in above Formula (1).

In formula (5) the aromatic hydrocarbon ring formed by $Z_4$ and C (carbon atom) is the same as that defined by the aromatic hydrocarbon ring formed by $Z_3$ and C (carbon atom).

In formula (5) the aromatic hydrocarbon ring formed by $Z_4$ and C (carbon atom) is the same as that defined by the aromatic hydrocarbon ring formed by $Z_3$ and C (carbon atom).

<<Platinum Complex Represented by Formula (6)>>

The platinum complex represented by Formula (6) of the present invention will now be explained.

In Formula (6), the substituents represented by $R_{16}$—$R_{22}$ are the same as the substituents defined by $R_1$ and $R_2$ in above Formula (1).

In Formula (6), the bidentate ligand represented by L6 is the same as the bidentate ligand defined by L1 in above Formula (1).

<<Platinum Complex Represented by Formula (7)>>

The platinum complex represented by Formula (7) of the present invention will now be explained.

In Formula (7), the substituents represented by $R_{23}$ and $R_{24}$ are the same as the substituents defined by $R_1$ and $R_2$ in above Formula (1).

In Formula (7), the bidentate ligand represented by L7 is the same as the bidentate ligand defined by L1 in above Formula (1).

In Formula (7), examples of an aromatic heterocycle formed by $Z_5$ and N (nitrogen atom) include: a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring, and a carboline ring in which one of carbon atoms of a hydrocarbon ring constituting the carboline ring is replaced with a nitrogen atom. Further, the above-mentioned aromatic heterocycles each may have a substituent represented by $R_1$ or $R_2$ in above Formula (1).

<<Platinum Complex Represented by Formula (8)>>

The platinum complex represented by Formula (8) of the present invention will now be explained.

In Formula (8), the substituents represented by $R_{25}$ and $R_{26}$ are the same as the substituents defined by $R_1$ and $R_2$ in above Formula (1).

In Formula (8), the bidentate ligand represented by L8 is the same as the bidentate ligand defined by L1 in above Formula (1).

In Formula (8), examples of an aromatic heterocycle formed by $Z_6$ and N (nitrogen atom) include: a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring, and a carboline ring in which one of carbon atoms of a hydrocarbon ring constituting the carboline ring is replaced with a nitrogen atom. Further, the above-mentioned aromatic heterocycles each may have a substituent represented by $R_1$ or $R_2$ in above Formula (1).

<<Platinum Complex Represented by Formula (9)>>

The platinum complex represented by Formula (9) of the present invention will now be explained.

In Formula (9), the substituents represented by $R_{27}$ and $R_{28}$ are the same as the substituents defined by $R_1$ and $R_2$ in above Formula (1).

In Formula (9), the bidentate ligand represented by L9 is the same as the bidentate ligand defined by L1 in above Formula (1).

In Formula (9), the 5- or 6-membered ring represented by $Z_7$ is the same as the 5- or 6-membered ring defined by $Z_1$ in Formula (1).

In Formula (9), the 5- or 6-membered ring represented by $Z_8$ is the same as the 5- or 6-membered ring defined by $Z_2$ in Formula (1).

In Formula (9), examples of a divalent linking group represented by $L_0$ include: hydrocarbon groups such as an alkylene group (for example, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, a nonamethylene group, a decamethylene group, a undecamethylene group, a dodecamethylene group, a cyclohexylene group (for example, 1,6-cyclohexanediyl group) and a cyclopentylene group (for example, 1,5-cyclopentanediyl group)), an alkenylene group (for example, a vinylene group and a propenylene group), an alkynylene group (for example, an ethynulene group and a 3-pentinulene group) and a arylene group; and heteroatom-containing groups such as: a divalent group containing a chalcogen atom such as —O— or —S—, and a —N(R)— group in which R represents a hydrogen atom or an alkyl group, where the alkyl group is the same as that defined by $R_1$ and $R_2$ in Formula (1).

Specific examples of the platinum complex used for the organic EL element material of the present invention will bw shown below, however, the present invention is not limited thereto. In the following examples, aryl groups of which free rotation is blocked or aromatic heterocycle groups of which free rotation is blocked are surrounded with dotted lines.

1

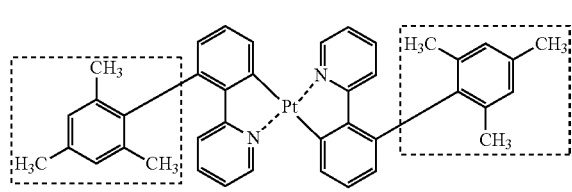

2

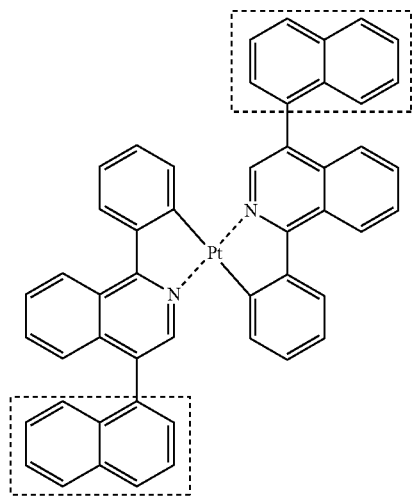

3

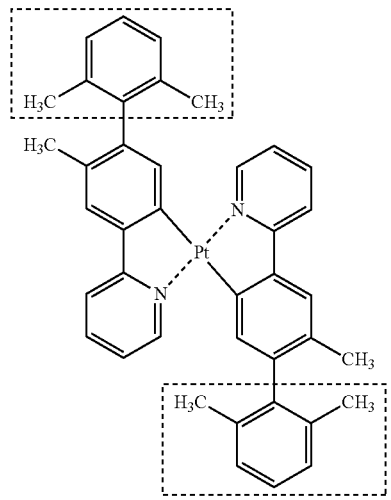

4

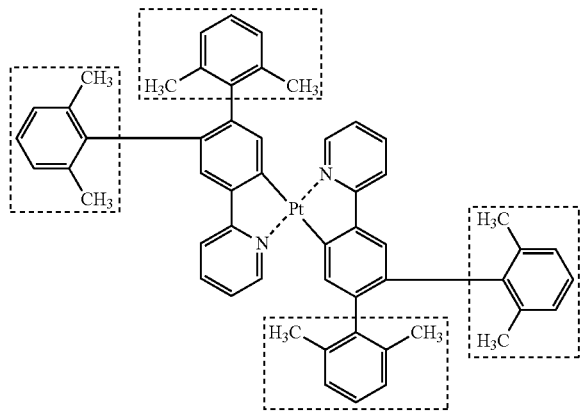

-continued
| | |
|---|---|
| 5 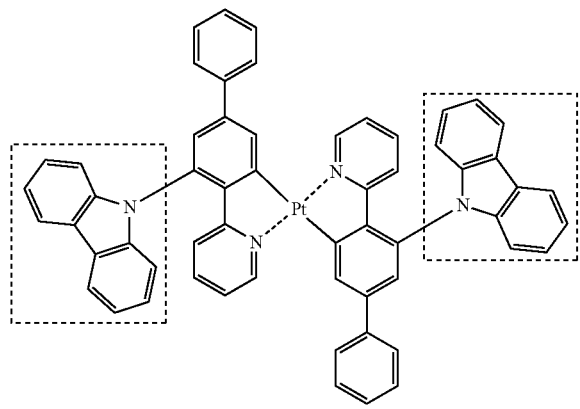 | 6 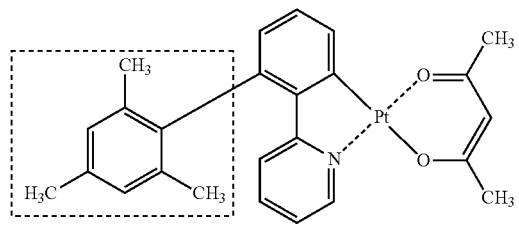 |
| 7 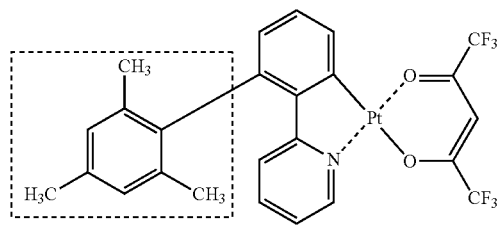 | 8 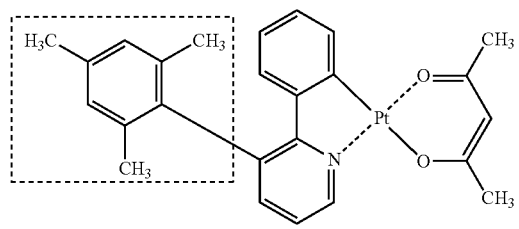 |
| 9 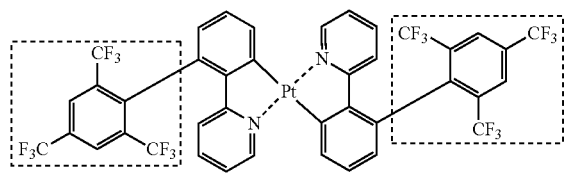 | 10 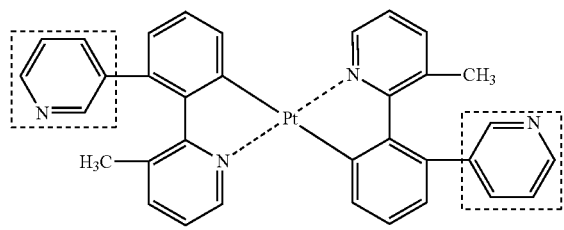 |
| 11 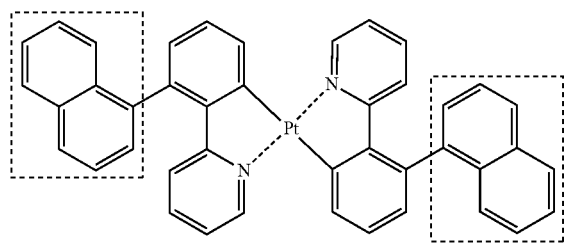 | 12 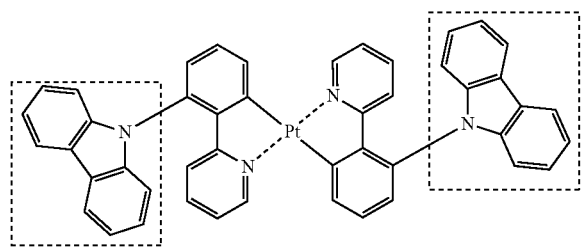 |

-continued
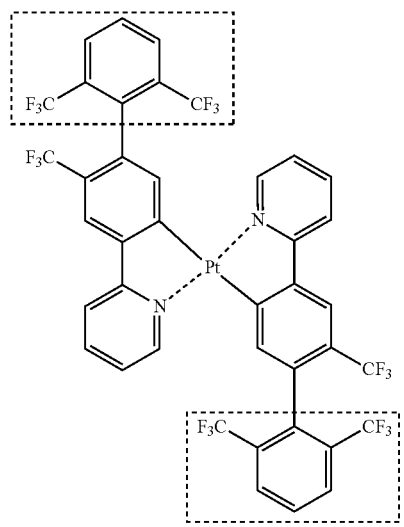
13
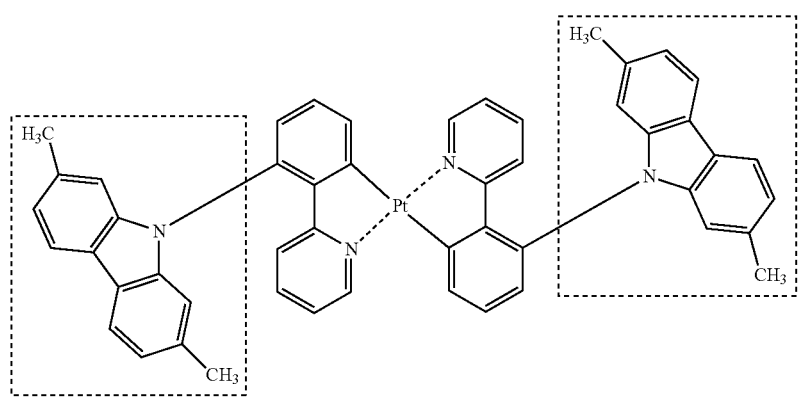
14
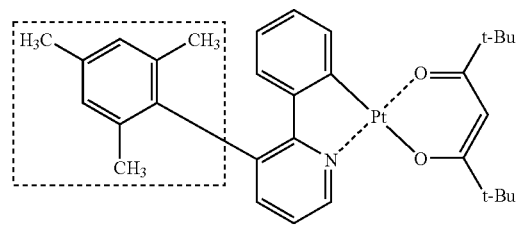
15
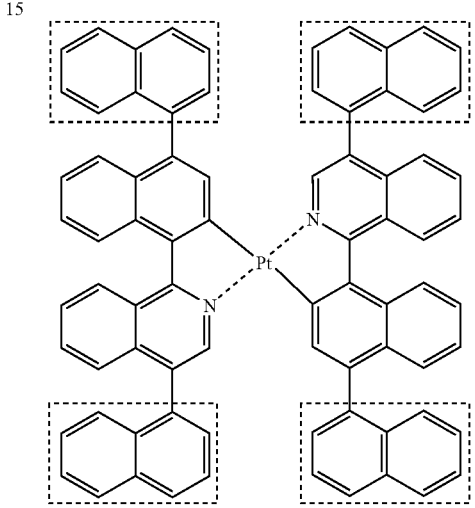
16

-continued
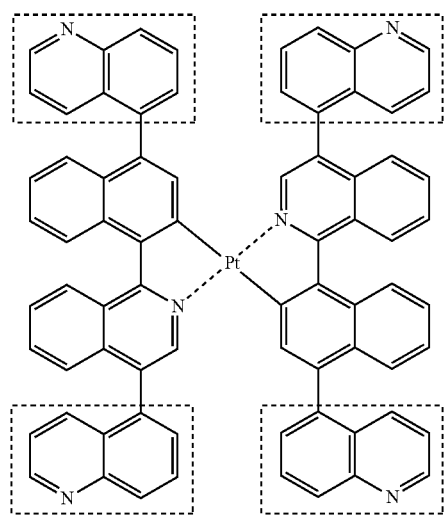
17
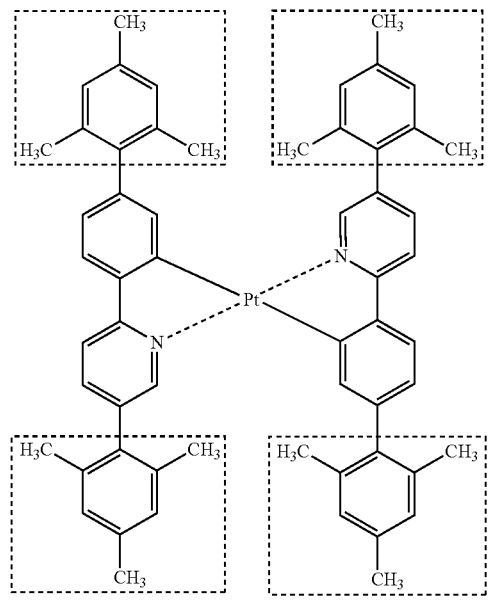
18
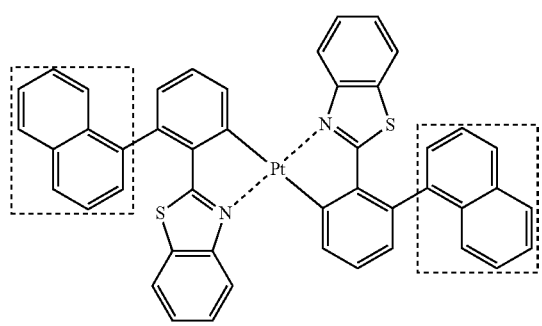
19
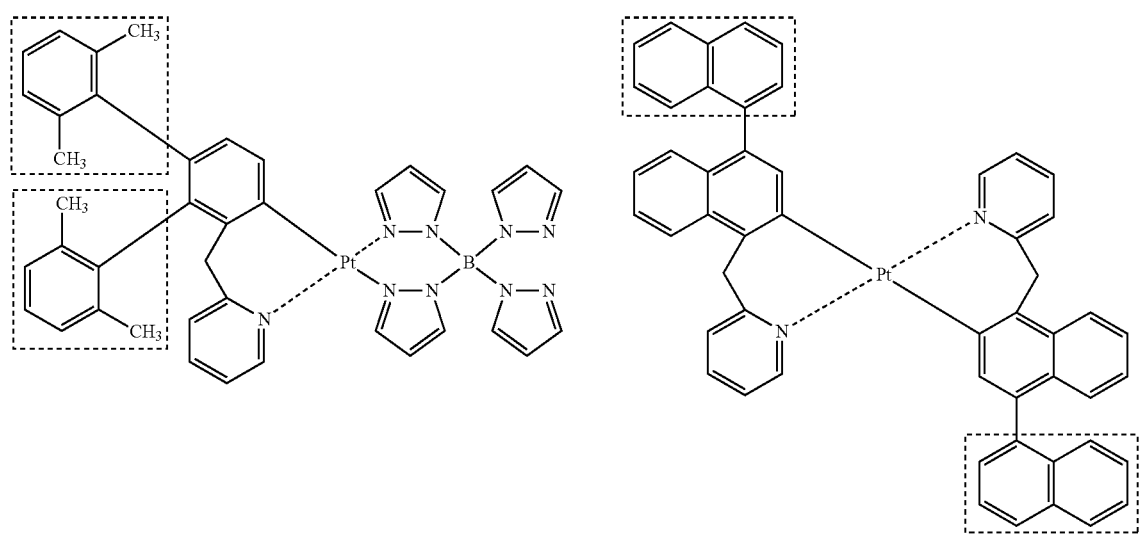
20
21
22
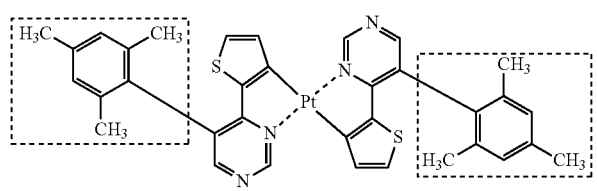

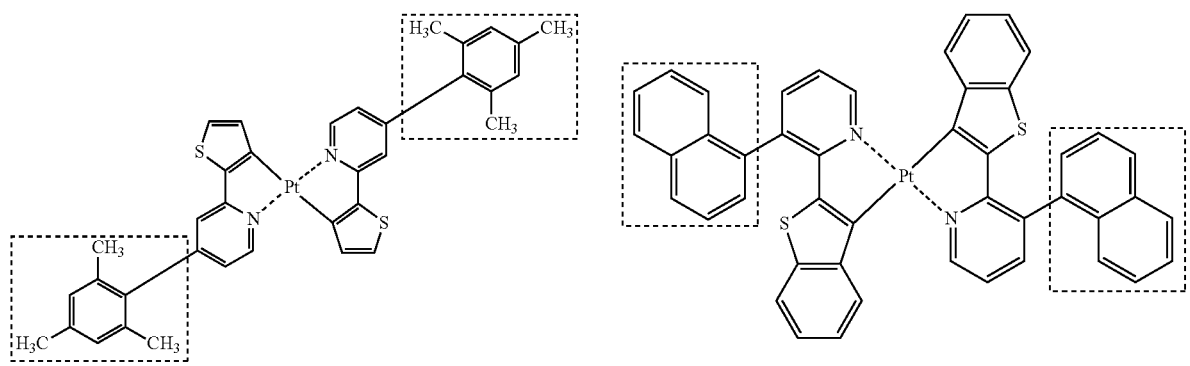
23
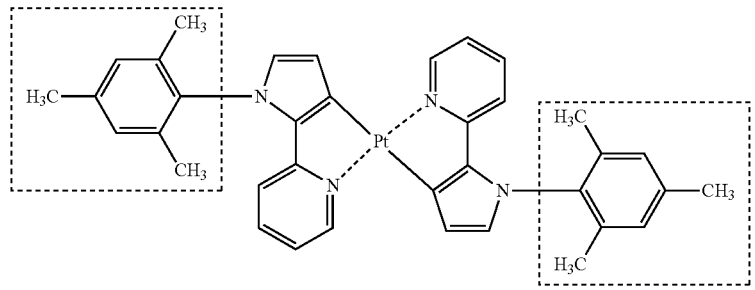
24
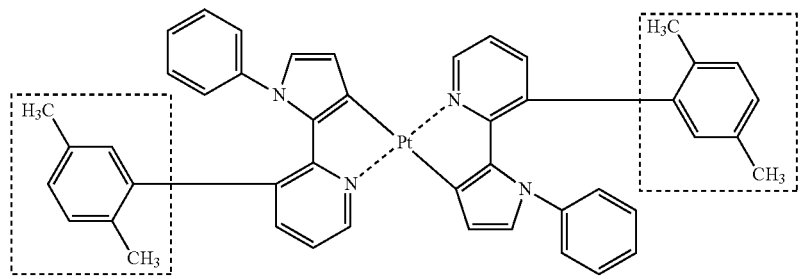
25
26
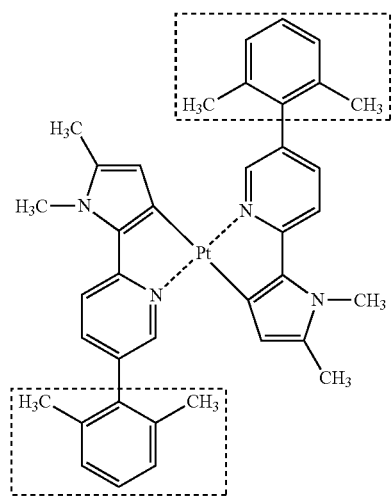
27

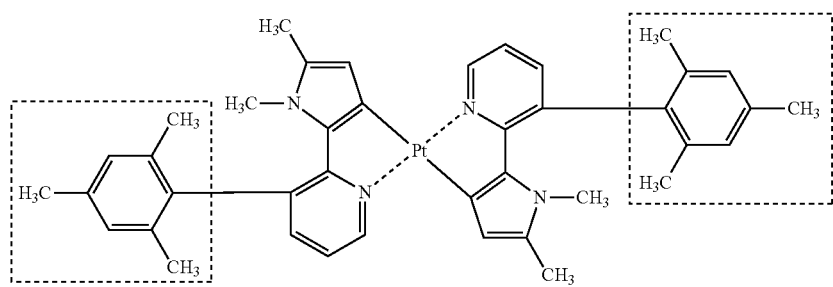
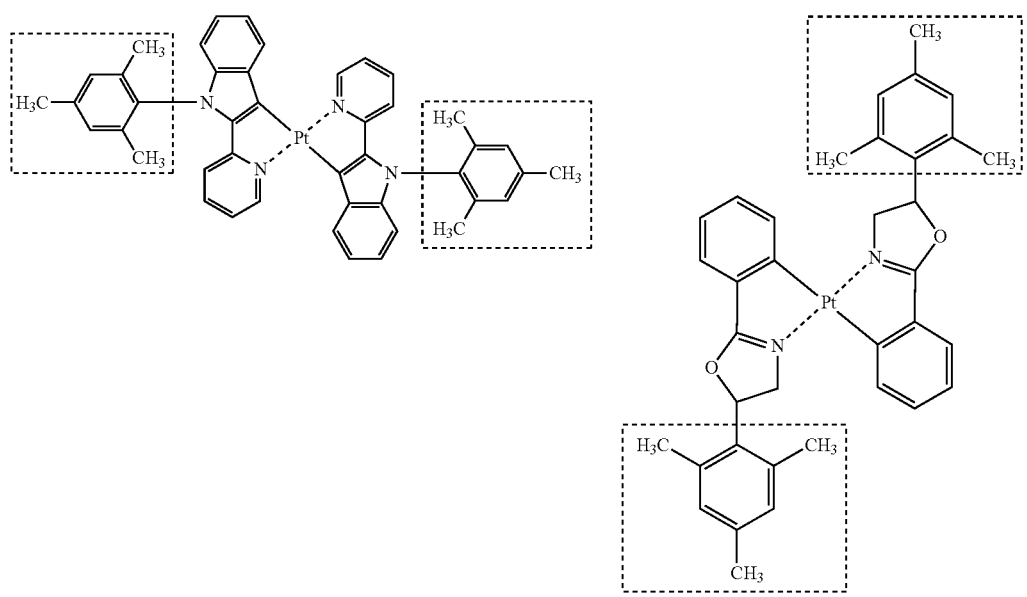
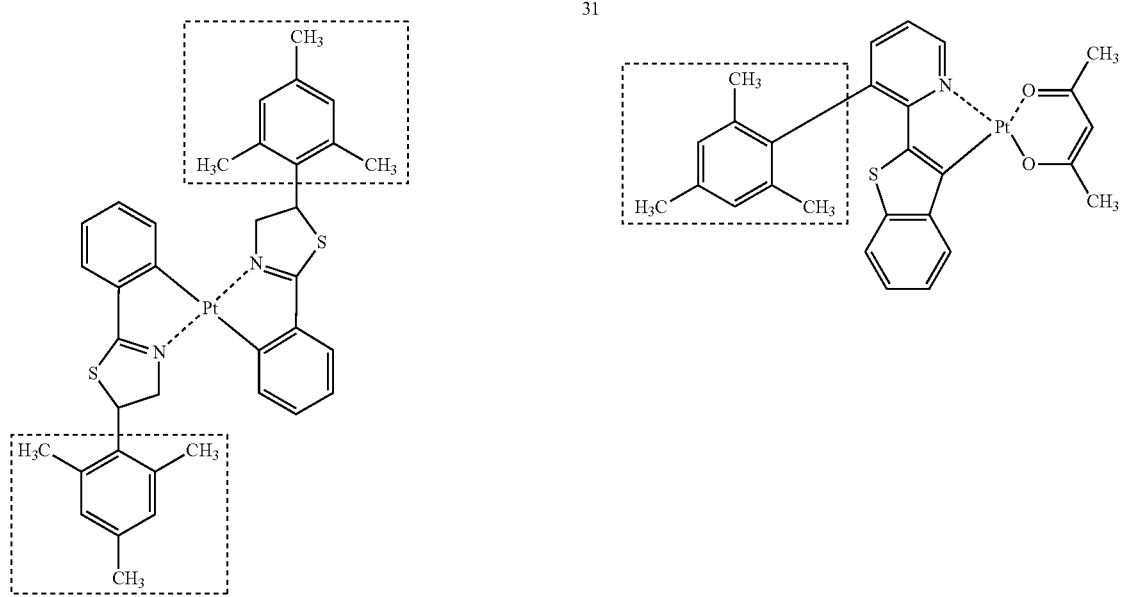

33
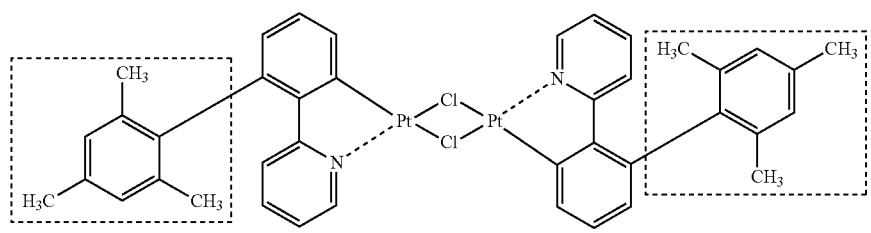
34
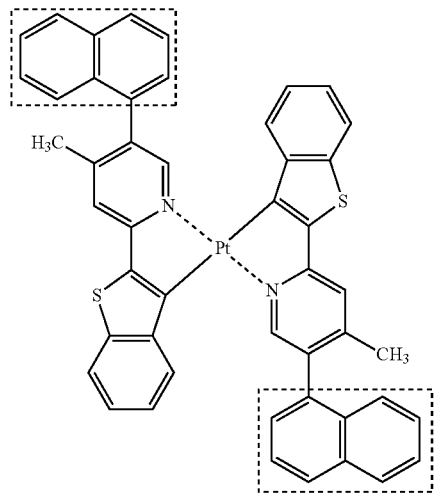
35
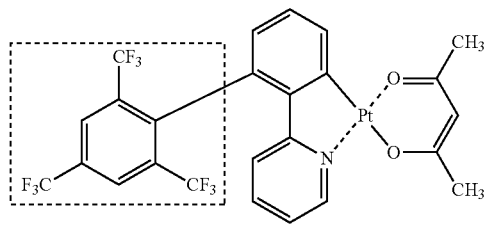
36
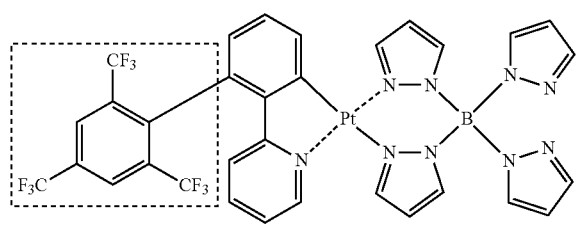
37
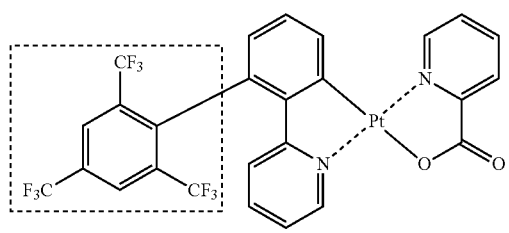
38
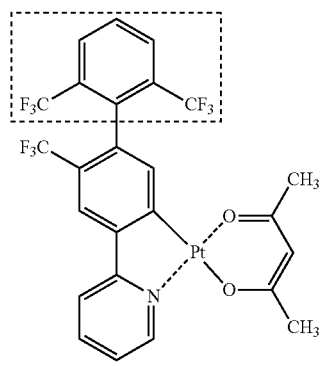
39
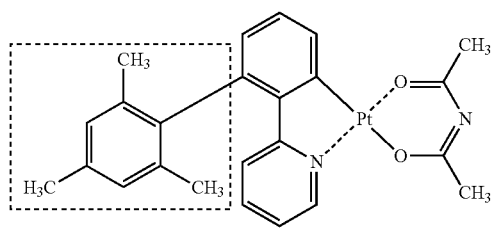
40
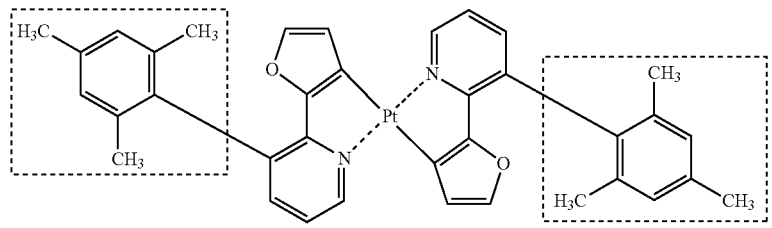

-continued
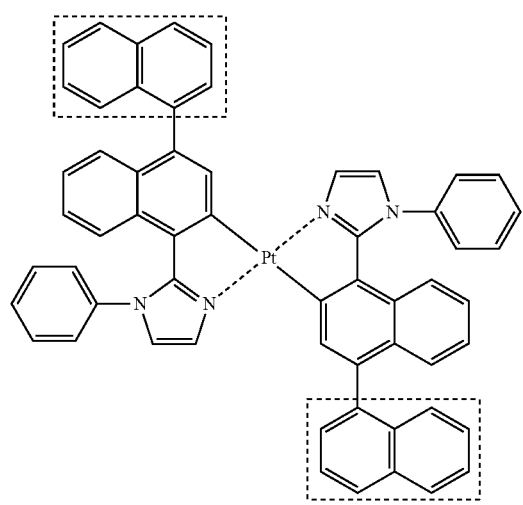
41
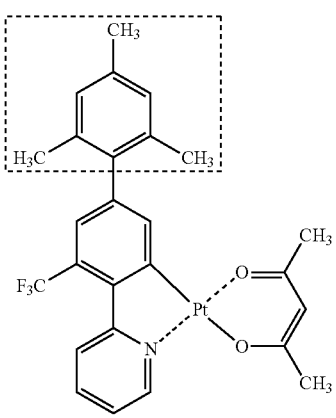
42
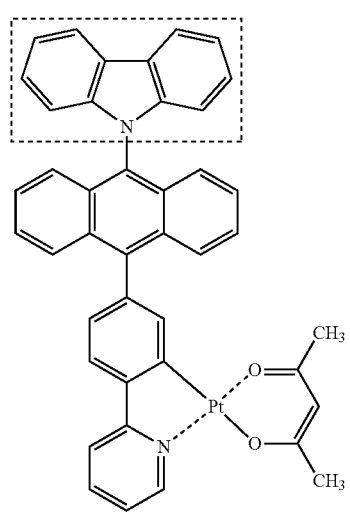
43
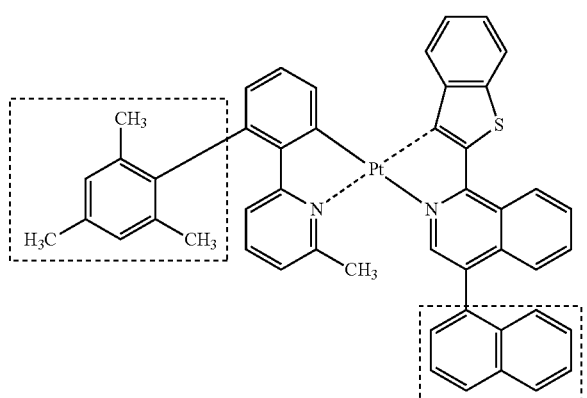
44
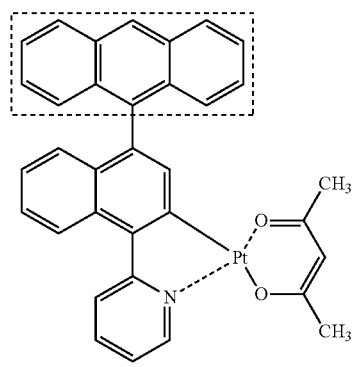
45
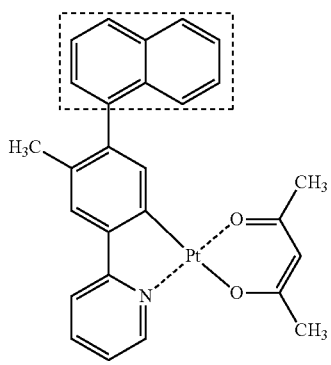
46

-continued
47
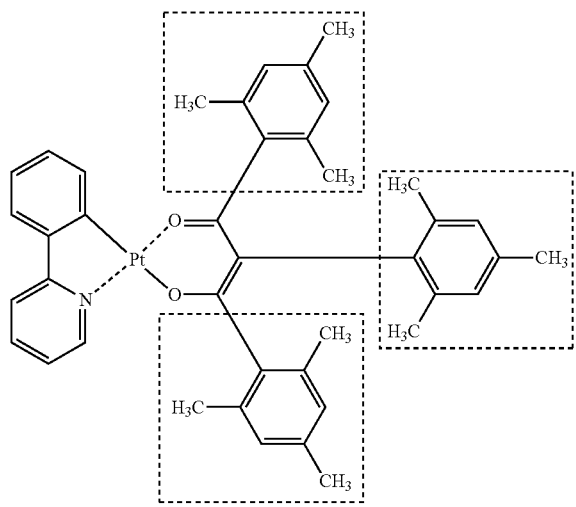
48
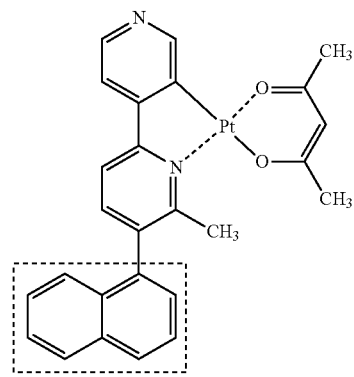
49
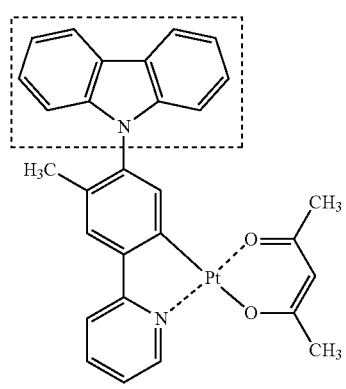
50
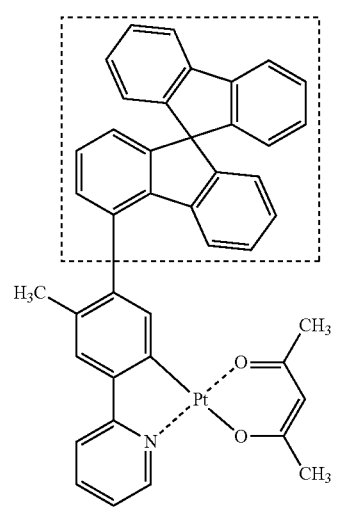
51
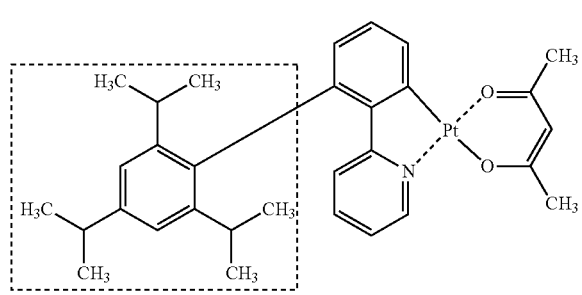
52
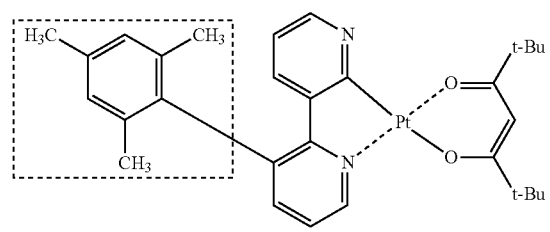

53
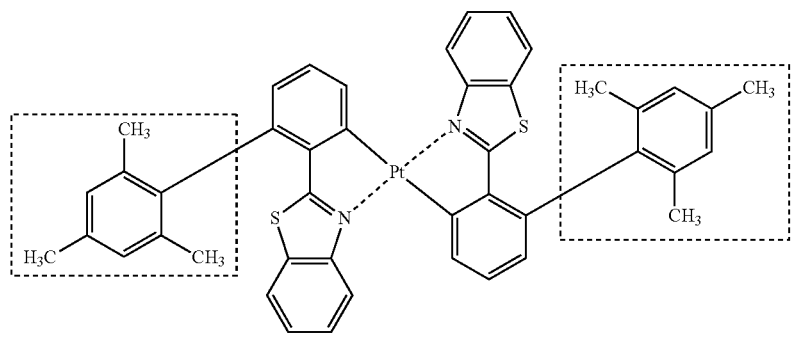
54
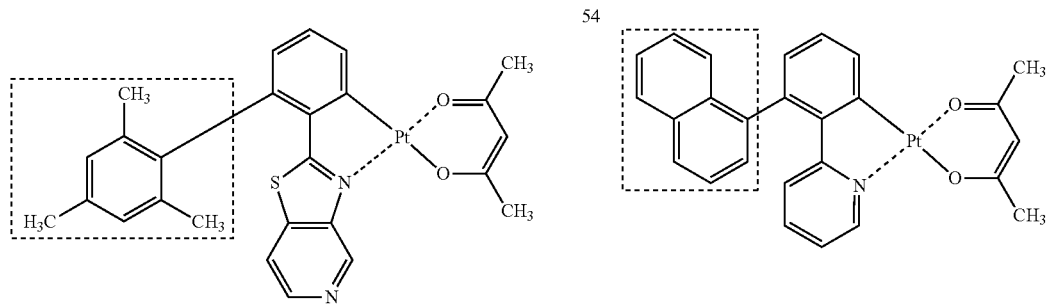
55
56
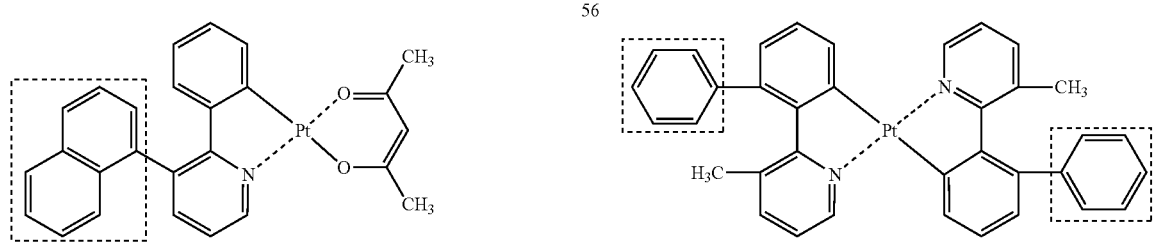
57
58
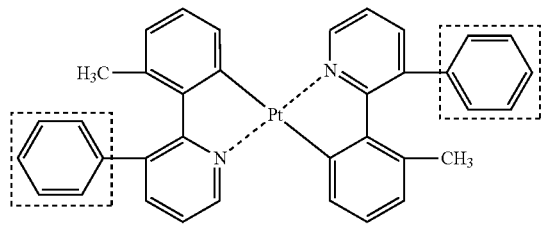
59
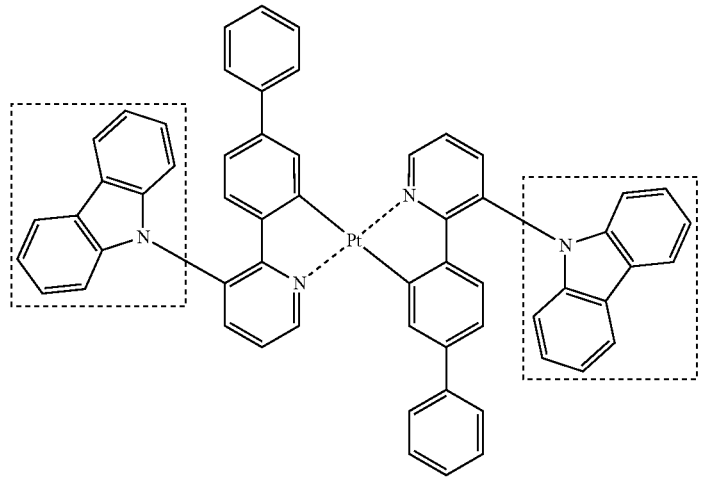

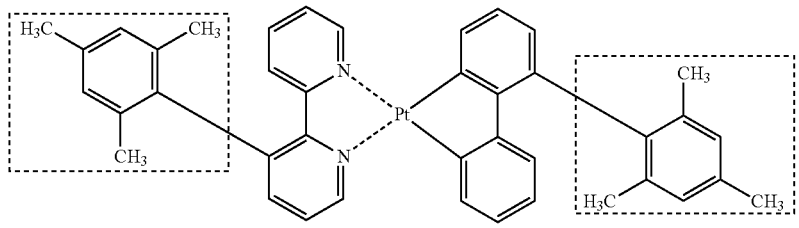
60
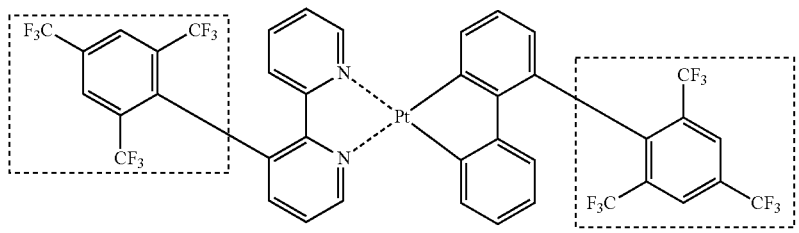
61
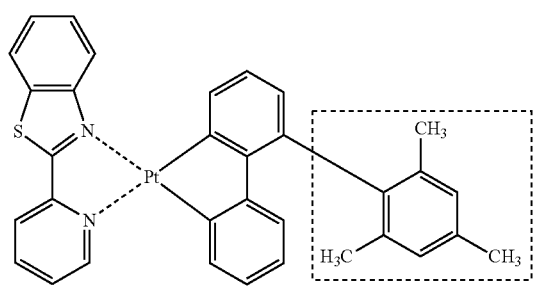
62
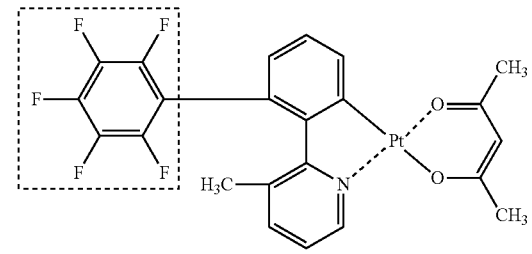
63
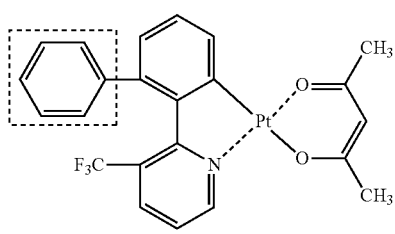
64
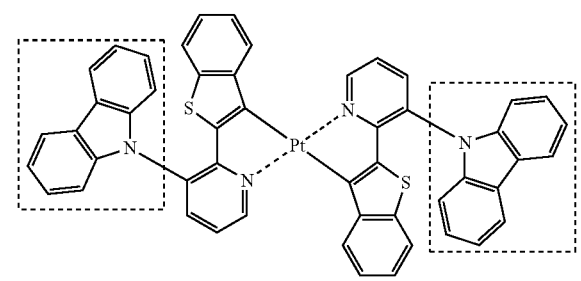
65
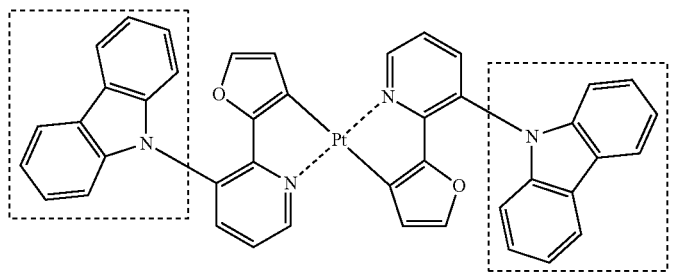
66

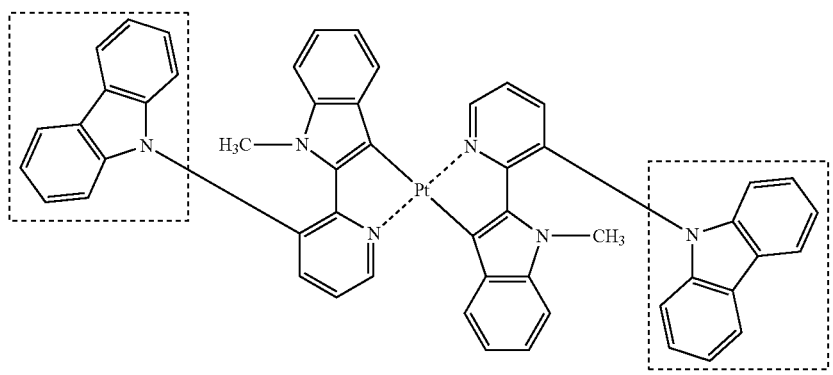
67
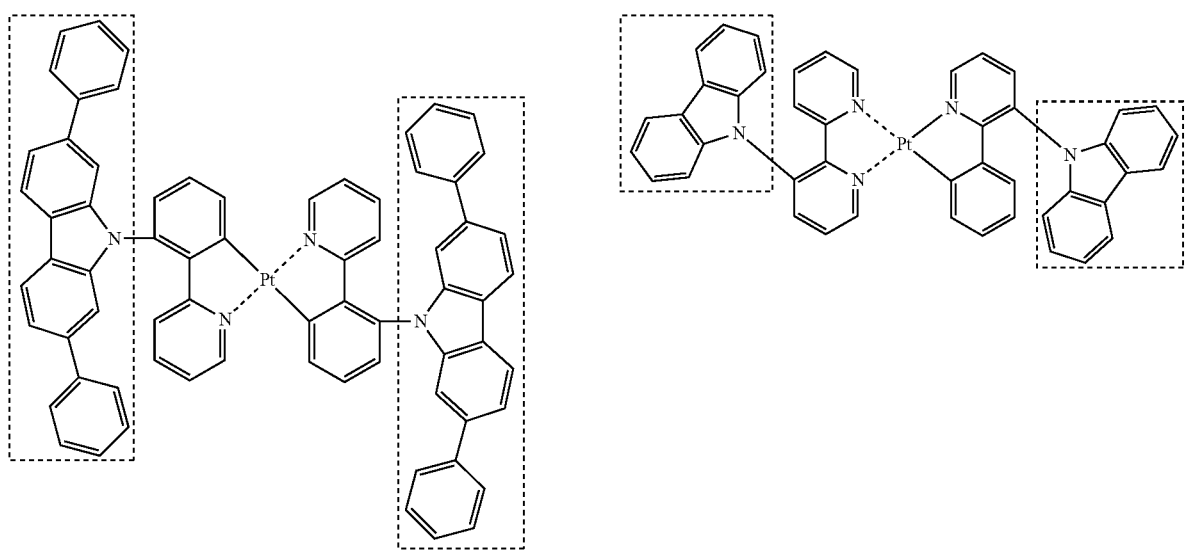
68
69
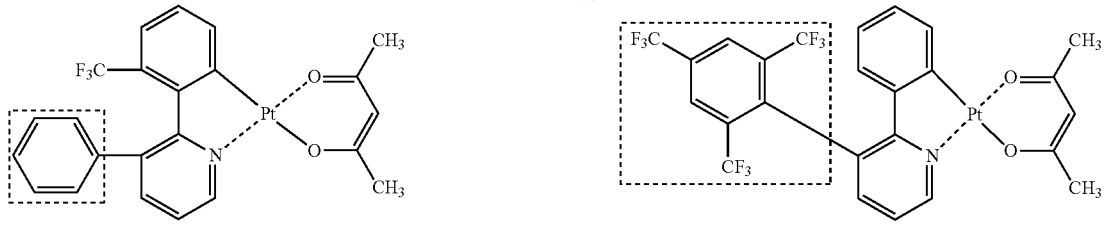
70
71
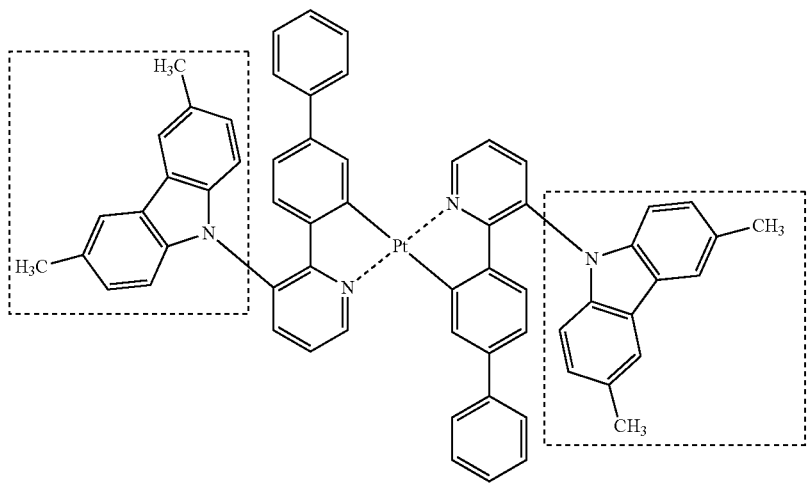
72

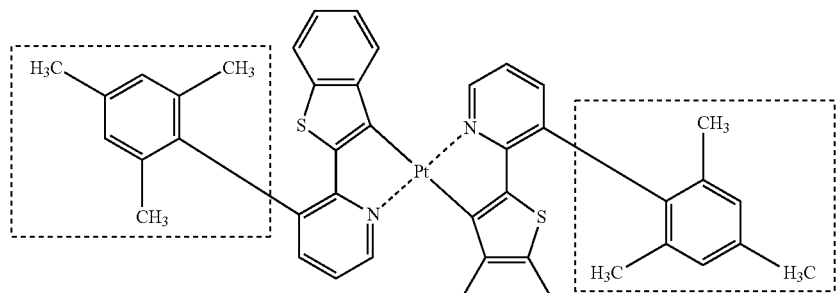

73

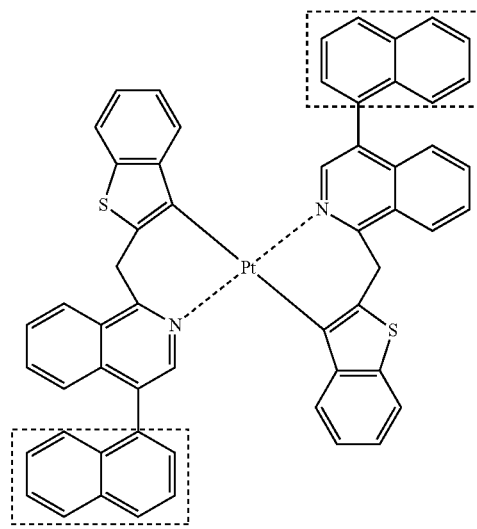

74

The platinum complex of the organic EL element material of the present invention, an ortho-metallated complex, and ortho-metallated complexes represented by each of Formulae (1)-(9) (also referred to as an ortho-metallated platinum complex) are so called metal complexes each containing a central metal platinum (Pt) and a ligand. The ligand of the metal complex can be synthesized by referring to, for example, Organic Letter, Vol 3, No. 16, pp 2579-2581 (2001), and the metal complex containing the above-mentioned ligand and the central metal (Pt) can be synthesized by using a method described in the above literature and in Non-Patent Document 1.

<<Application of Organic EL Element Material Containing Platinum Complex to Organic EL Element>>

When producing an organic EL element using the organic EL element material of the present invention, the organic EL element material is preferably used in the emission layer or in the hole blocking layer among the constituting layers (details will be described later). In the light emission layer, it is preferably used as an emission dopant as mentioned above.

(Emission Host and Emission Dopant)

The content of an emission dopant is preferably not less than 0.1% by weight but less than 30% by weight based on the weight of an emission host, the emission host being a host compound which is a main component of the emission layer.

The emission dopant may be a mixture of plural compounds which may be other metal complexes having different structures or may be a phosphorescent dopant or a fluorescence dopant having other structure.

A dopant (a phosphorescent dopant or a fluorescent dopant) which may be used together with a platinum complex used as an emission dopant will now be explained.

The emission dopant is roughly classified into a fluorescent dopant emitting a fluorescent light and a phosphorescent dopant emitting a phosphorescent light.

Typical examples of the former (a fluorescent dopant) include: a coumarin dye, a pyran dye, a cyanine dye, a chloconium dye, a squalenium dye, an oxobenzanthracene dye, a fluoresceine dye, a rhodamine dye, a pyrylium dye, a perylene dye, a stilbene dye, a polythiophene dye, and a rare earth complex fluorescent material.

As typical examples of the latter (a phosphorescent dopant), preferable is a complex containing a metal of group 8, 9 or 10 in the periodic table of elements, and more preferable is an iridium compound, an osmium compound or an iridium compound. Of these, most preferable is an iridium compound.

Specifically, preferable are the compounds disclosed in the following Patent Documents.

WO00/70655, JP-A Nos. 2002-280178, 2001-181616, 2002-280179, 2001-181617, 2002-280180, 2001-247859, 2002-299060, 2001-313178, 2002-302671, 2001-345183, 2002-324679, WO02/15645 JP-A Nos. 2002-332291, 2002-50484, 2002-332292, 2002-83684, Published Japanese Translation of PCT International Application Publication No. 2002-540572, JP-A Nos. 2002-117978, 2002-338588, 2002-170684, 2002-352960, WO01/93642, JP-A Nos. 2002-50483, 2002-100476, 2002-173674, 2002-359082, 2002-175884, 2002-363552, 2002-184582, 2003-7469, Published Japanese Translation of PCT International Publication No. 2002-525808, JP-A No. 2003-7471, Published Japanese Translation of PCT International Publication No., 2002-

525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678.
A part of the examples will be shown below.
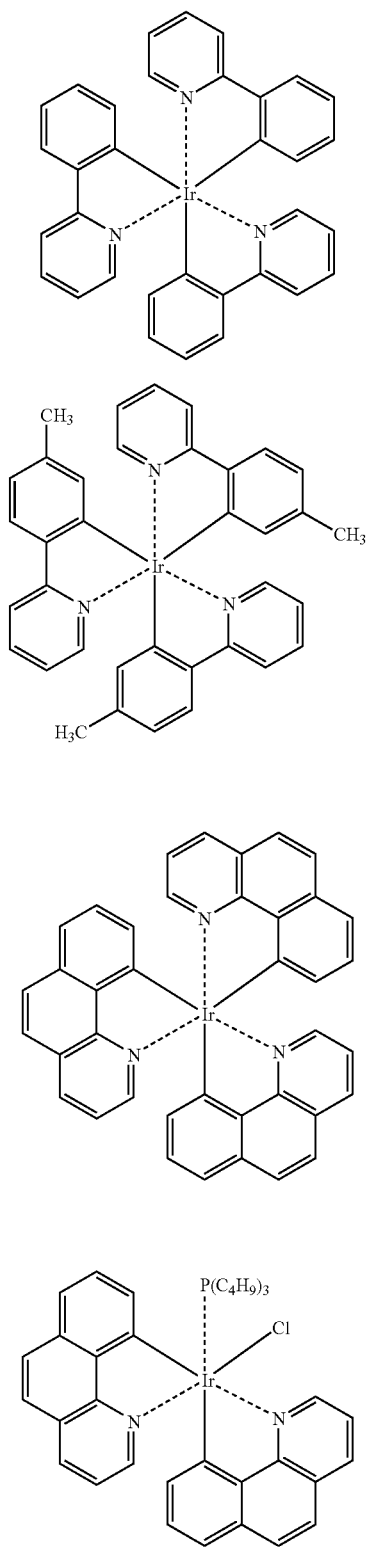
-continued
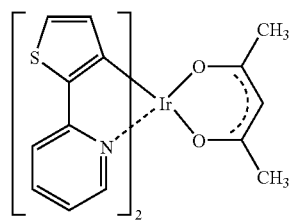
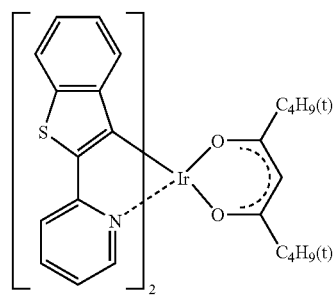
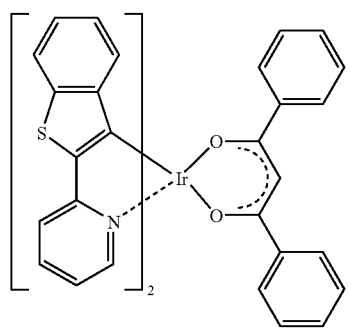
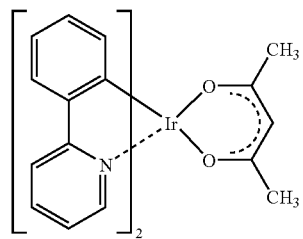
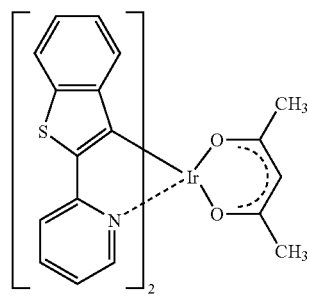

Ir-10 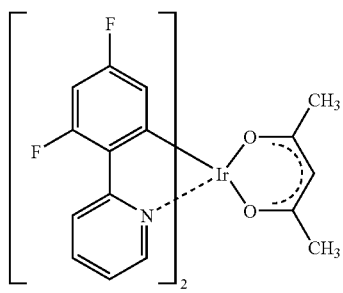

Ir-11 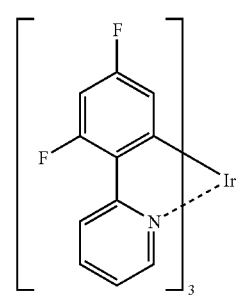

Ir-12 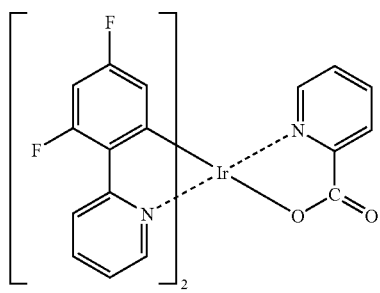

Ir-13 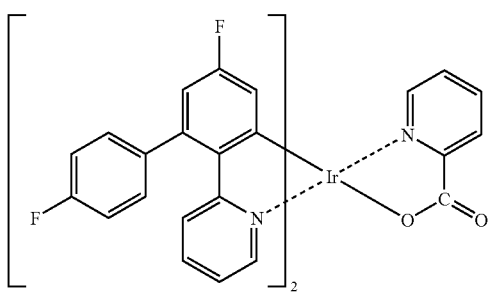

Pt-1 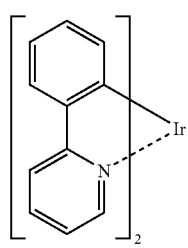

Pt-2 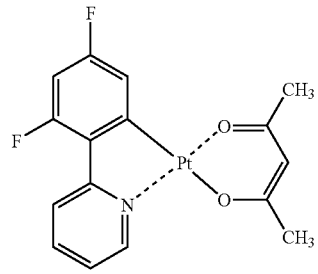

Pt-3 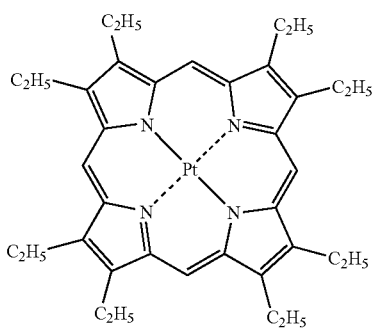

A-1 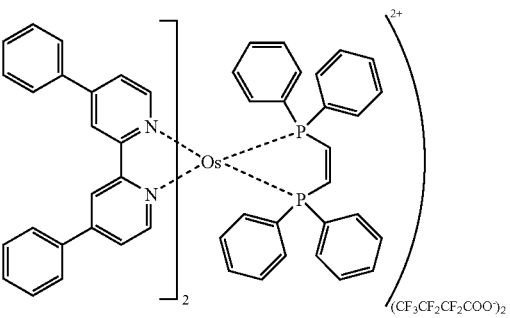

(Emission Host)

An emission host (also referred to as a host) means the compound of which the mixing ratio (in weight) is largest in the emission layer containing two or more compounds, and other compound is called as a dopant compound (also referred to as a dopant). For example, when an emission layer is constituted from two kinds of compound, namely, Compound A and Compound B, and the mixing ratio is A:B=10:90, then, Compound A is the dopant compound and Compound B is the host compound. Furthermore, when an emission layer is constituted from three kinds of compounds, namely, Compound A, Compound B, and Compound C, and the mixing ratio is A:B:C=5:10:85, then, compound A and a compound B are dopant compounds, and Compound C is the host compound.

The emission host of the present invention is preferably a compound having a shorter wavelength O-O band of phosphorescence than that of the emission dopant used together with the emission host. When the emission dopant exhibits a wavelength of the O-O band of 480 nm or less, the emission host preferably exhibits a wavelength of the O-O band of phosphorescence of 450 nm or less.

The structure of the emission host of the present invention is not specifically limited, however, preferable is a compound having a structure of, for example, a carbazole derivative, a triarylamine derivative, an aromatic borane derivative, a nitrogen-containing heterocyclic compound, a thiophene derivative, a furan derivative, or an oligoarylene compound, as well as exhibiting a wavelength of the O-O band of phosphorescence of 450 nm or less.

The emission host of the present invention may be a low molecular weight compound, a polymer compound having a repeat unit, or a low molecular weight compound having a polymerizable group like a vinyl group or an epoxy group (vapor-deposition-polymerizable emission host).

The emission host is preferably a compound having a hole transport ability, an electronic transport ability and a higher Tg (glass transition temperature), while preventing a shift of emission wavelength toward a long wavelength region.

As specific examples of an emission host, preferable is the compounds described in the following Patent Documents: for example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

Next, the constitution of a typical organic EL element will be described.

<<Composition Layer of Organic EL Element>>

The constituting layers of the organic EL element of the present invention will be described.

Preferable examples of a specific layer constitution of the organic EL of the present invention will be shown below, however, the present invention is not limited thereto.

(i) Anode/Emission layer/Electron transport layer/Cathode
(ii) Anode/Hole transport layer/Emission layer/Electron transport layer/Cathode
(iii) Anode/Hole transport layer/Emission layer/Hole blocking layer/Electron transport layer/Cathode
(iV) Anode/Hole transport layer/Emission layer/Hole blocking layer/Electron transport layer/Cathode buffer layer/Cathode
(v) Anode/Anode buffer layer/Hole transport layer/Emission layer/Hole blocking layer/Electron transport layer/Cathode buffer layer/Cathode <<Emission Layer>>

In the present invention, it is preferable that the platinum complex of the present invention or an ortho-metallated complex used as the platinum complexes is used, however, besides those, above known emission hosts and emission dopants may be used together with those.

In order to improve the effect of the present invention (enhancements in luminance and in emission life), it is preferable that the emission layer contains the compound represented by the above-mentioned Formula (10) or the above-mentioned Formula (11). These compounds are preferably used as an emission host in the emission layer.

<<Compounds Represented by Formula (10)>>

Examples of a substituent represented by $R_1$-$R_4$ in Formula (10) include: alkyl groups (for example, a methyl group, an ethyl group, a propyl group, an isopropyl group, a tert-butyl, a pentyl group, a hexyl group, an octyl group, a dodecyl group, a tridecyl group, a tetradecyl group and a pentadecyl group); cycloalkyl groups (for example, a cyclopentyl group and a cyclohexyl group); alkenyl groups (for example, a vinyl group and an allyl group); alkynyl groups (for example, an ethynyl group and, a propargyl group); aryl groups (for example, a phenyl group and a naphthyl group); heteroaryl groups (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolyl group and a phthalazyl group); heterocycle groups (for example, a pyrrolidyl group and an imidazolidyl group, a morpholyl group and oxazolidyl group); alkoxy groups (for example, a methoxy group, an ethoxy group, a propyloxy group, a pentyloxy group, a hexyloxy group, an octyloxy group and a dodecyloxy group); cycloalkoxy groups (for example, a cyclopentyloxy group and a cyclohexyloxy group); aryloxy groups (for example, a phenoxy group and a naphthyloxy group); alkylthio groups (for example, a methylthio group, an ethylthio group, a propylthio group, a pentylthio group, a hexylthio group, an octylthio group and a dodecyl thio group); cycloalkylthio groups (for example, a cyclopentylthio group and a cyclohexylthio group); arylthio groups (for example, a phenylthio group and a naphthylthio group); alkoxycarbonyl groups (for example, a methyloxycarbonyl group, an ethyloxycarbonyl group, a butyloxycarbonyl group, an octyloxycarbonyl group and a dodecyl oxycarbonyl group); aryloxycarbonyl groups (for example, a phenyloxycarbonyl group and a naphthyloxycarbonyl group); sulfamoyl groups (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group and 2-pyridylaminosulfonyl group); acyl groups (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group and a pyridylcarbonyl group); acyloxy groups (for example, an acetyloxy group, an ethylcarbonyloxy group, and a butylcarbonyloxy group, an octylcarbonyloxy group, a dodecylcarbonyloxy group and a phenylcarbonyloxy group); amide groups (for example, a methylcarbonylamino group and an ethylcarbonylamino group, a dimethylcarbonylamino group, a propylcarbonylamino group, a pentylcarbonylamino group, a cyclohexylcarbonylamino group, 2-ethylhexylcarbonylamino group, an octylcarbonylamino group, a dodecylcarbonylamino group, a phenylcarbonylamino group and a naphthylcarbonylamino group); carbamoyl groups (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, 2-ethylhexylaminocarbonyl group, a dodecylaminocarbonyl group, a phenylaminocarbonylgroup, a naphthylaminocarbonyl and a 2-pyridylaminocarbonyl group); ureido groups (for example, a methylureido group, an ethylureido group, a pentylureido group, a cyclohexylureido group, an octylureido group, a dodecylureido group, a phenylureido group, a naphthylureido group and 2-pyridyl amino ureido group); sulfinyl groups (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group and 2-pyridylsulfinyl group); alkylsulfonyl groups (for example, a methylsultonyl group, an ethylsulfonyl group, a butylsulfonyl group, a cyclohexylsulfonyl group, a 2-ethylhexylsulfonyl group and a dodecylsulfonyl group); arylsulfonyl groups (for example, a phenylsulfonyl group, a naphthylsulfonyl group and a 2-pyridylsulfonyl group); amino groups (for example, an amino group, an ethylamino group, a dimethylamino group, a butyl amino group, a cyclopentylamino group, a 2-ethylhexylamino group, a dodecylamino group, an anilino group, a naphthylamino group and a 2-pyridylamino group); halogen atoms (for example, a fluorine atom, a chlorine atom and a bromine atom); fluorohydrocarbon groups (for example, a fluoromethyl group, a trifluoromethyl group, a pentafluoroethyl group and a pentafluorophenyl group); and a cyano group; a nitro group; a hydroxyl group; a mercapto group; and silyl groups (for example, a trimethylsilyl group, a triisopropyl silyl group, a triphenylsilyl group and a phenyldiethylsilyl group).

Each of these substituents may further be substituted with an above-mentioned substituent. A plurality of these groups may be combined to form a ring.

Examples of an arylene group represented by Ar1 or Ar2 in Formula (10) include: an o-phenylene group, a m-phenylene group, a p-phenylene group, a naphthalenediyl group, an anthracenediyl group, a naphthacenediyl group, a pyrenediyl group, a naphthylnaphthalenediyl group, a biphenyldiyl group (for example, a 3,3'-biphenyldiyl group and 3,6-biphenyldiyl group), a terphenyldiyl group, a quaterphenyldiyl group, a kinkphenyldiyl group, a sexiphenyldiyl group, a septiphenyldiyl group, an octiphenyldiyl group, the noviphenyldiyl group and a deciphenyldiyl group. Moreover, each of the above-mentioned arylene groups may further have a substituent represented by each of $R_1$-$R_4$.

Examples of a divalent aromatic heterocycle group represented by $Ar_1$ or $Ar_2$ in the above-mentioned Formula (10) include: a furan ring, a thiophene ring, a pyridine ring, a pyridazine ring, a pyrimidine ring, a pyrazine ring, a triazine ring, a benzimidazole ring, an oxydiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring, and a divalent group derived from a carboline ring of which one of carbon atoms of a hydrocarbon ring constituting the carboline ring is replaced with a nitrogen atom. Moreover, each of the above-mentioned divalent aromatic heterocycle groups may further have a substituent represented by each of $R_1$-$R_4$.

Examples of a divalent linking group represented by $L_{01}$ in the above-mentioned Formula (10) include: hydrocarbon groups such as an alkylene group (for example, a methylene group, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, a nonamethylene group, a decamethylene group, a undecamethylene group, a dodecamethylene group, a cyclohexylene group (for example, 1,6-cyclohexanediyl group) and a cyclopentylene group (for example, 1,5-cyclopentanediyl group)), an alkenylene group (for example, a vinylene group and a propenylene group), an alkynylene group (for example, an ethynulene group and a 3-pentinulene group) and a arylene group; and heteroatom-containing groups (for example, a divalent group containing a chalcogen atom such as —O— or —S—, and a —N(R)— group in which R represents a hydrogen atom or an alkyl group, where the alkyl group is the same as that defined by each of $R_1$-$R_4$ in Formula (10).

In each of the above-mentioned alkylene group, an alkenylene group, an alkynylene group, and an arylene group, one of the carbon atoms which constitute a divalent linking group may be replaced with a chalcogen atom (for example, oxygen or sulfur) or an above-mentioned —N(R)— group. As a divalent linking group represented by $L_1$, for example, a divalent group having a heterocycle is used, examples of which include: an oxazole diyl group, a pyrimidinediyl group, a pyridazinediyl group, a pyranediyl group, a pyrrolinediyl group, an imidazolinediyl group, an imidazolidinediyl group, a pyrazolidine diyl group, a pyrazolinediyl group, a piperidinediyl group, a piperazinediyl group, a morpholinediyl group and a quinuclidinediyl group. Also included is a divalent linking group derived from a compound having an aromatic heterocycle (also referred to as a heteroaryl compound), for example, a thiophene-2,5-diyl group and a pyrazine-2,3-diyl group.

Further, also included is a group in which a linkage through a heteroatom is included, for example, an alkylimino group, a dialkylsilanediyl group and a diarylgermanediyl group.

By using an organic EL element material represented by Formula (10), an organic EL element exhibiting a higher emission efficiency is obtained, and, further, an organic EL element exhibiting a longer emission life is obtained.

<<Compounds Represented by Formula (11)>>

The substituent represented by each of $R_5$-$R_{16}$ is the same as the substituent defined by each of $R_1$-$R_4$ in Formula (10).

By using an organic EL element material represented by Formula (11), an organic EL element exhibiting a higher emission efficiency is obtained, and, further, an organic EL element exhibiting a longer emission life is obtained.

Specific examples of compounds represented by Formulae (10) and (11) will be shown below, however, the present invention is not limited thereto.

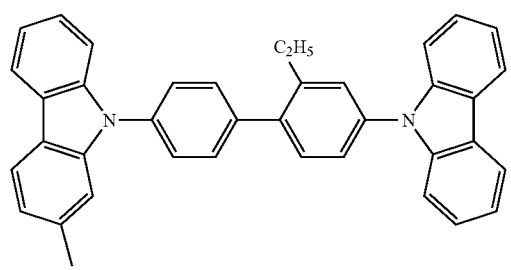

1

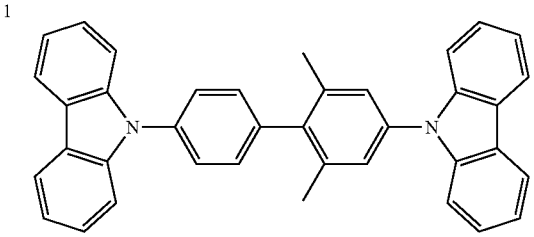

2

-continued
| 3 | 4 |
|---|---|
| 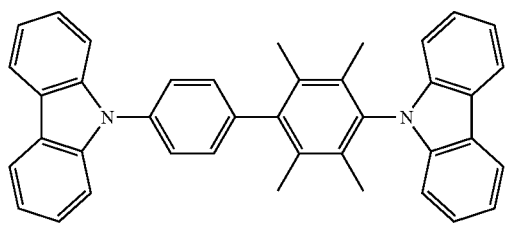 | 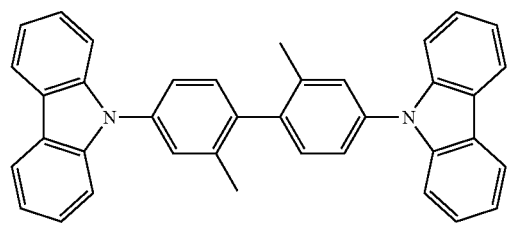 |
| 5 | 6 |
| 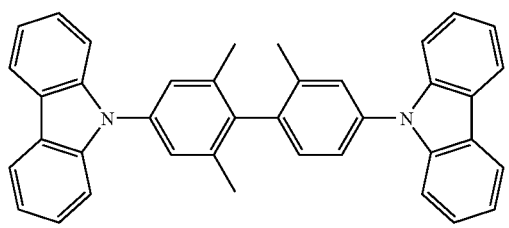 | 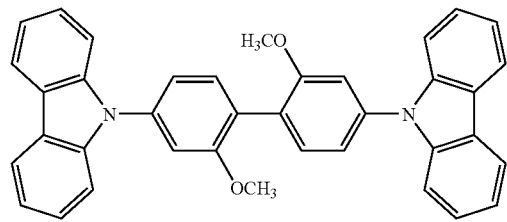 |
| 7 | 12 |
| 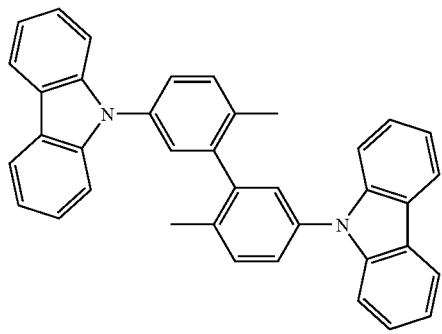 | 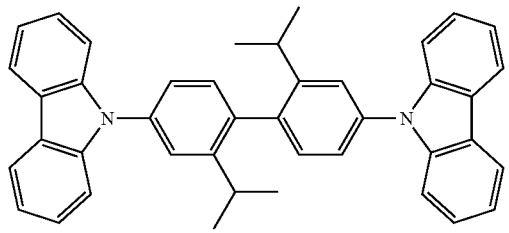 |
| 13 | 14 |
| 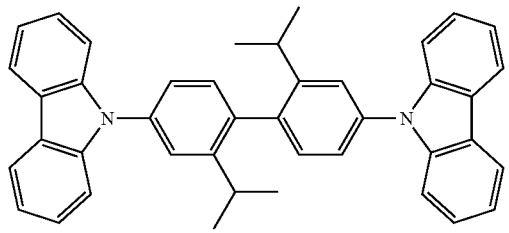 | 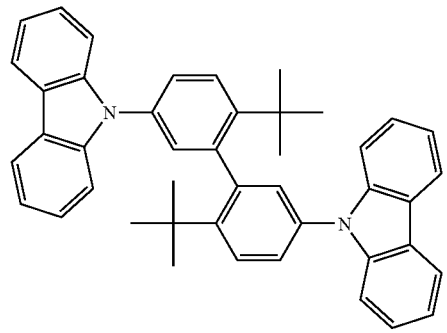 |
| 15 | 21 |
| 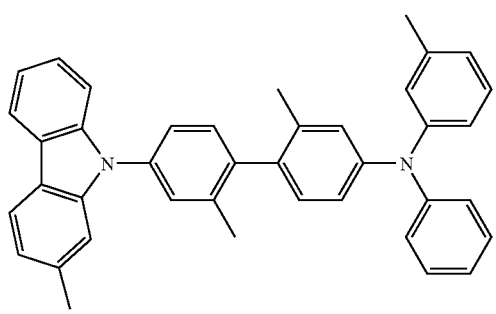 | 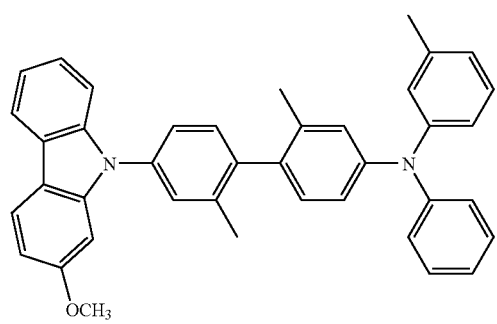 |

-continued
1-1
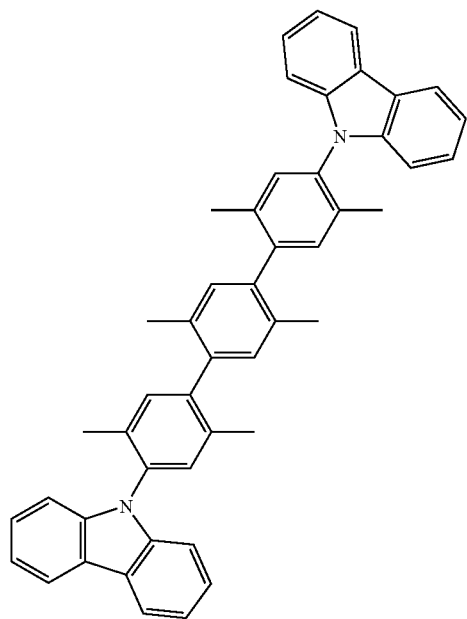
1-2
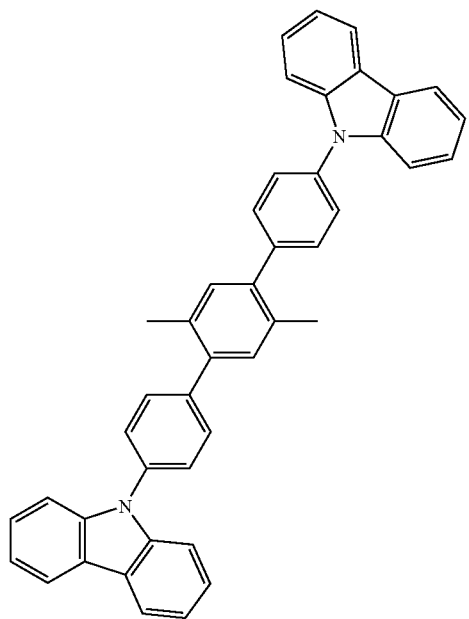
1-3
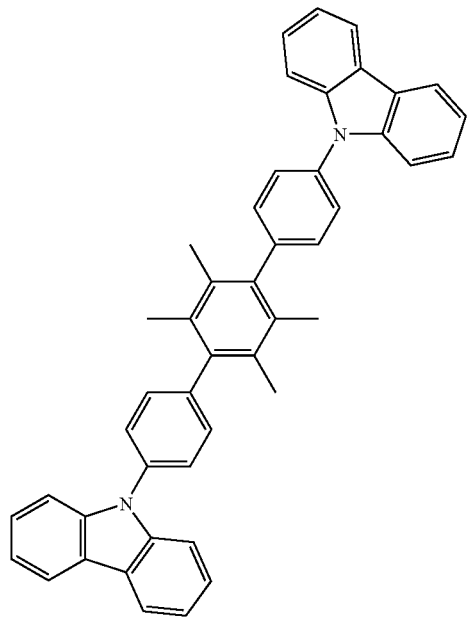
1-4
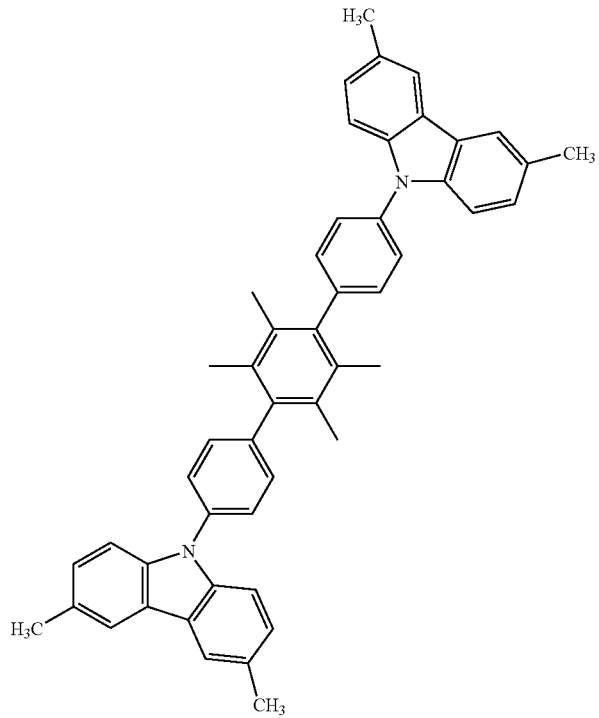

-continued
1-5
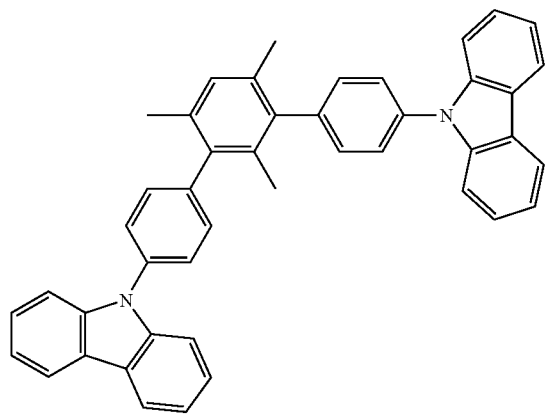
1-6
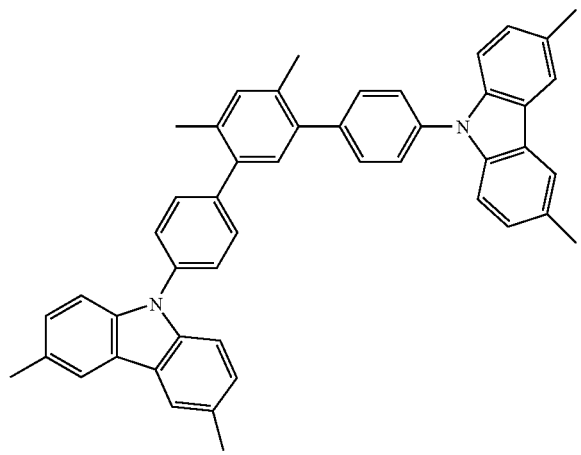
1-7
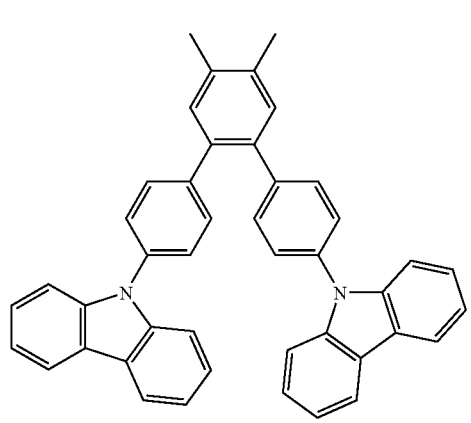
1-8
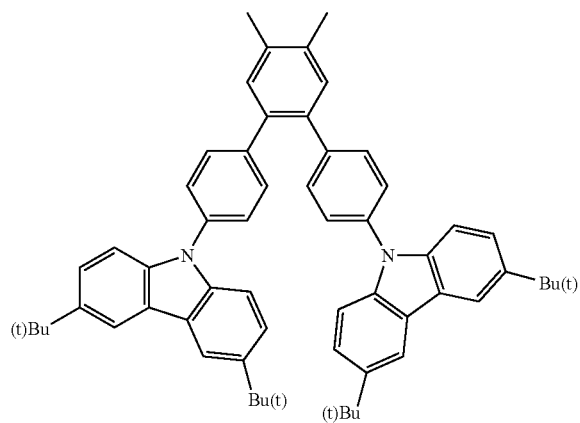
1-9
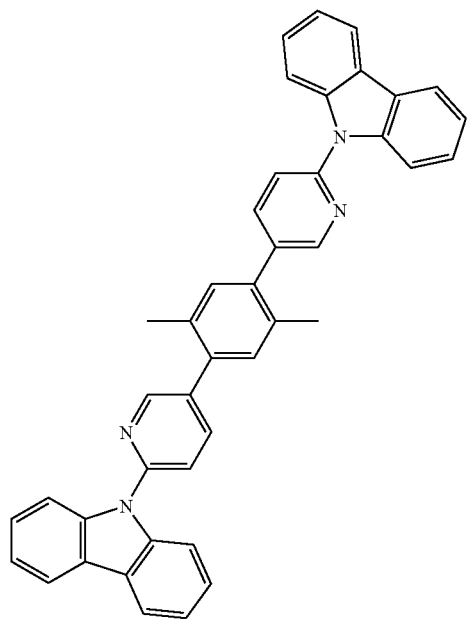
1-10
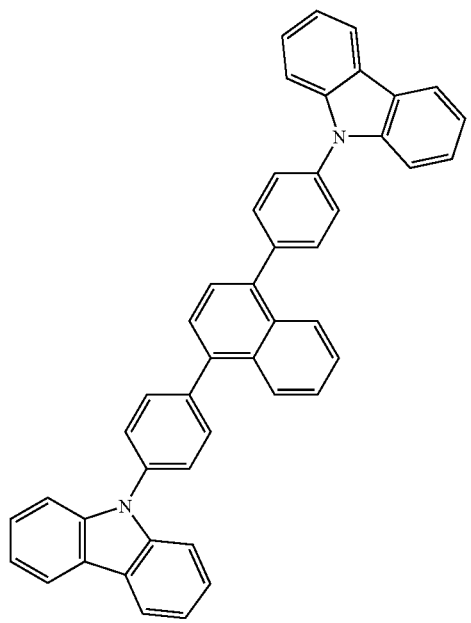

-continued
1-11
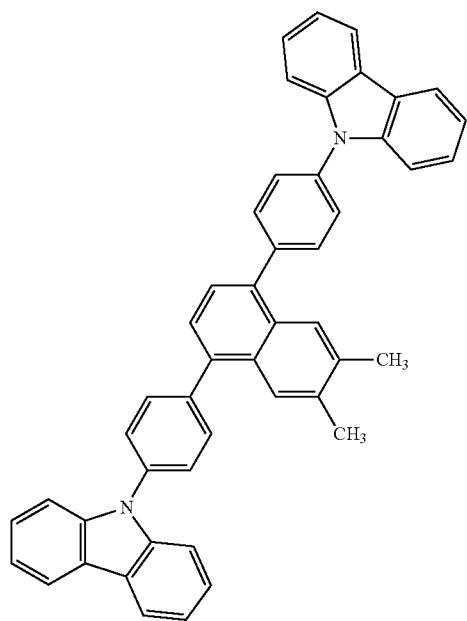
1-12
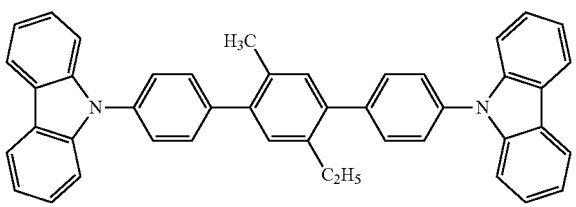
1-13
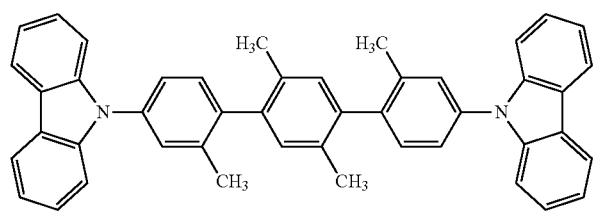
2-1
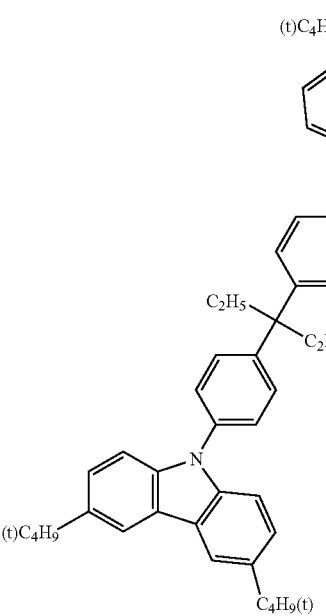

-continued
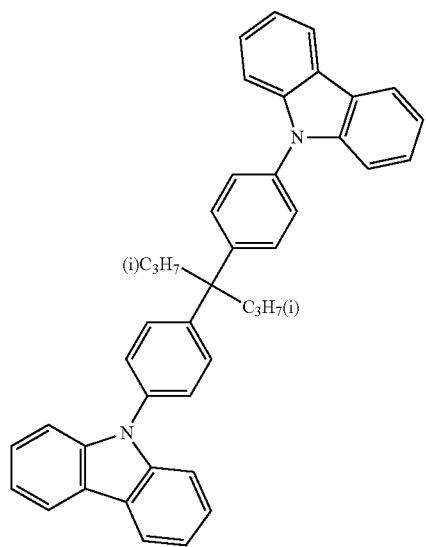
2-2
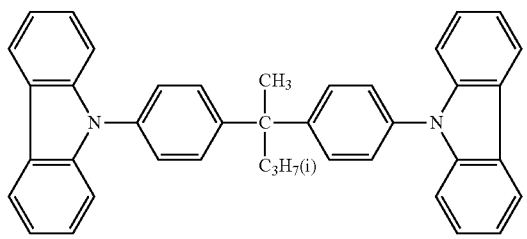
2-3
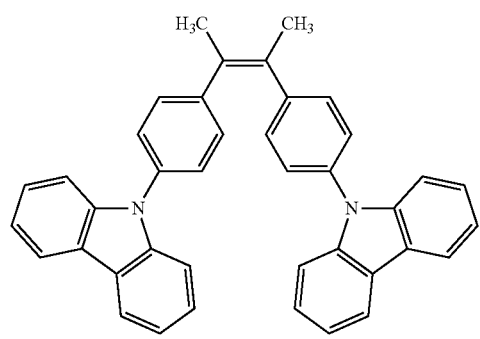
2-4
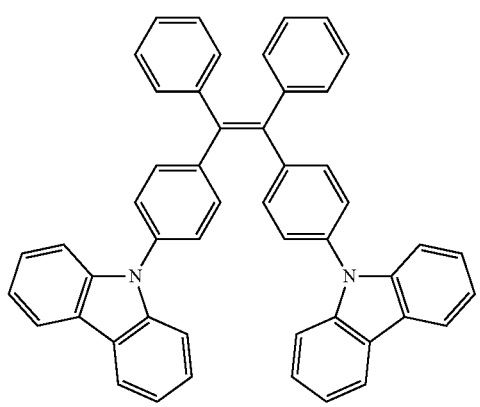
2-5
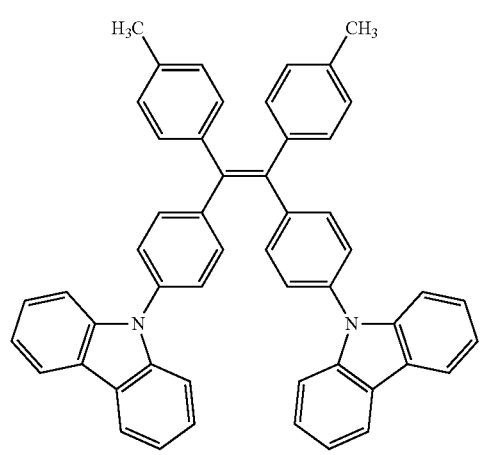
2-6
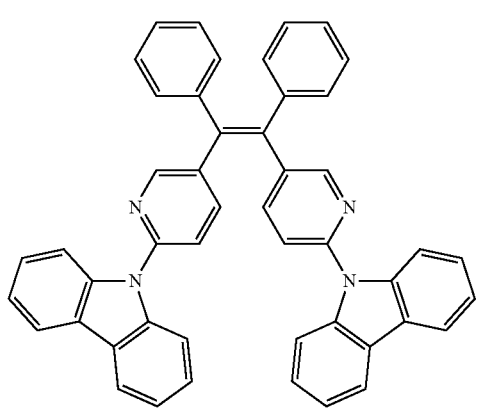
2-7

-continued
3-1
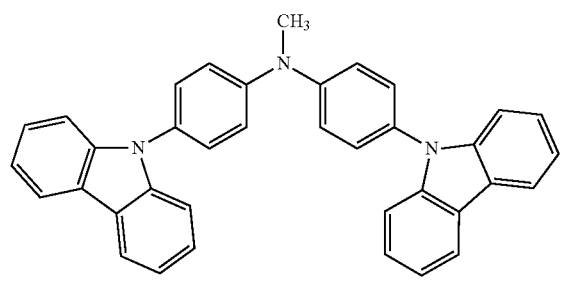
3-2
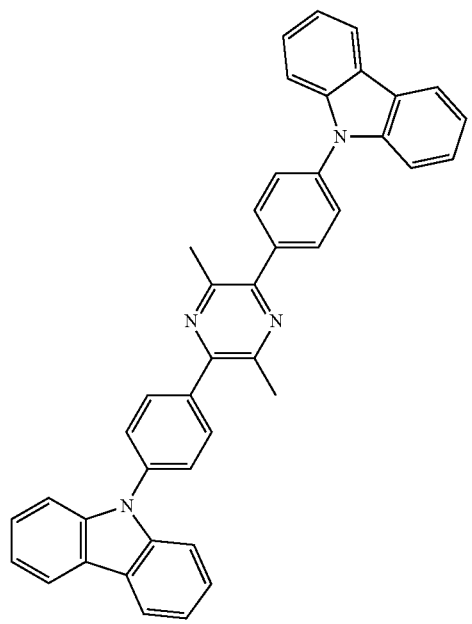
3-3
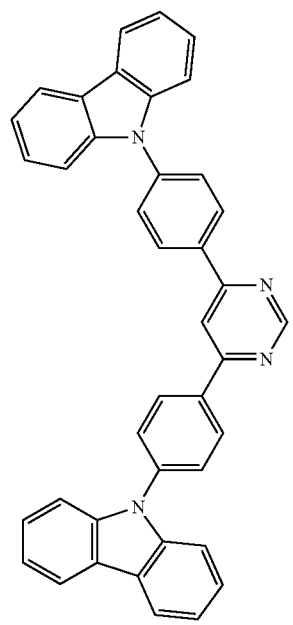
3-4
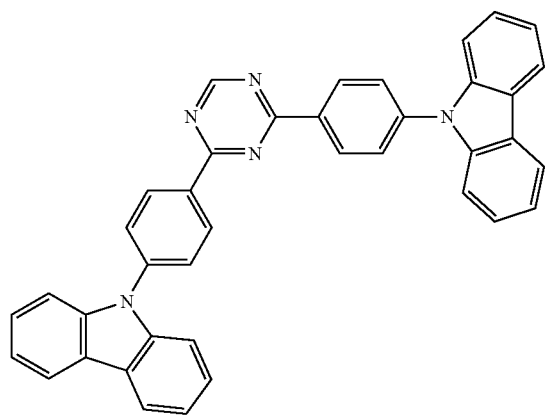

-continued
3-5
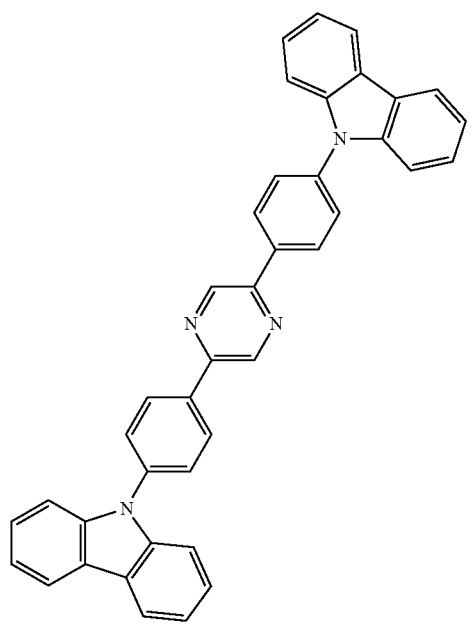
4-1
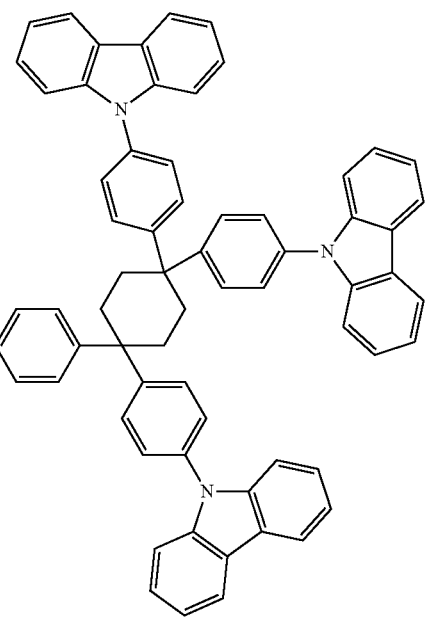
4-2
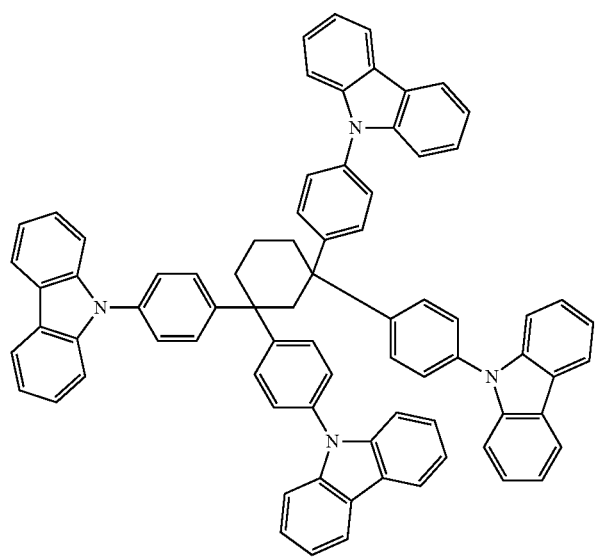
4-3
4-4
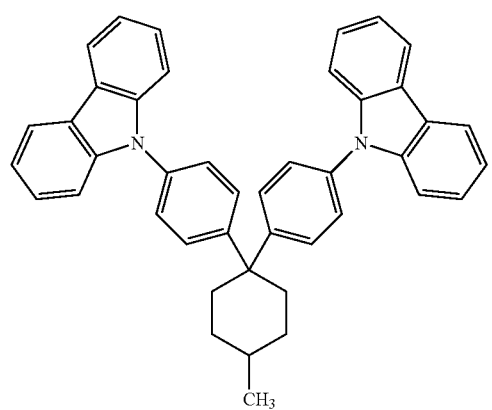
4-5
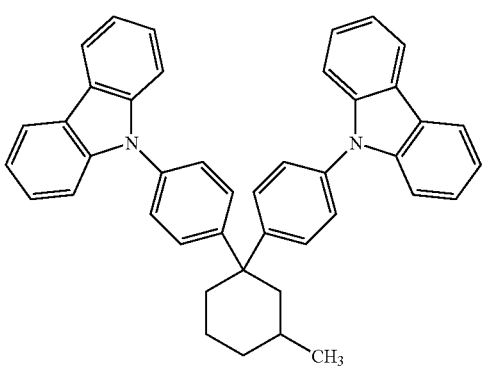

4-6
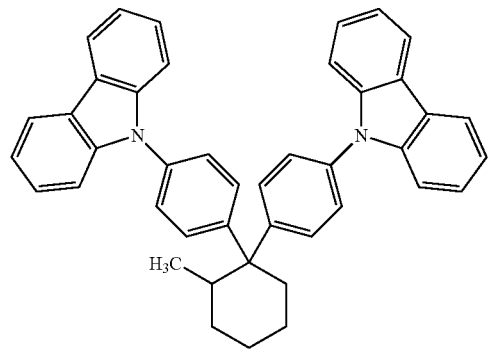
4-7
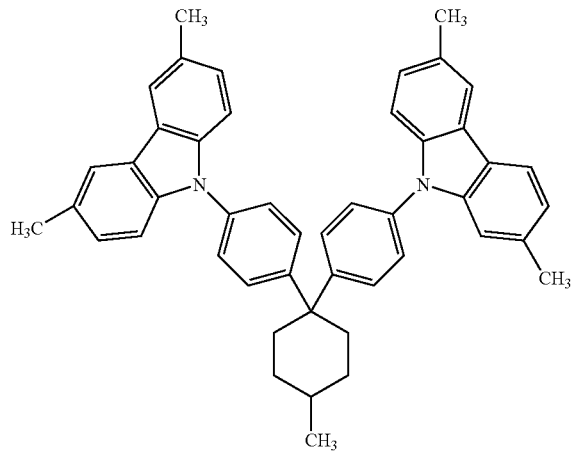
4-8
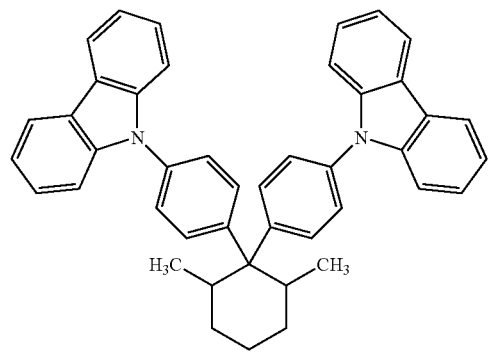
4-9
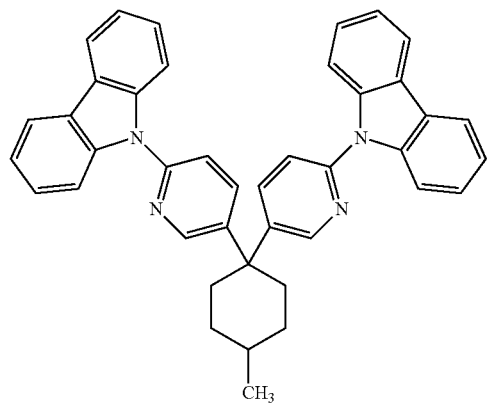
4-10
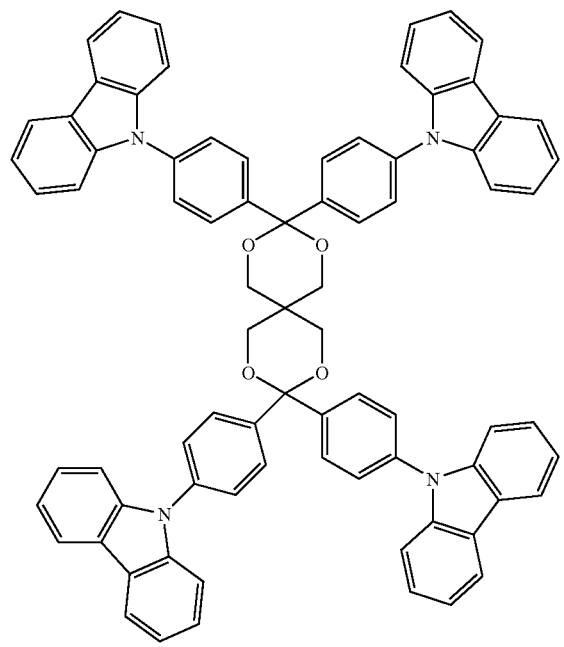
4-11

-continued
4-12
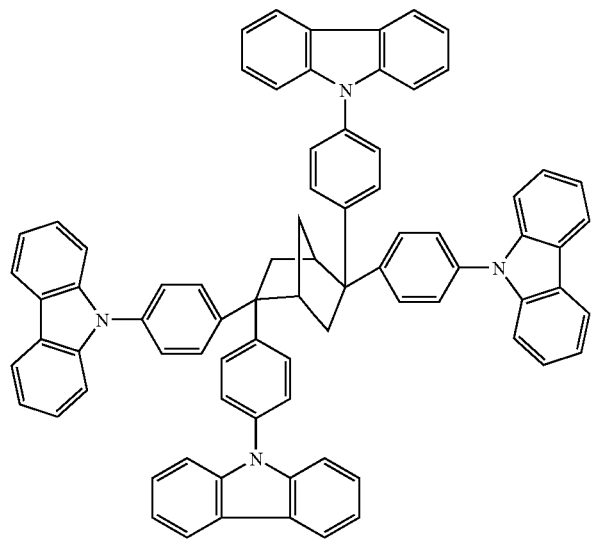
4-13
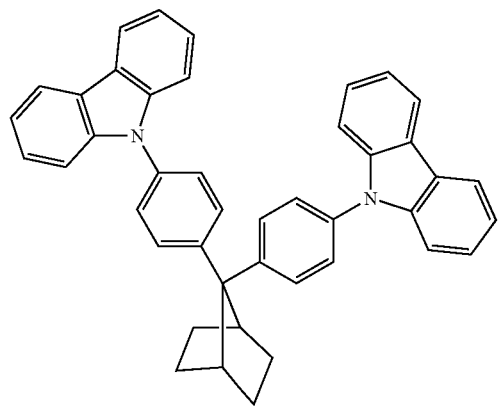
5-1
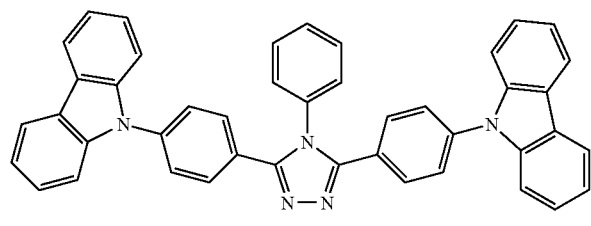
5-2
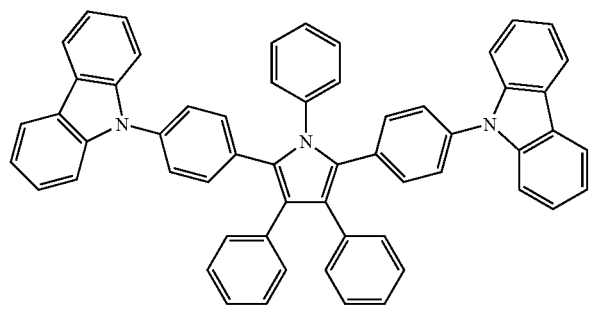
5-3 5-4
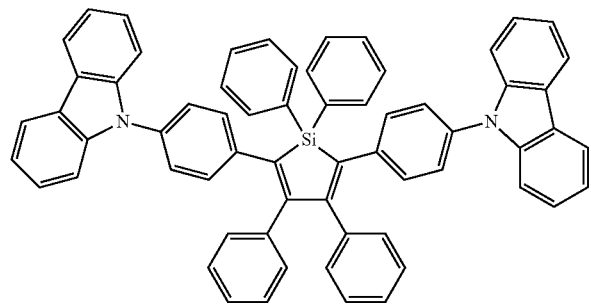
5-5 HA-1
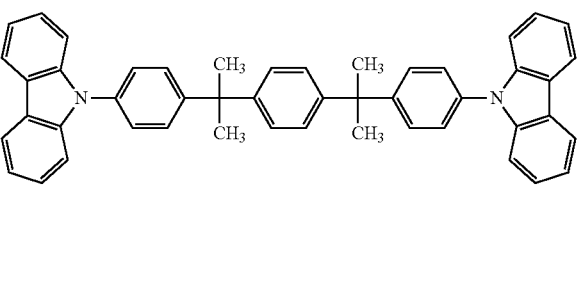

-continued
HA-2
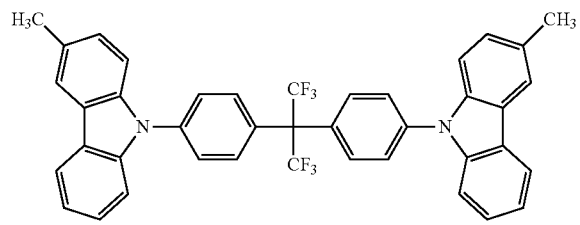
HA-3
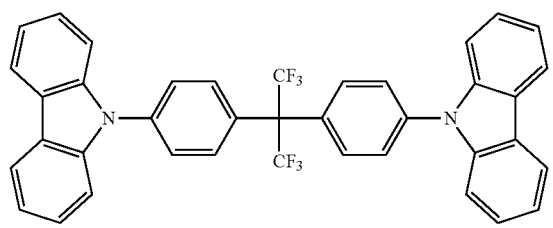
HA-4
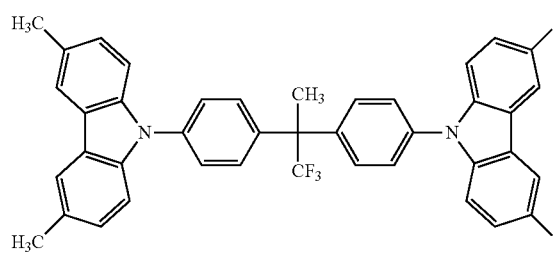
HA-5
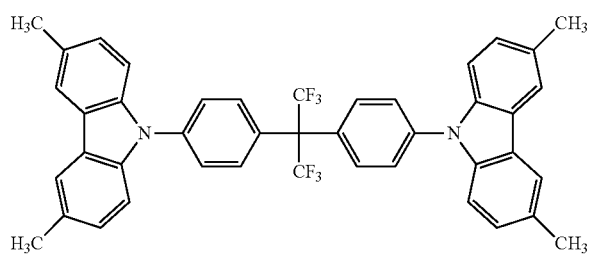
HA-6
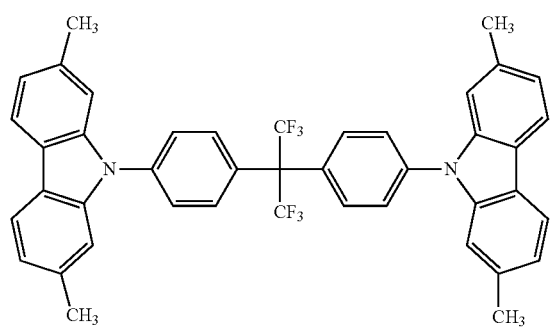
HA-7
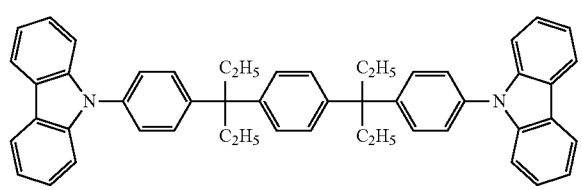
HA-8
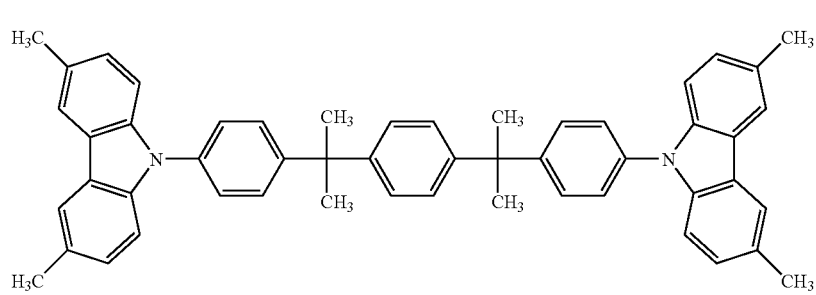
HA-9
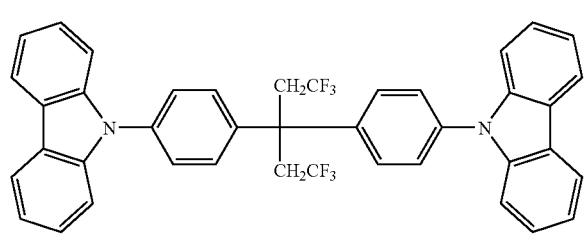

HA-10
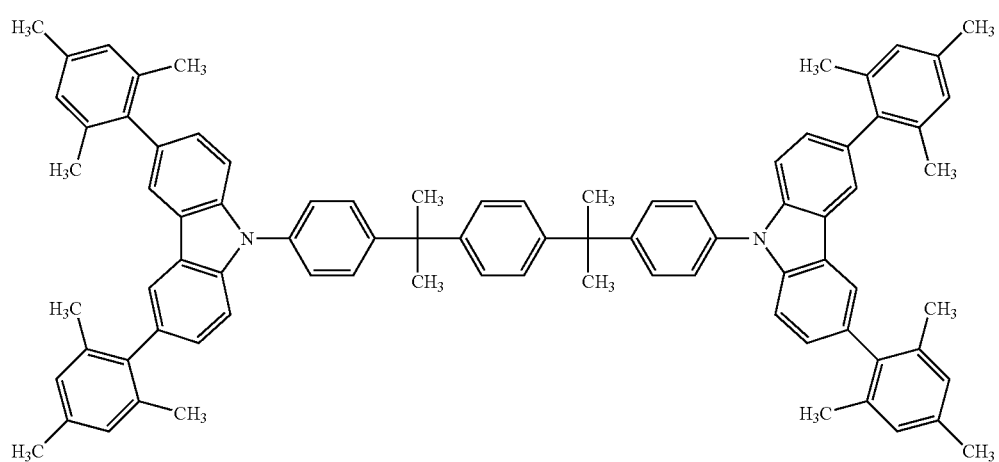
HA-11
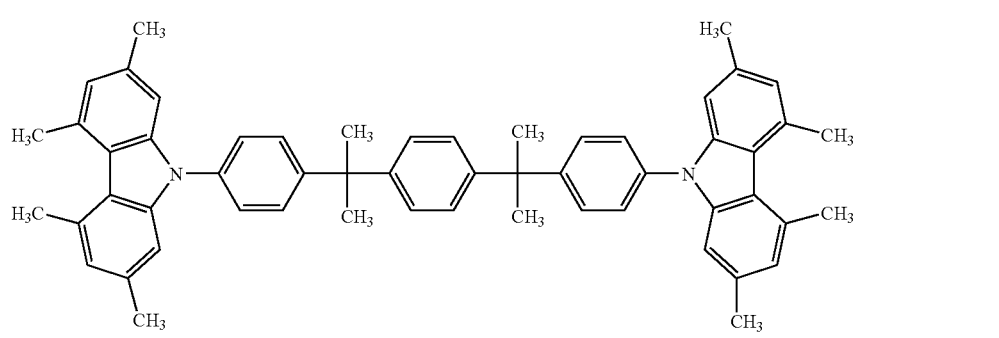
IA-1
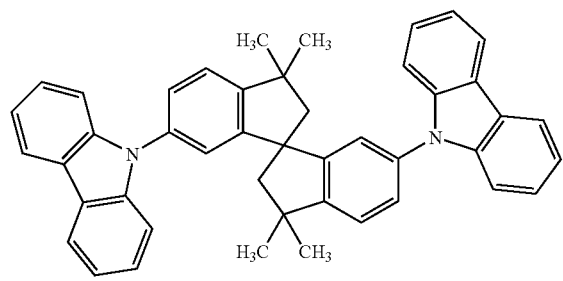
IA-2
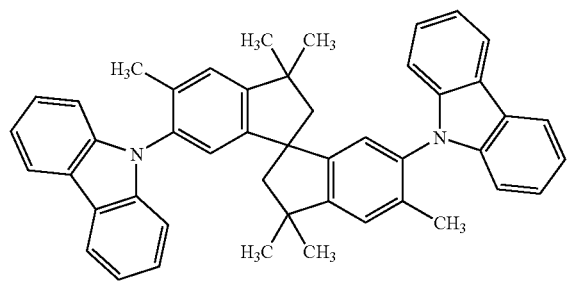
IA-3
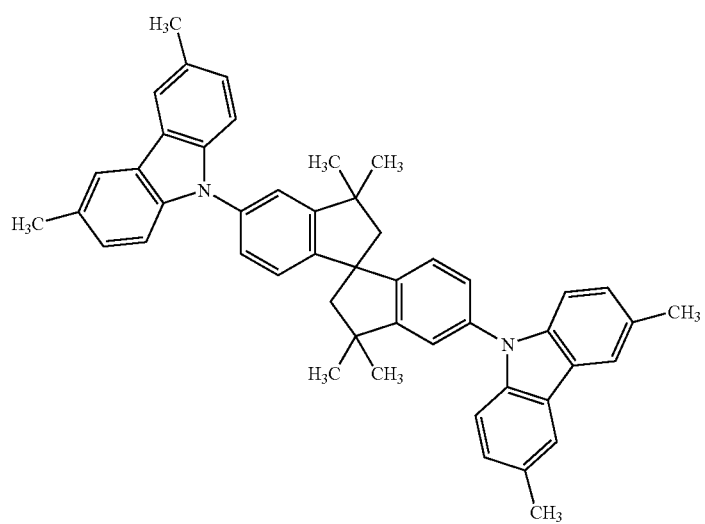

-continued
IA-4
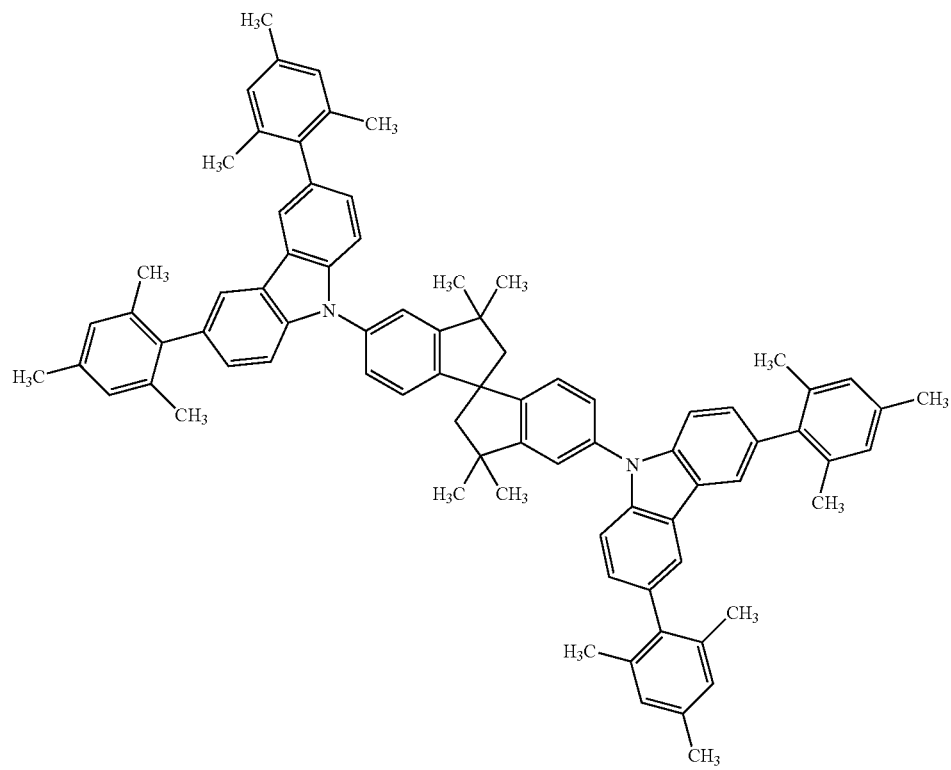
IA-5
IA-6
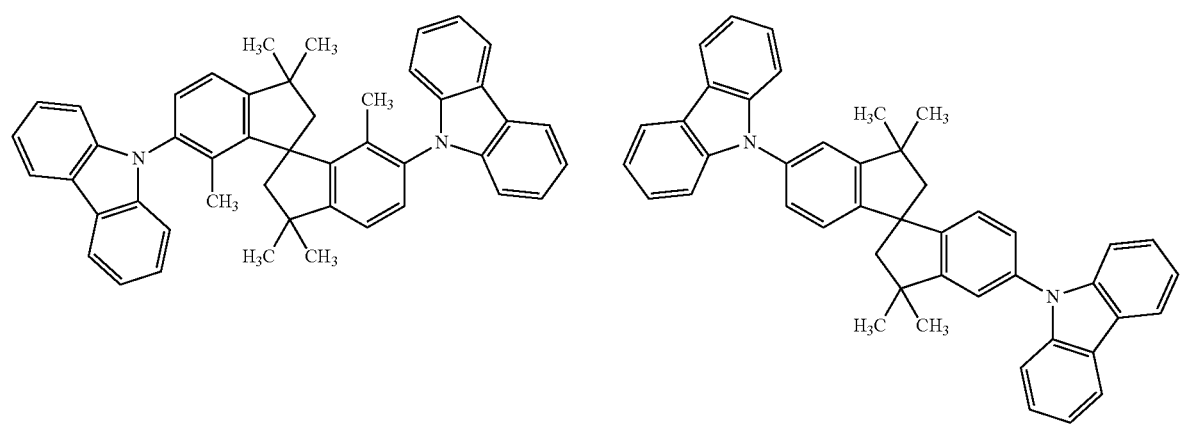
IA-7
IA-8
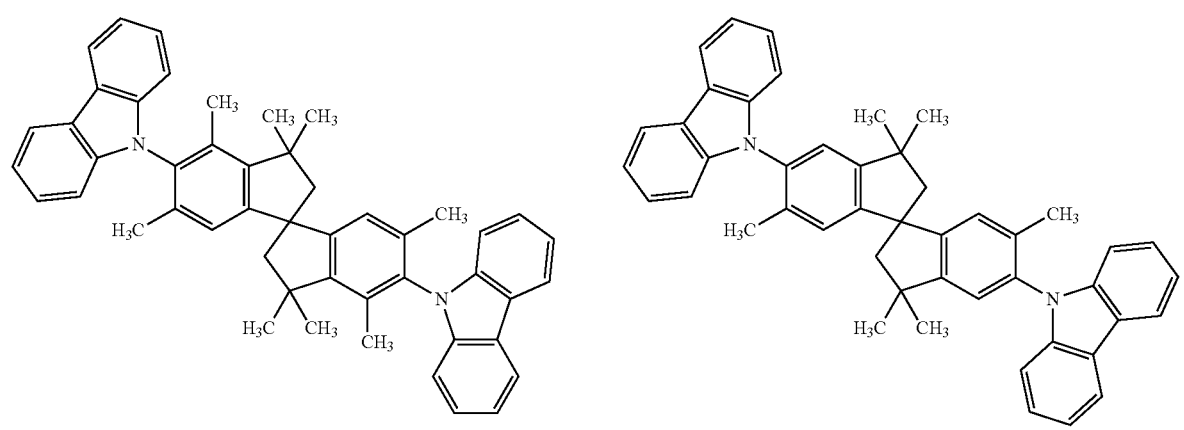

-continued
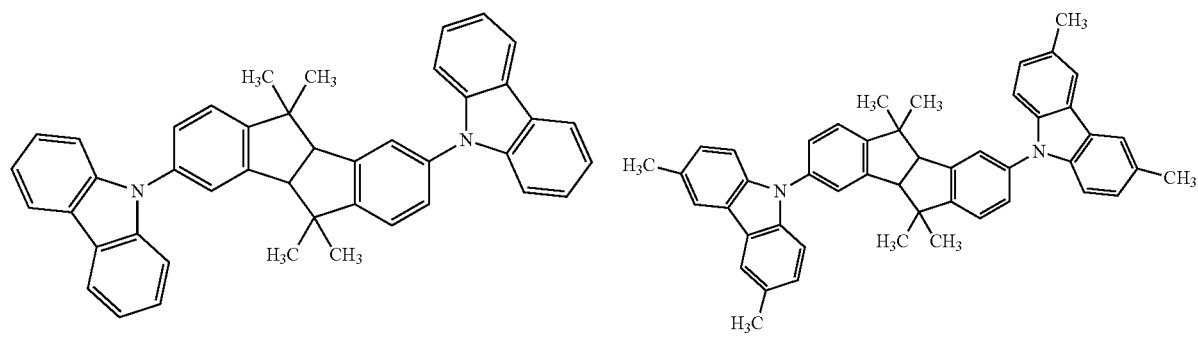
IA-9
IA-10
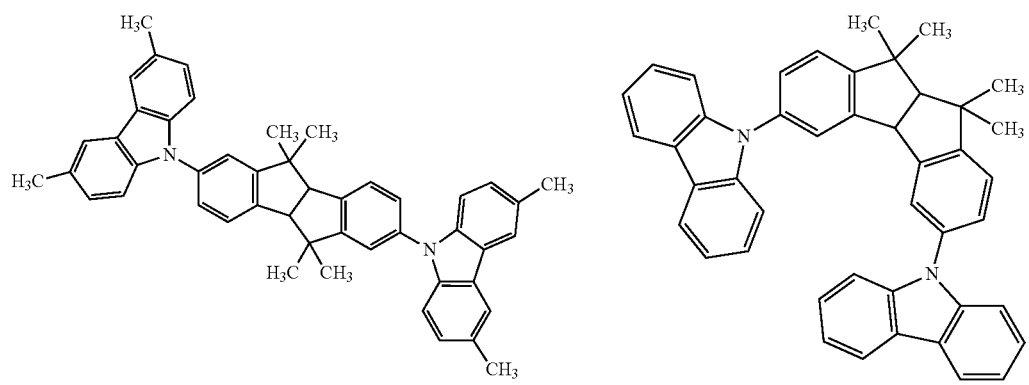
IA-11
IA-12
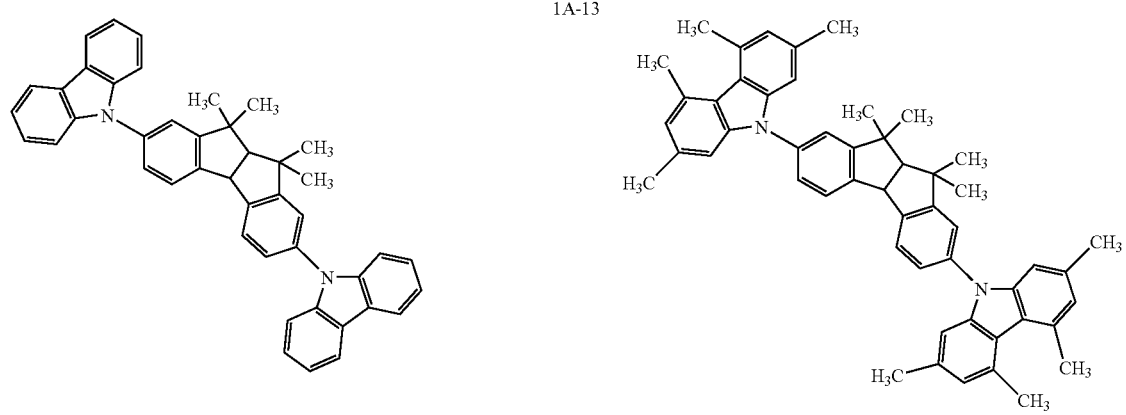
IA-13
IA-14
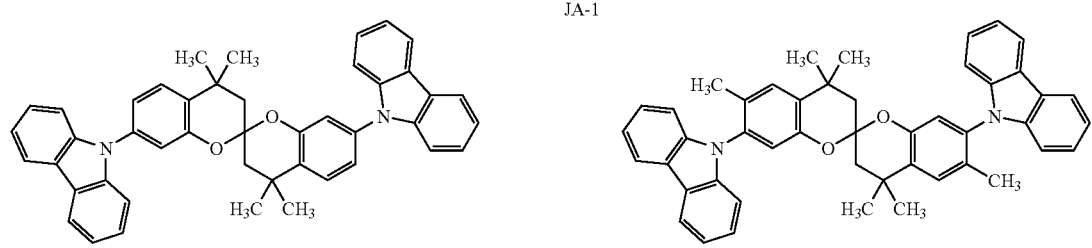
JA-1
JA-2

-continued
JA-3
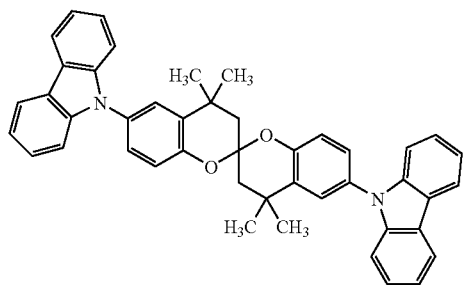
JA-4
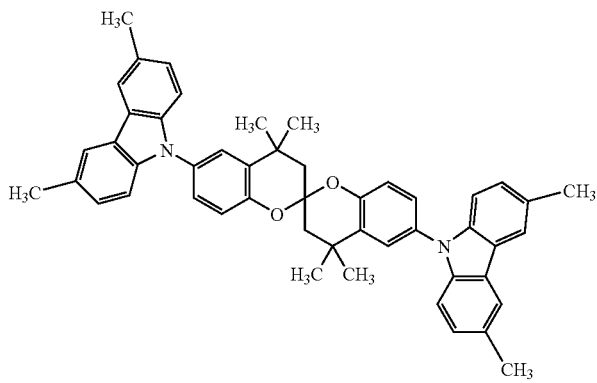
JA-5
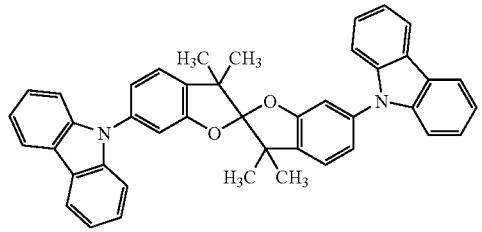
JA-6
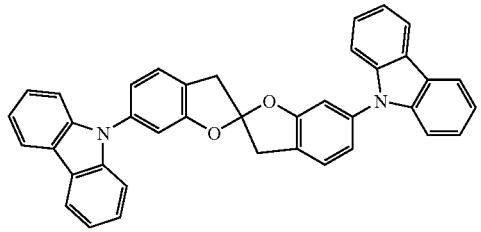
JA-7
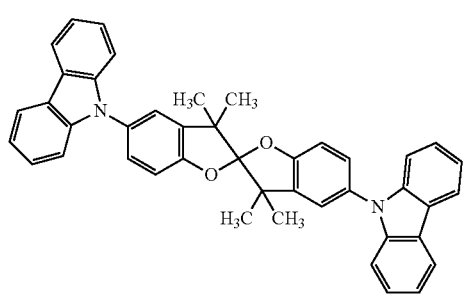
JA-8
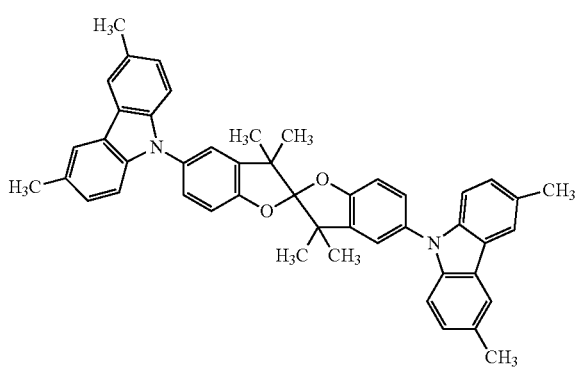
HC1
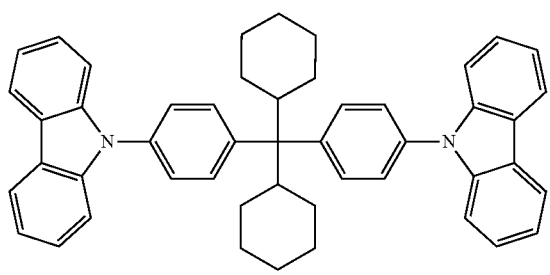
HC2
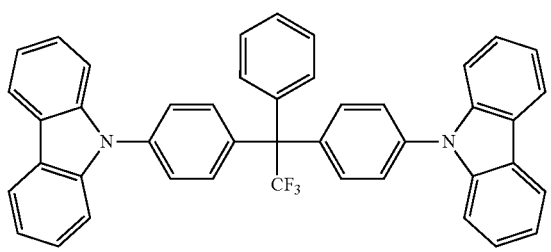
HC3
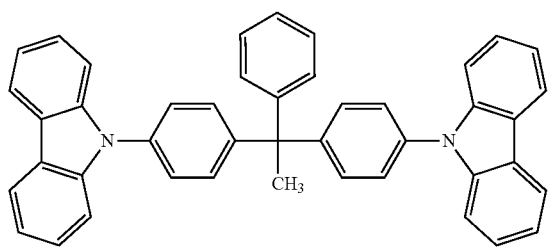
HC4
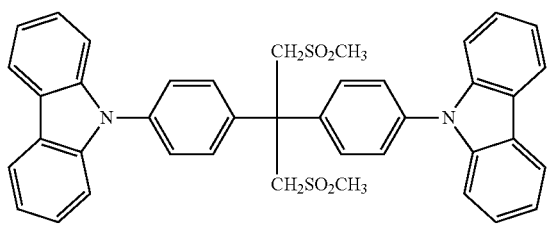

-continued
HC5
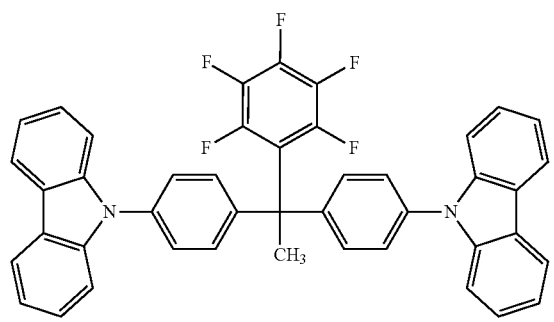
HC6
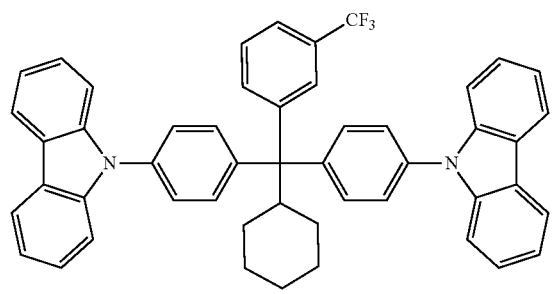
HC7
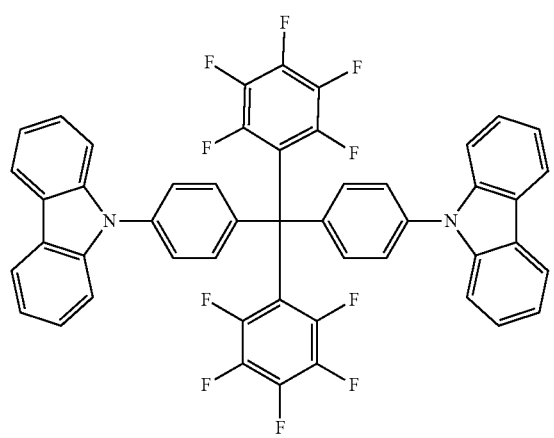
HC8
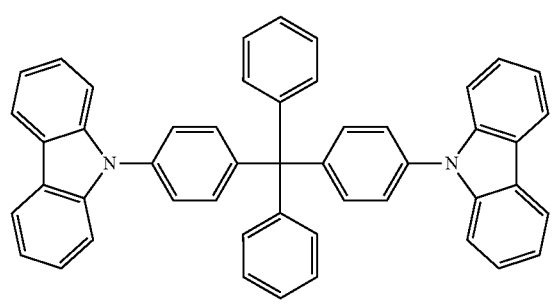
HC9
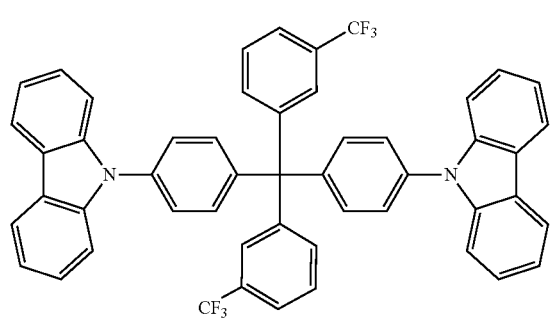
HC10
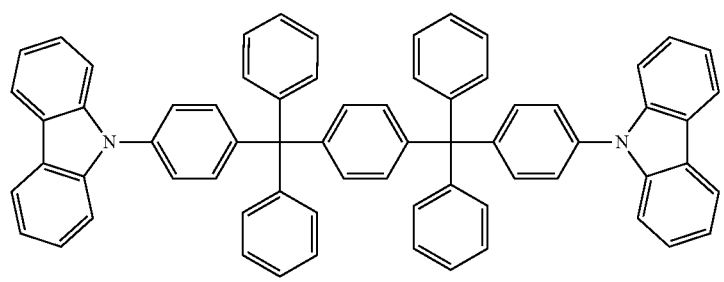

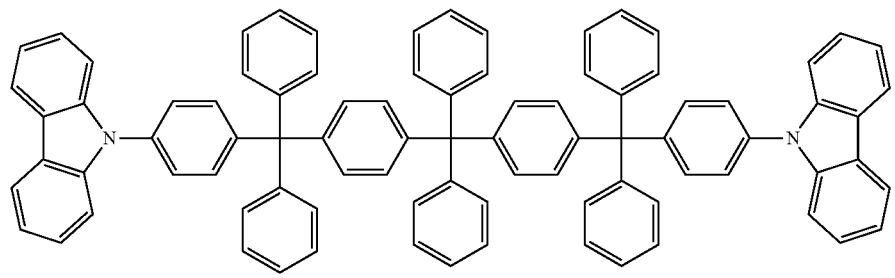

HC11

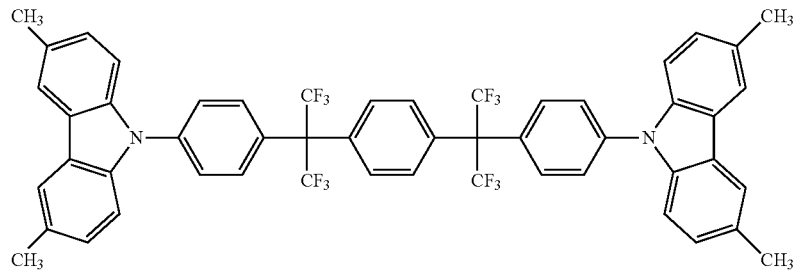

HC12

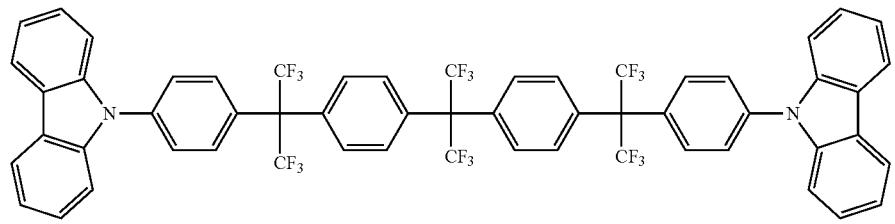

HC13

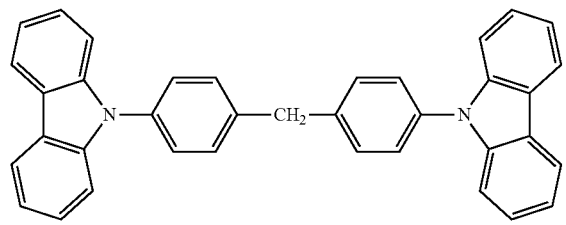

HC14

<<Carboline derivatives and Derivatives Having Carboline Related Ring>>

An organic EL element exhibiting a high emission efficiency and a long emission life is obtained by incorporating, in the emission layer, a carboline derivative or a derivative having a ring structure in which at least one of carbon atoms of a hydrocarbon ring constituting the carboline ring is replaced with a nitrogen atom.

Specific examples of a carboline derivative or a derivative having a ring structure in which at least one of carbon atoms of a hydrocarbon ring constituting the carboline ring is replaced with a nitrogen atom will be shown below, however, the present invention is not limited thereto.

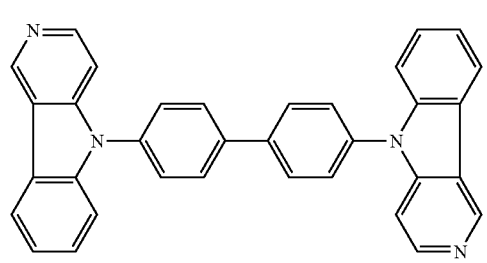

60

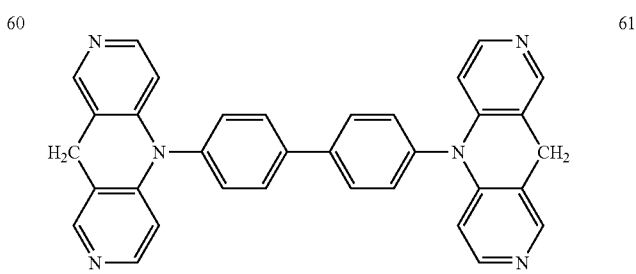

61

-continued
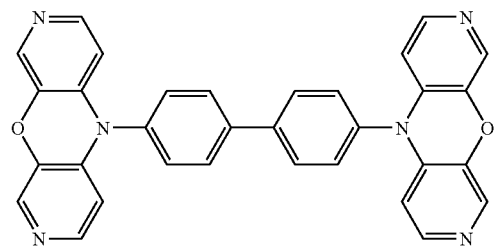
62
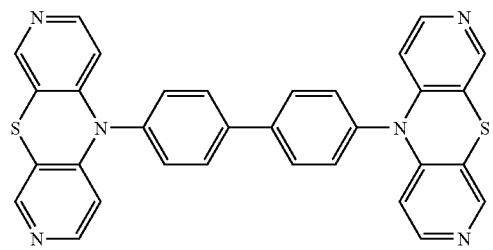
63
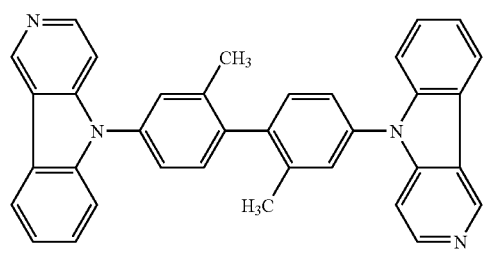
64
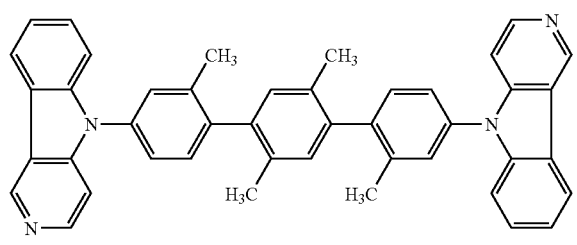
65
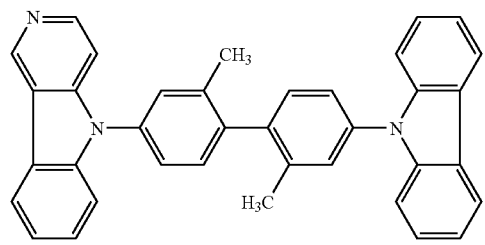
66
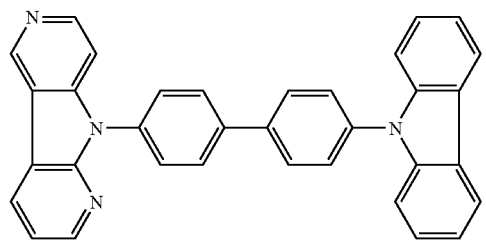
67
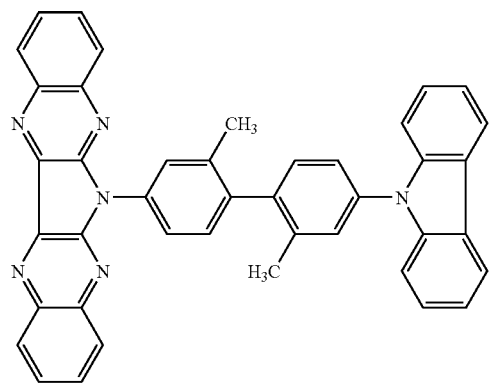
68
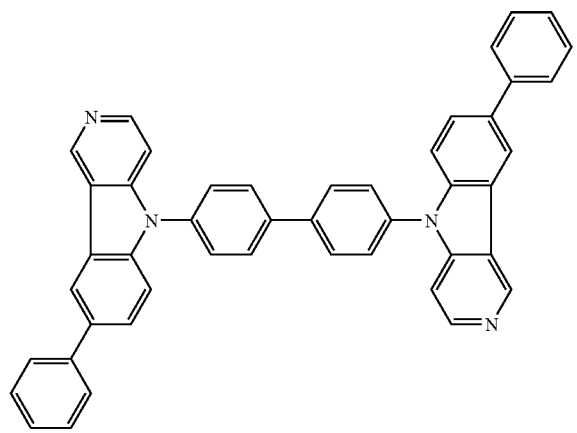
69

-continued
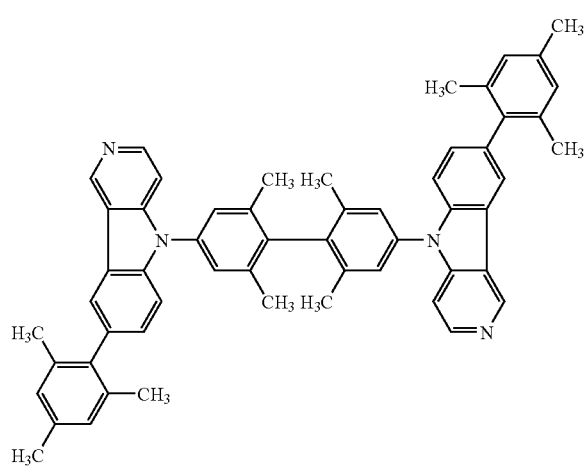
70
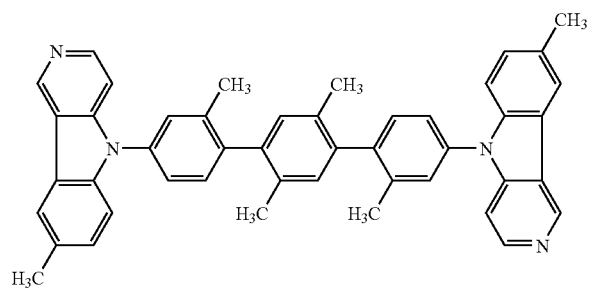
71
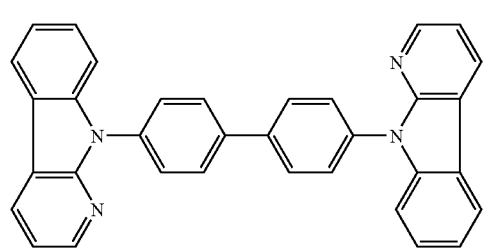
72
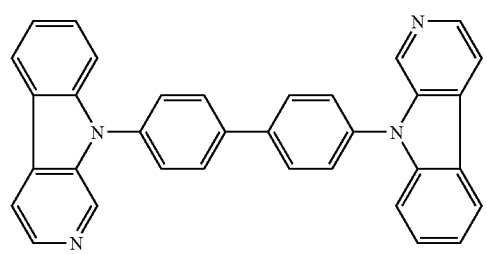
73
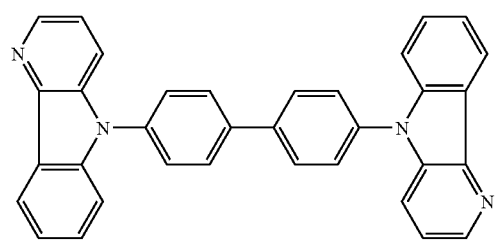
74
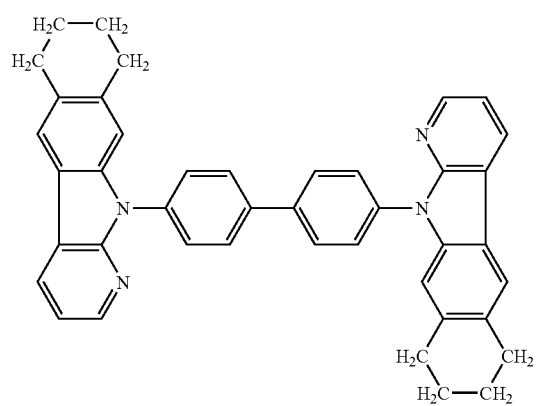
75
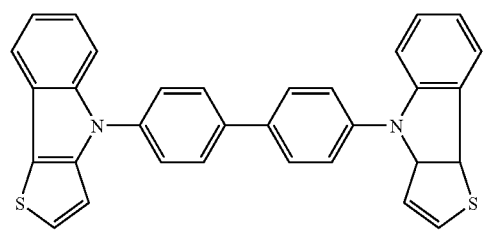
76
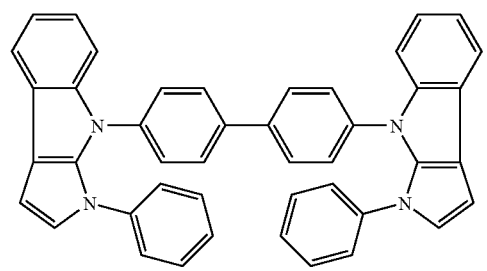
77

-continued
78
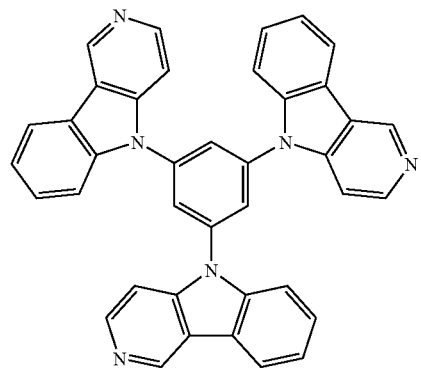
79
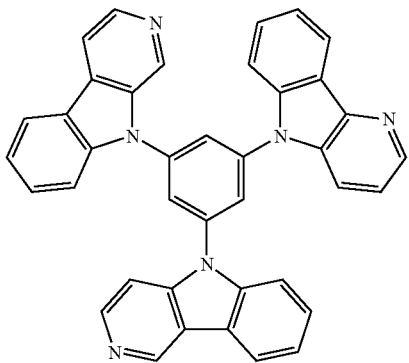
80
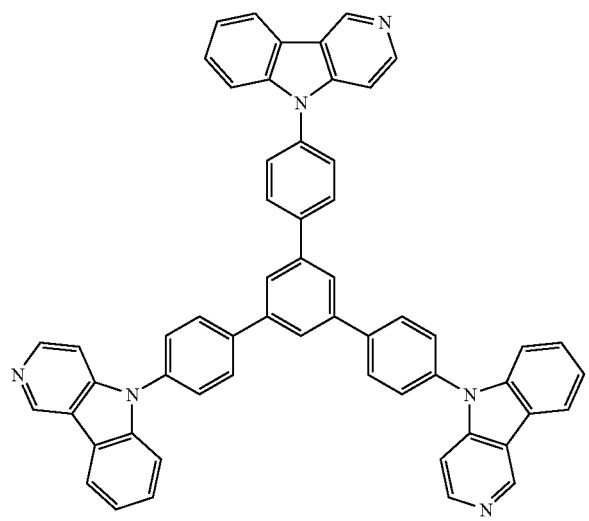
81
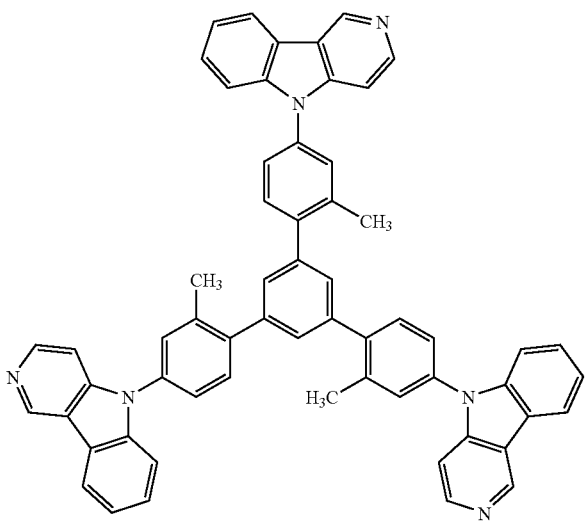
82
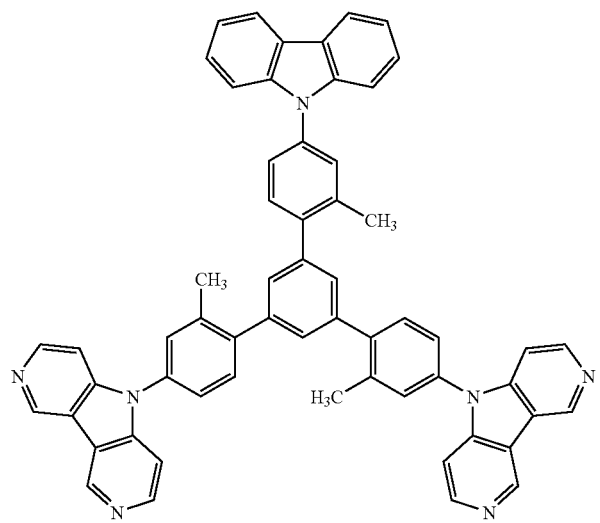
83
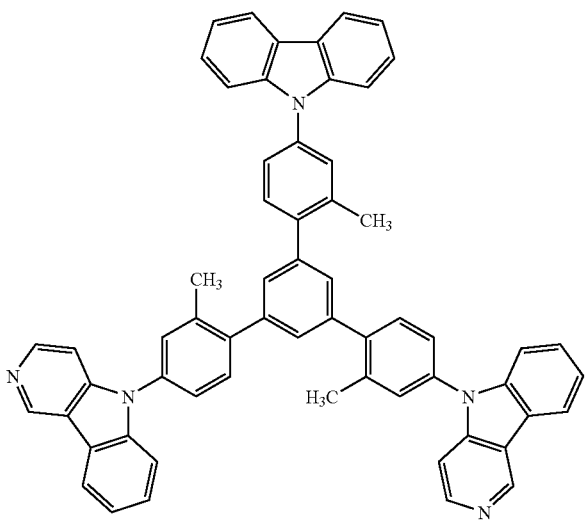

-continued
84
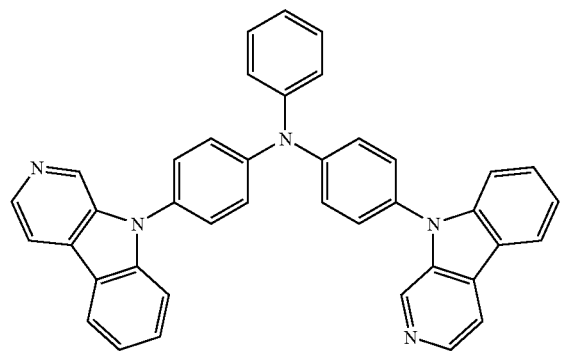
85
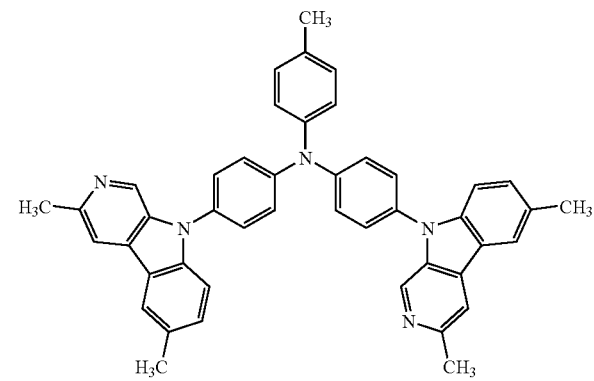
86
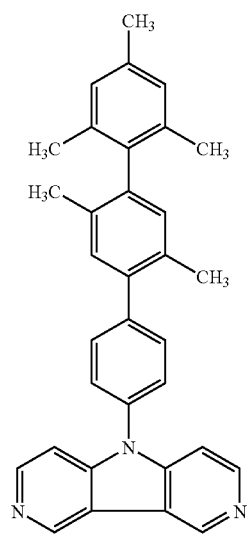
87
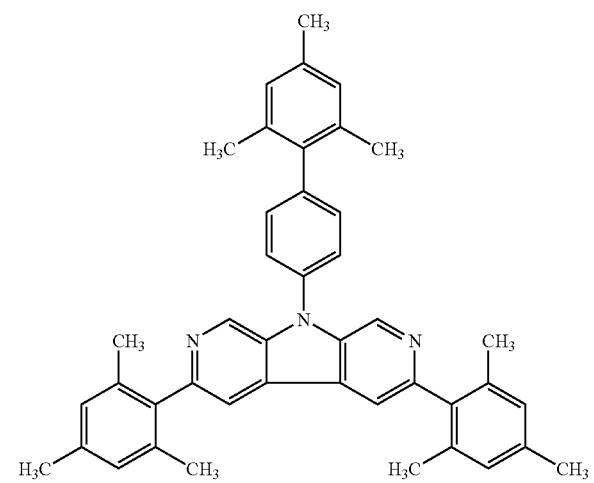
88
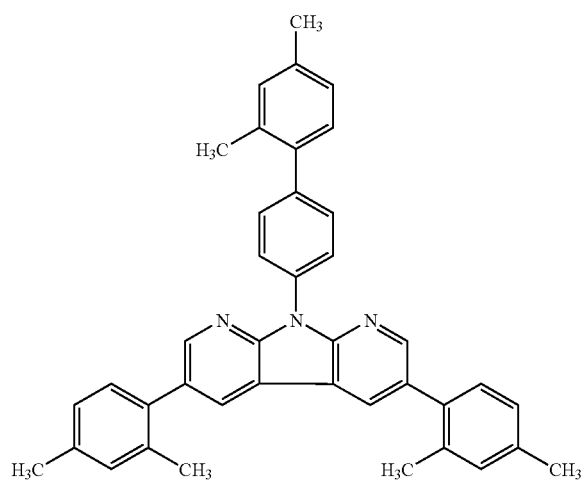
89
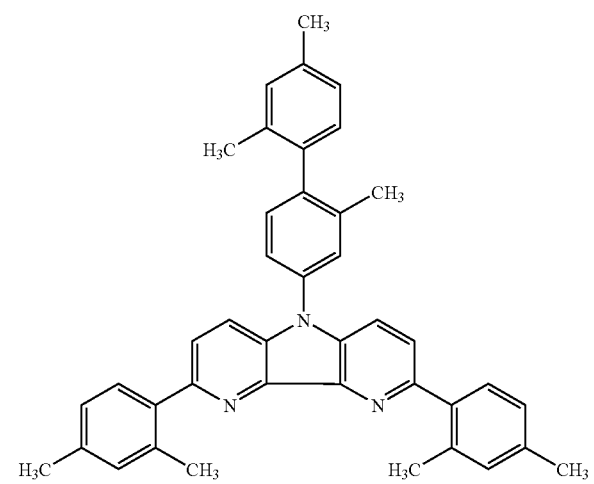

-continued
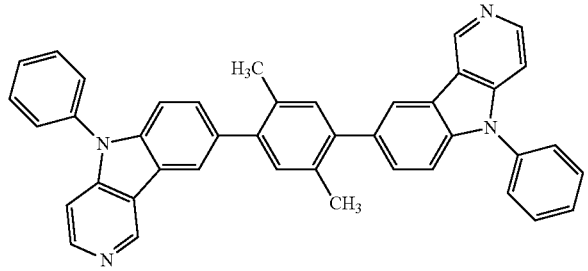
90
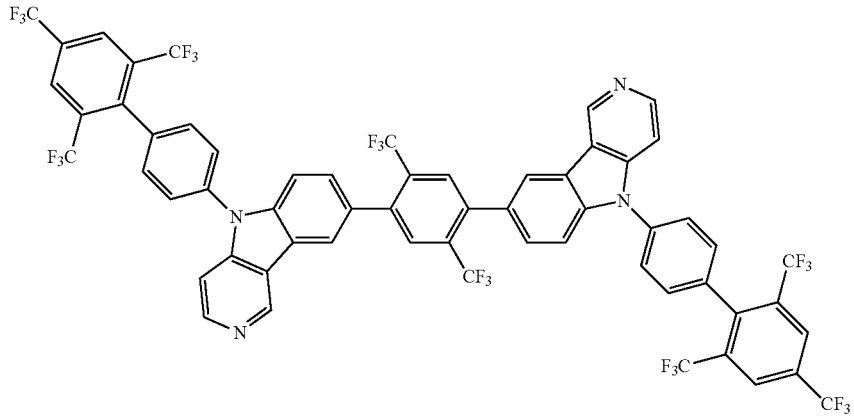
91
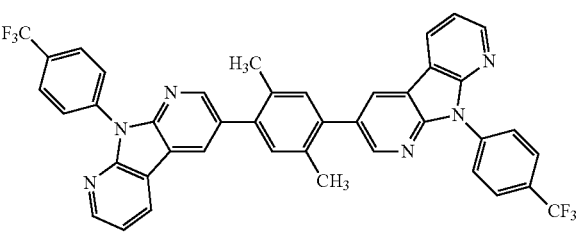
92
93
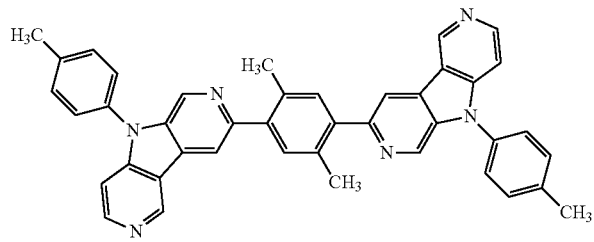
94
95
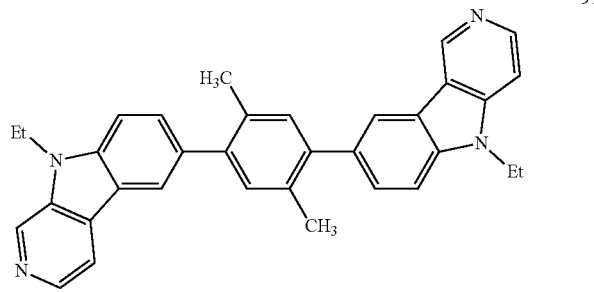
96 97

-continued

98

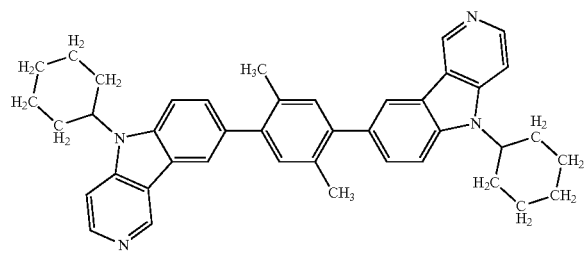

99

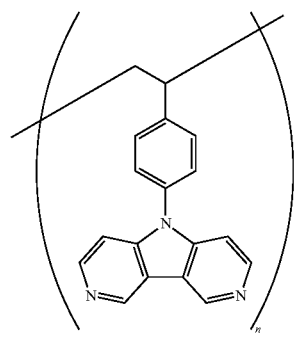

100

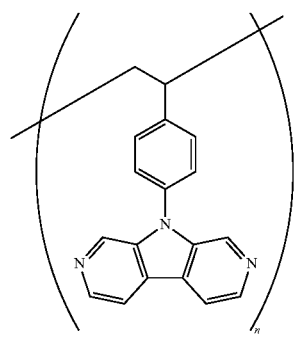

101

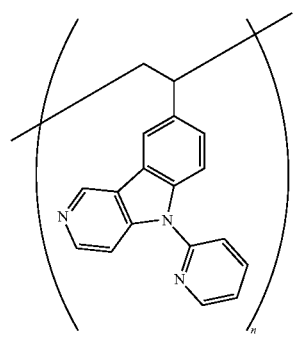

102

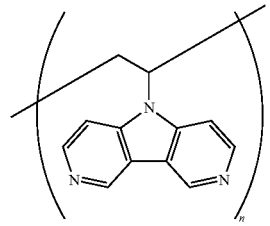

103

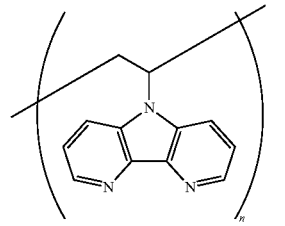

104

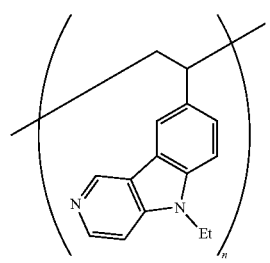

The emission layer of the present invention can be formed by using a film-forming method known in the art, for example, a vacuum deposition method, a spin coat method, a cast method and an LB method. The thickness of the emission layer is not specifically limited, however, ordinarily selected in the range of 5 nm-5 μm. The emission layer may be formed of one layer containing one kind or two or more kinds of emission materials, or may be formed of plural layers each of which may have the same composition or may have a different composition from each other.

The emission layer may be formed by dissolving the above-mentioned emission material in a solvent together with a binder such as a resin, followed by making into a film by, for example, a spin coat method, as disclosed in, for example, JP-A No. 57-51781. The thickness of the emission layer is not specifically limited and can be arbitrarily selected, however, ordinarily it is in the range of 5 nm-5 μm.

<<Blocking Layer (Electron Blocking Layer, Hole Blocking Layer>>

The blocking layer (for example, an electron blocking layer and a hole blocking layer) of the present invention will now be explained.

The thickness of the blocking layer of the present invention is preferably 3 nm-100 nm, and more preferably 5 nm-30 nm.
<<Hole Blocking Layer>>

The hole blocking layer has a function of an electron transport layer in a broad sense and contains a material having an ability of transporting electrons, however, an extremely poor ability of transporting holes, which can increase a recombination probability of electrons and holes by transporting electrons while blocking holes.

In the present invention, a platinum complex; an ortho-metallated complex; or an ortho-metallated platinum complex or a tautomer thereof represented by each of Formulae (1)-(9), of the present invention, can be preferably used in a layer adjacent to the emission layer, for example, a hole blocking layer or an electron blocking layer.

When the above-mentioned platinum complex; an ortho-metallated complex; or an ortho-metallated platinum complex or a tautomer thereof represented by each of Formulae (1)-(9), of the present invention, is used in a hole blocking layer or in an electron blocking layer, the above platinum complex may be contained in the layer with a content of 100% by weight or may be mixed with other organic compound.

The hole blocking layer, for example, disclosed in JP-A Nos. 11-204258 and 11-204359, and the hole blocking layer described in page 237 of "Organic EL element and its frontier of industrialization" (published by NTS Corporation, Nov. 30, 1998), can be used as the hole blocking layer of the present invention.

The hole blocking layer of the present invention preferably contains the above-mentioned carboline derivative or the derivative having a ring structure in which at least one of carbon atoms of a hydrocarbon ring constituting the carboline ring is replaced with a nitrogen atom.

<<Boron Derivative>>

The hole blocking layer of the present invention preferably contains a boron derivative, and more preferably contains a born derivative represented by Formula (12).

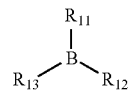

Formula (12)

In Formula (12), B represents a boron atom, $R_{11}$, $R_{12}$ and $R_{13}$ each represent a substituent, provided that one of $R_{11}$, $R_{12}$ and $R_{13}$ represents an aryl group or an heteroaryl group.

In Formula (12), the substituent represented by $R_{11}$, $R_{12}$ or $R_{13}$ is the same as the substituent defined as $R_1$ or $R_2$ in Formula (1).

Examples of an aryl group represented by $R_{11}$, $R_{12}$ or $R_{13}$ in Formula (12) include: a phenyl group, p-chlorophenyl group, a mesityl group, a tolyl group, a xylyl group, a biphenyl group, a naphthyl group, an anthryl group and a phenanthryl group.

Examples of a heteroaryl group represented by $R_{11}$, $R_{12}$ or $R_{13}$ in Formula (12) include: a furyl group, a thienyl group, a pyridyl group, a pyridazinyl group, a pyrimidinyl group, a pyrazinyl group, the triazinyl group, an imidazolyl group, a pyrazolyl group, a thiazolyl group, a quinazolinyl group, a carbazolyl group and a phthalazinyl group.

Specific examples of a boron derivative will be shown below, however, the present invention is not limited thereto.

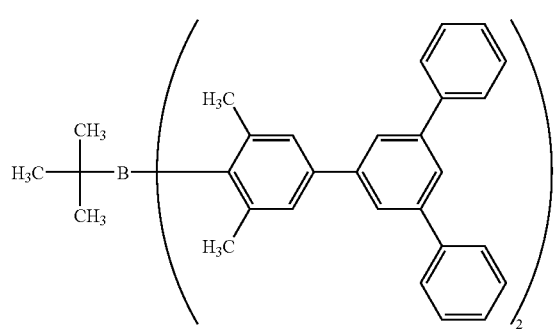

1-1

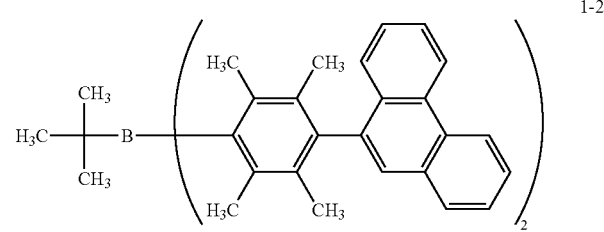

1-2

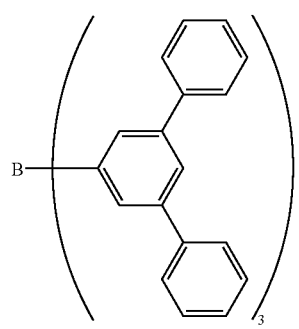

1-3

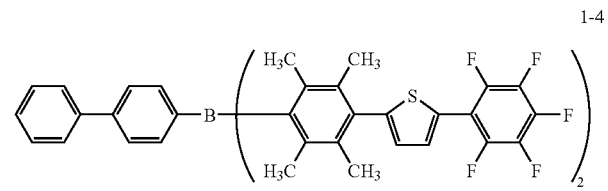

1-4

-continued
1-5
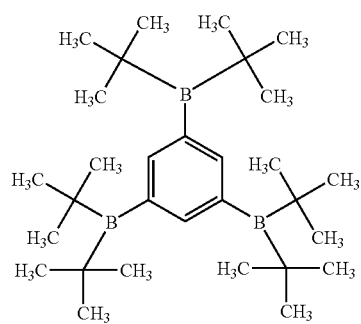
1-6
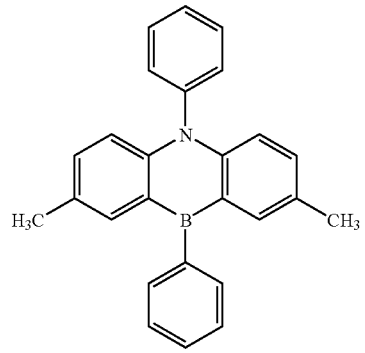
1-7
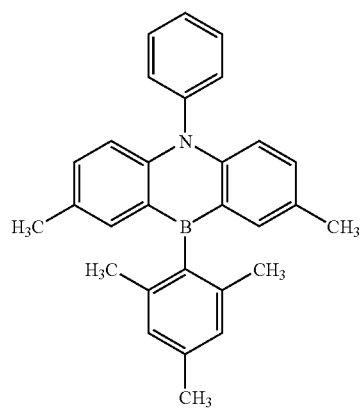
1-8
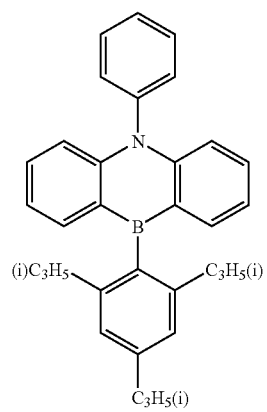
2-1
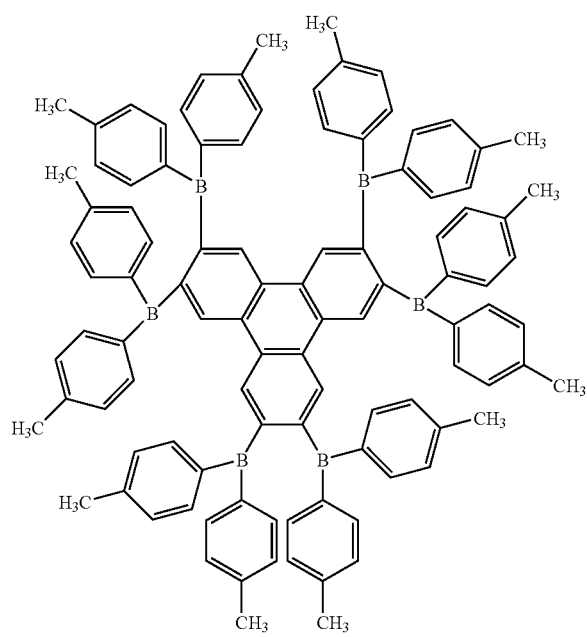
2-2

-continued
2-3
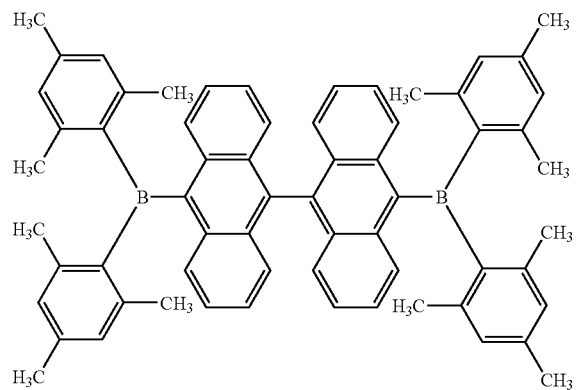
3-1
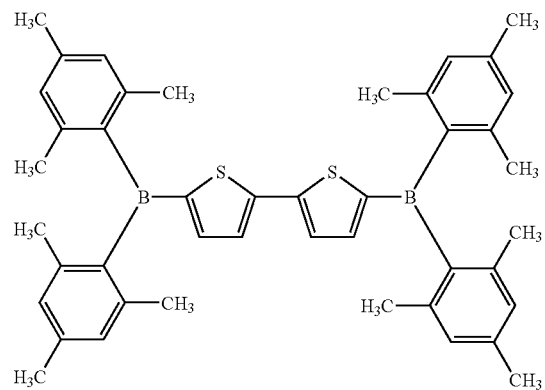
3-2
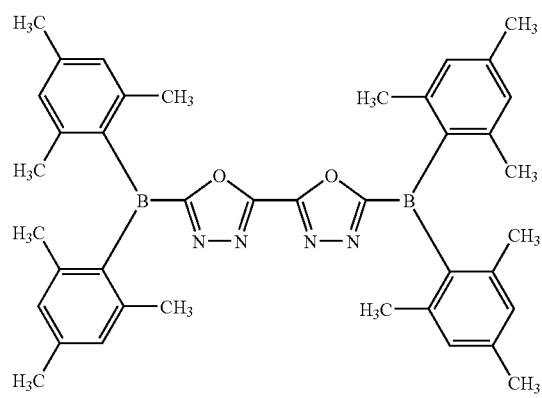
3-3
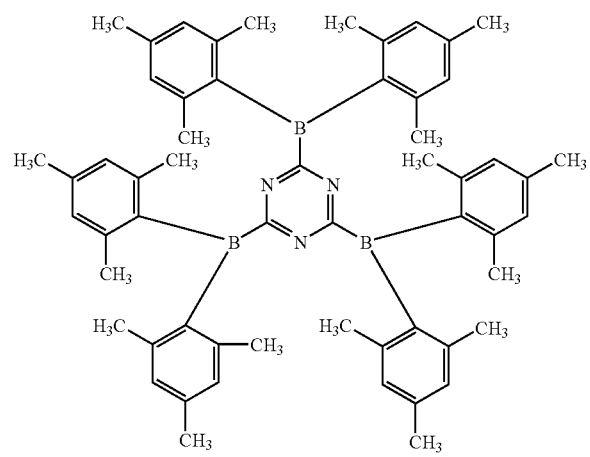
4-1
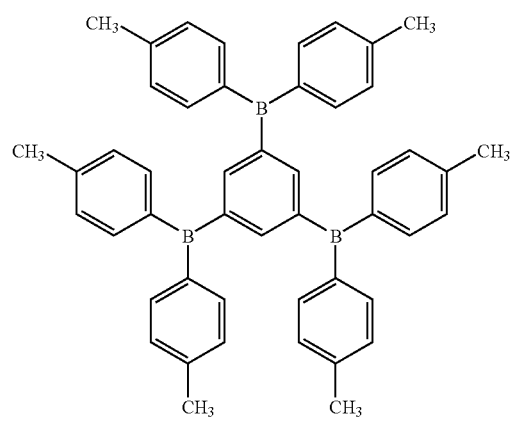
4-2
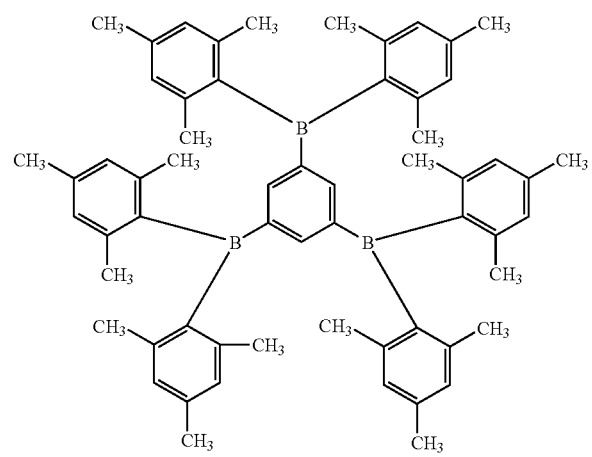

-continued
4-3
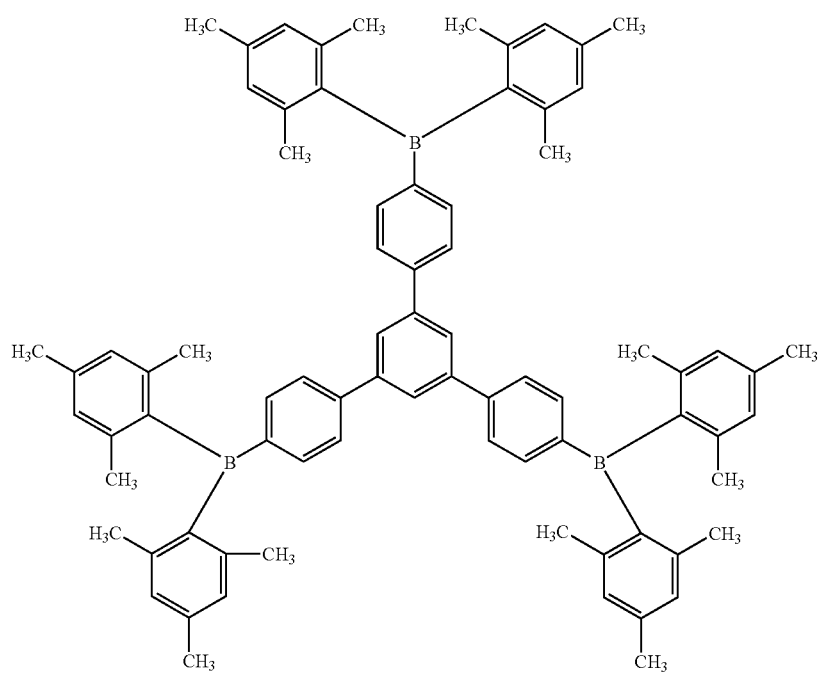
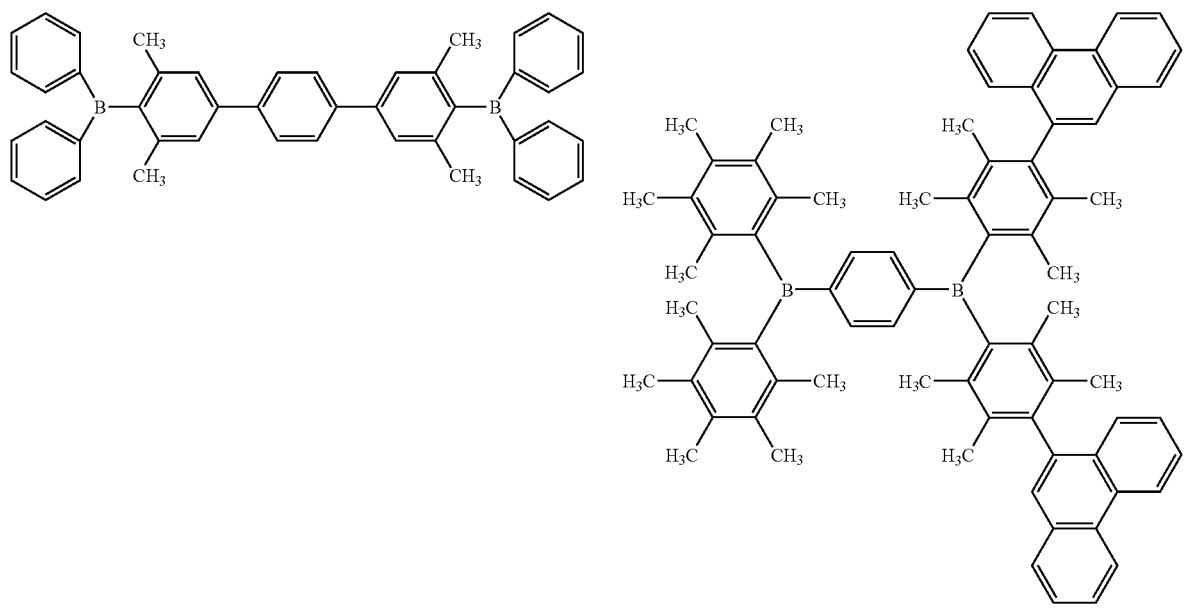
4-4
4-5

-continued
4-6
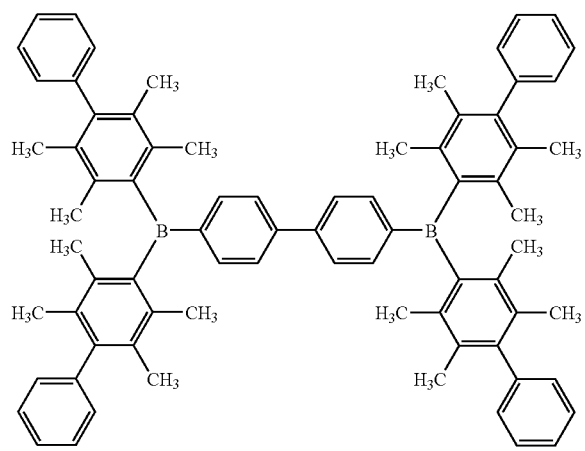
4-7
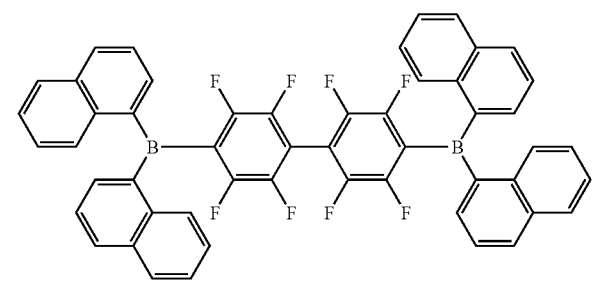
4-8
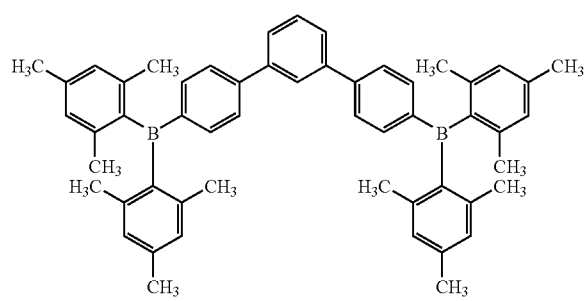
B1
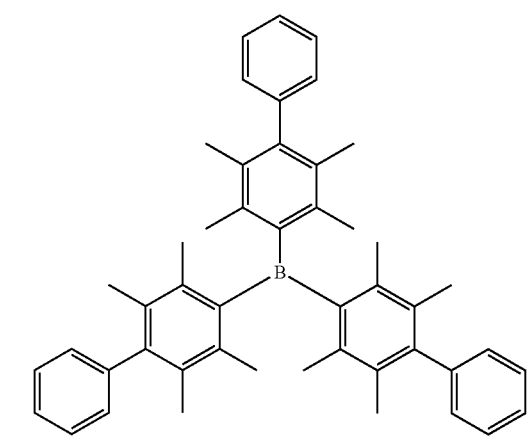
5-1
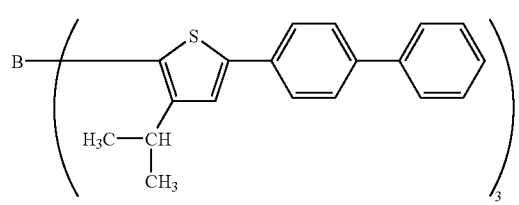
5-2
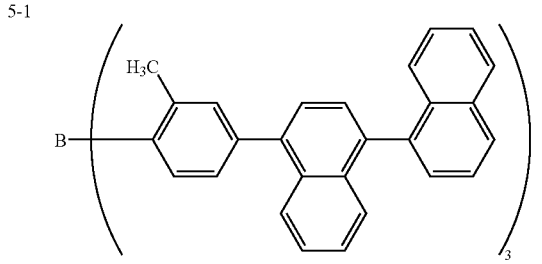
5-3
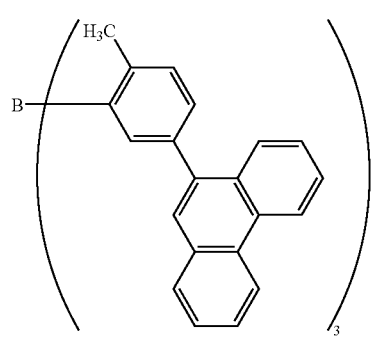
5-4
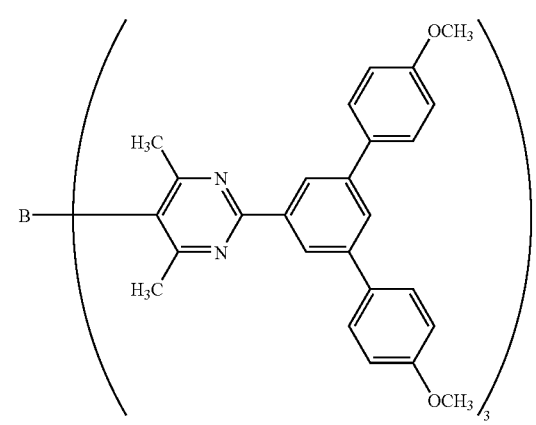

5-5
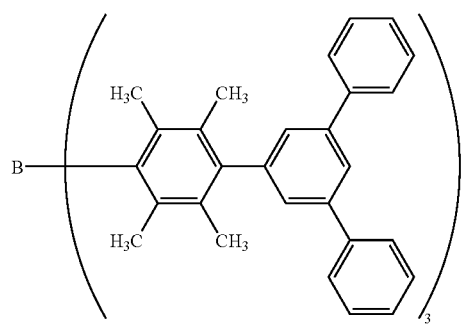
5-6
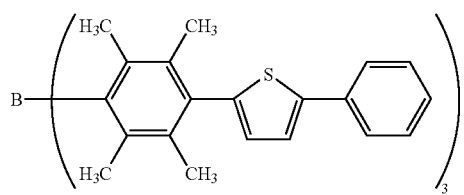
5-7
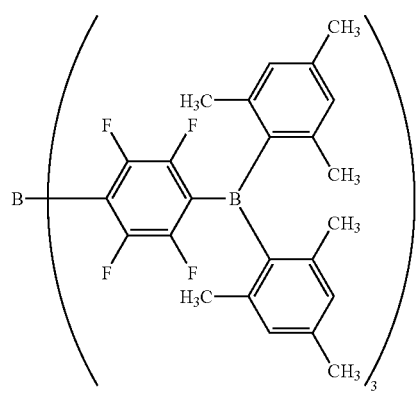
5-8
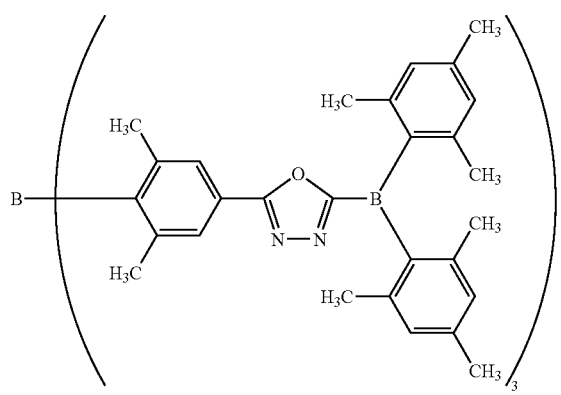
6-1
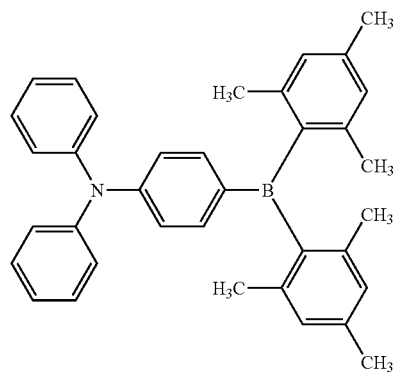
6-2
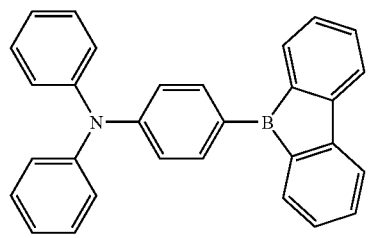
6-3
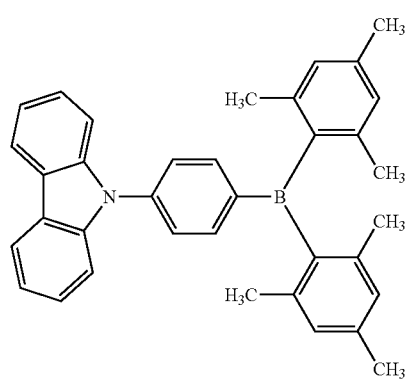
6-4
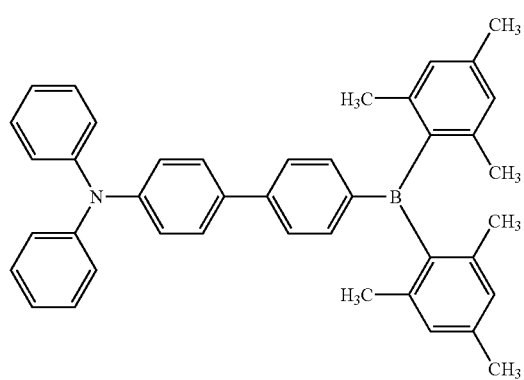

-continued
6-5
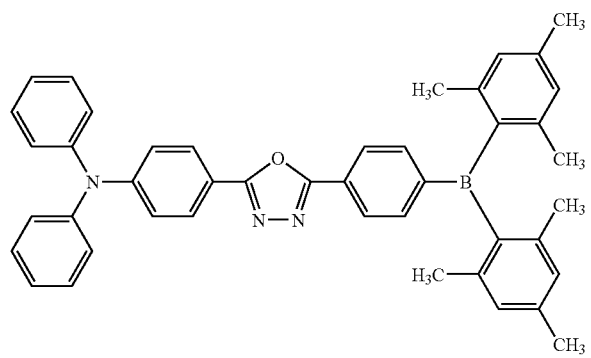
6-6
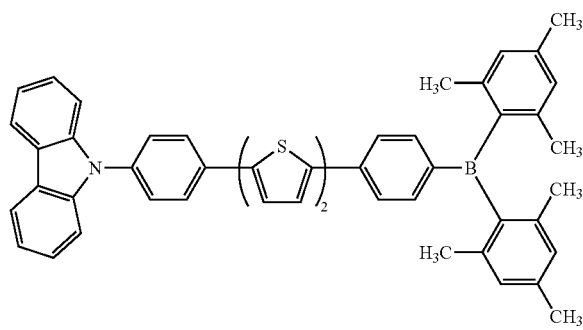
6-7
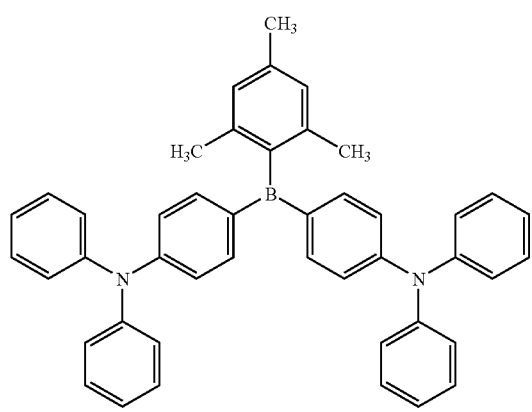
6-8
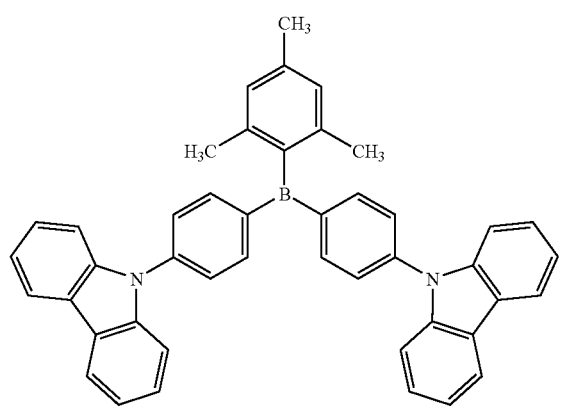
6-9
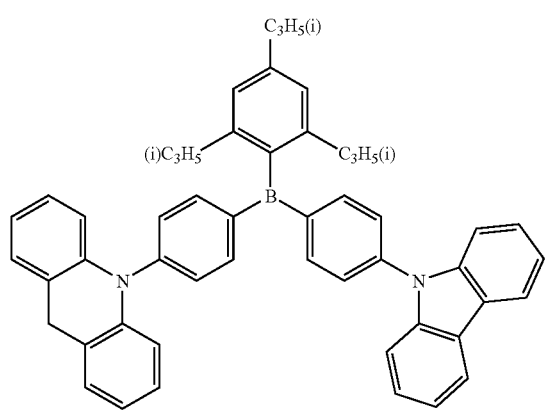
6-10
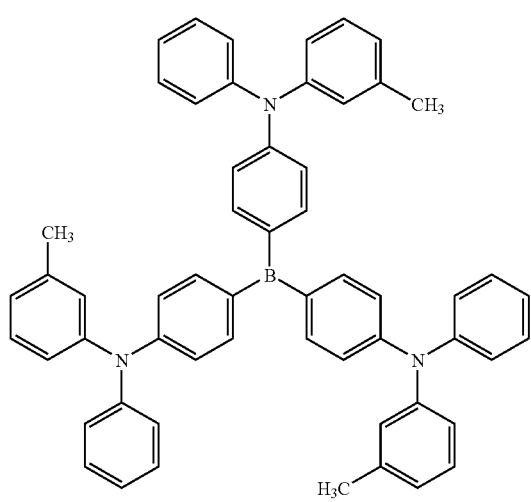

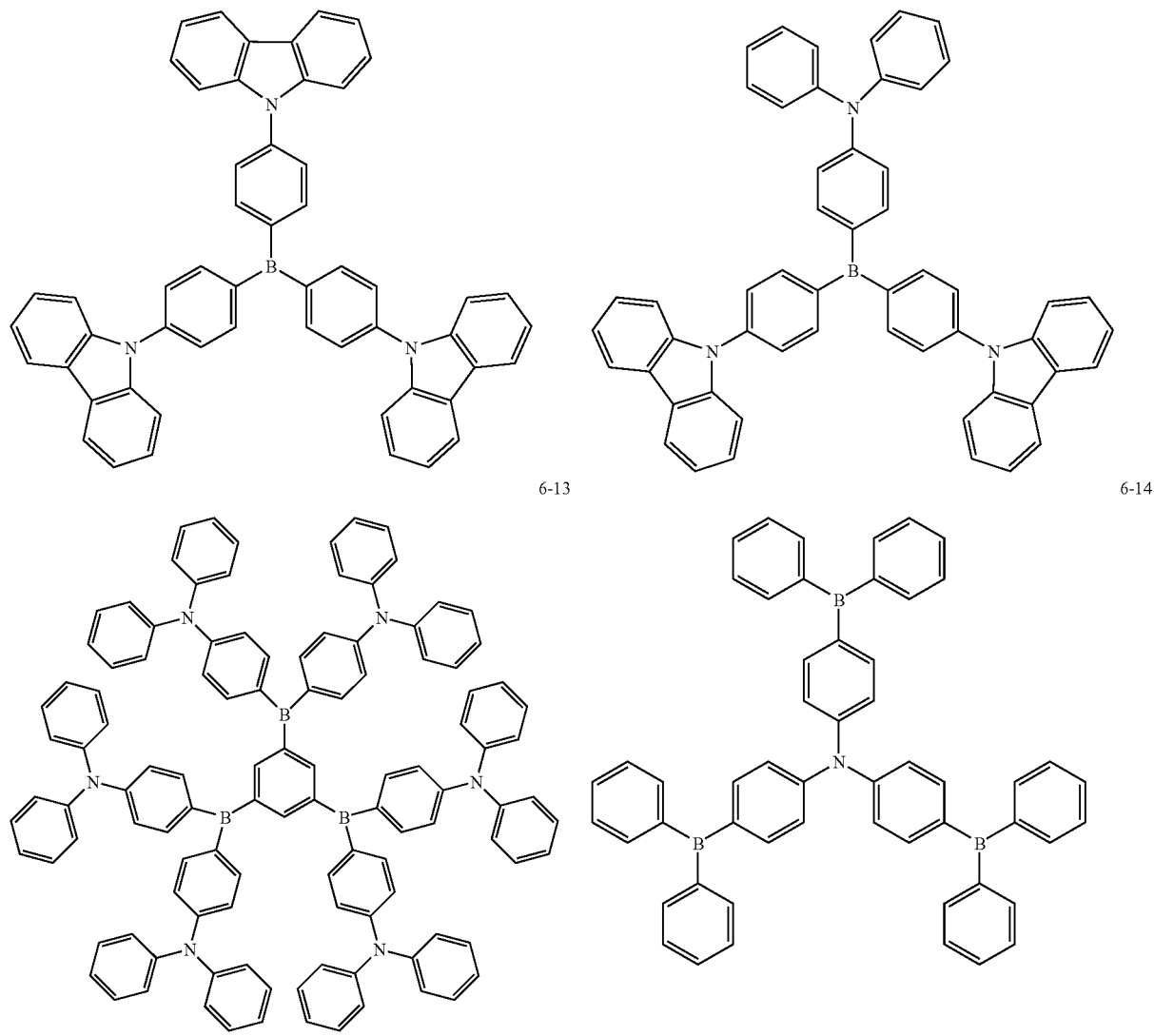

<<Electron Blocking Layer>>

The electron blocking layer has a function of an hole transport layer in a broad sense and contains a material having an ability of transporting holes, however, an extremely poor ability of transporting electrons, which can increase a recombination probability of electrons and holes by transporting holes while blocking electrons. Further, the construction of a hole transport layer which will be described later can be used as an electron blocking layer if necessary.

In the present invention, the above-mentioned platinum complex of the present invention can be preferably used in a layer adjacent to the emission layer, namely, in a hole blocking layer or in an electron blocking layer, and specifically preferably used in a hole blocking layer.

<<Hole Transport Layer>>

The hole transport layer contains a hole transport material having a hole transport ability. A hole injection layer and an electron blocking layer are included in a hole transport layer in a broad sense. The hole transport layer may either be an single layer or a lamination layer containing a plurality of layers.

The hole transport material is not specifically limited, and can be arbitrarily selected from commonly used hole injection-transport materials in a photo conduction material or from the materials known in the art in a hole injection layer or in a hole transport layer of an organic EL element.

A hole transport material means a compound having a hole injection ability, a hole transport ability or an electron blocking ability, and it may be an organic substance or an inorganic substance. Examples of a hole transport material include: a triazole derivative, an oxadiazole derivative, an imidazole derivative, a polyarylalkane derivative, a pyrazoline derivative, a pyrazolone derivative, a phenylenediamine derivative, an arylamine derivative, an amino substituted chalcone derivative, an oxazole derivative, a styrylanthracene derivative, a fluorenone derivative, a hydrazone derivative, a stilbene derivative, a silazane derivative, an aniline-containing copolymer, and an electroconductive oligomer, specifically, a thiophene oligomer.

As the hole transport material, those described above are used, however, a porphyrin compound, an aromatic tertiary amine compound and a styrylamine compound are preferable, and, specifically, an aromatic tertiary amine compound is preferable.

Typical examples of the aromatic tertiary amine compound and styrylamine compound include: N,N,N',N'-tetraphenyl-4,4'-diaminophenyl, N,N'-diphenyl-N,N'-bis(3-methylphenyl)-[1,1'-biphenyl]-4,4'-diamine (TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quardriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostylbene, N-phenylcarbazole, compounds described in U.S. Pat. No. 5,061,569 which have two condensed aromatic rings in the molecule thereof such as 4,4'-bis[N-(1-naphthyl)-N-phenylamino]biphenyl (NPD), and compounds described in JP-A No. 4-308688 such as 4,4',4"-tris[N-(3-methylphenyl)-N-phenylamino]-triphenylamine (MTDATA) in which three triphenylamine units are bonded in a starburst form.

A polymer in which the material mentioned above is introduced in the polymer chain or a polymer having the above mentioned material as the polymer main chain can also be used.

As a hole injecting material or a hole transport material, inorganic compounds such as p-Si and p-SiC are usable.

The hole transport material in the hole transport layer of the present invention preferably has a fluorescent maximum wavelength of 415 nm or less, and more preferable to have a phosphorescent O-O band of 450 nm or less. Further, the hole transport material preferably has a high Tg.

The hole transport layer can be formed by preparing a thin layer of the above-mentioned hole transport material using a known method such as a vacuum deposition method, a spin coat method, a cast method, an inkjet method, or an LB method. The thickness of the hole transport layer is not specifically limited, however, it is ordinarily from 5 nm to 5000 nm. The hole transport layer may be composed of a single layer structure containing one or more of the materials mentioned above.

<<Electron Transport Layer>>

The electron transport layer contains a material having an electron transport ability, and in a broad sense an electron injection layer or a hole blocking layer are included in an electron transport layer. The electron transport layer can be provided as a single layer or as a plurality of layers.

The following materials have been known as an electron transporting material (which serves also as a hole blocking material) used in a single electron transport layer or in the electron transport layer closest to the cathode when plural electron transport layers are employed.

The electron transport layer has a function of transporting electrons injected from a cathode to a emission layer, and the material used in the electron transport layer can be optionally selected from the compounds known in the art.

Examples of the material used in the electron transport layer (hereafter, referred to as the electron transport material) include: a nitro-substituted fluorene derivative, a diphenylquinone derivative, a thiopyran dioxide derivative, a carbodiimide, a fluolenylidenemethane derivative, an anthraquinodimethane, an anthrone derivative, and an oxadiazole derivative. Moreover, a thiadiazole derivative which is formed by substituting the oxygen atom in the oxadiazole ring of the foregoing oxadiazole derivative with a sulfur atom, and a quinoxaline derivative having a quinoxaline ring known as an electron withdrawing group are usable as the electron transporting material.

A polymer in which the material mentioned above is introduced in the polymer chain or a polymer having the material as the polymer main chain can be also used.

A metal complex of an 8-quinolynol derivative such as aluminum tris(8-quinolynol) (Alq), aluminum tris(5,7-dichloro-8-quinolynol), aluminum tris(5,7-dibromo-8-quinolynol), aluminum tris(2-methyl-8-quinolynol), aluminum tris(5-methyl-8-quinolynol), or zinc bis(8-quinolynol) (Znq), and a metal complex formed by replacing the central metal of the foregoing complexes with another metal atom such as In, Mg, Cu, Ca, Sn, Ga or Pb, can be used as the electron transport material. Furthermore, a metal free or metal-containing phthalocyanine, and a derivative thereof, in which the molecular terminal is replaced by a substituent such as an alkyl group or a sulfonic acid group, are also preferably used as the electron transport material. The distyrylpyrazine derivative exemplified as a material for the emission layer may preferably be employed as the electron transport material. An inorganic semiconductor such as n-Si and n-SiC may also be used as the electron transport material in a similar way as in the hole transport layer.

The electron transport layer can be formed employing the above described electron transport materials and by forming into a film using a known method such as a vacuum deposition method, a spin coat method, a cast method, an inkjet method or an LB method. The thickness of electron transport layer is not specifically limited, however, is ordinarily from 5 to 5000 nm. The electron transport layer may be composed of a single layer containing one kind or two or more kinds of the above-mentioned electron transport materials.

Next, the injection layer used as one of the constituting layers of the organic EL element of the present invention will be explained.

<Injection Layer>: Electron Injection Layer, Hole Injection Layer

The injection layer is optionally provided, for example, an electron injection layer or a hole injection layer, and may be provided between the anode and the emission layer or the hole transport layer, and between the cathode and the emission layer or the electron transport layer as described above.

The injection layer herein referred to is a layer provided between the electrode and an organic layer in order to reduce the driving voltage or to improve of light emission efficiency. As the injection layer, there are a hole injection layer (an anode buffer layer) and an electron injection layer (a cathode buffer layer), which are described in "Electrode Material" pages 123-166, Div. 2 Chapter 2 of "Organic EL element and its frontier of industrialization" (published by NTS Corporation, Nov. 30, 1998) in detail.

The anode buffer layer (a hole injection layer) is described in, for example, JP-A Nos. 9-45479, 9-260062, and 8-288069, and its examples include a phthalocyanine buffer layer represented by a copper phthalocyanine layer, an oxide buffer layer represented by a vanadium oxide layer, an amorphous carbon buffer layer, and a polymer buffer layer employing an electroconductive polymer such as polyaniline (emeraldine) or polythiophene.

The cathode buffer layer (an electron injection layer) is described in, for example, JP-A Nos. 6-325871, 9-17574, and 10-74586, in detail, and its examples include a metal buffer layer represented by a strontium or aluminum layer, an alkali metal compound buffer layer represented by a lithium fluoride layer, an alkali earth metal compound buffer layer represented by a magnesium fluoride layer, and an oxide buffer layer represented by an aluminum oxide.

The buffer layer (an injection layer) is preferably very thin and has a thickness of preferably from 0.1 to 100 nm depending on the kind of the material used.

The injection layer can be formed by preparing a thin layer of the above-mentioned injection material using a known method such as a vacuum deposition method, a spin coat method, a cast method, an inkjet method, or an LB method. The thickness of the injection layer is not specifically limited, however, it is ordinarily from 5 nm to 5000 nm. The injection layer may be composed of a single layer structure containing one kind or two or more kinds of the materials mentioned above.

<<Anode>>

For the anode of the organic EL element, a metal, an alloy, or an electroconductive compound each having a high working function (not less than 4 eV), and mixture thereof are preferably used as the electrode material. Specific examples of such an electrode material include a metal such as Au, CuI and a transparent electroconductive material such as indium tin oxide (ITO), $SnO_2$, or ZnO. A material capable of forming an amorphous and transparent conductive layer such as IDIXO ($In_2O_3$—ZnO) may also be used. The anode may be prepared by forming a thin layer of the electrode material according to a depositing or sputtering method, and by forming the layer into a desired pattern according to a photolithographic method. When required precision of the pattern is not so high (not less than 100 μm), the pattern may be formed by depositing or sputtering of the electrode material through a mask having a desired form. When light is emitted through the anode, the transmittance of the anode is preferably 10% or more, and the sheet resistance of the anode is preferably not more than several hundred ohm/sq. The thickness of the layer is ordinarily within the range of from 10-1000 nm, and preferably from 10-200 nm, although it may vary due to kinds of materials used.

<<Cathode>>

On the other hand, for the cathode, a metal (also referred to as an electron injecting metal), an alloy, and an electroconductive compound each having a low working function (not more than 4 eV), and a mixture thereof are used as the electrode material. Specific examples of such an electrode material include sodium, sodium-potassium alloy, magnesium, lithium, a magnesium/copper mixture, a magnesium/silver mixture, a magnesium/aluminum mixture, magnesium/indium mixture, an aluminum/aluminum oxide ($Al_2O_3$) mixture, indium, a lithium/aluminum mixture, and a rare-earth metal. Among them, a mixture of an electron injecting metal and a metal higher in the working function than that of the electron injecting metal, such as the magnesium/silver mixture, magnesium/aluminum mixture, magnesium/indium mixture, aluminum/aluminum oxide ($Al_2O_3$) mixture, lithium/aluminum mixture, or aluminum is suitable from the view point of the electron injecting ability and resistance to oxidation. The cathode can be prepared forming a thin layer of such an electrode material by a method such as a deposition or spattering method. The sheet resistance as the cathode is preferably not more than several hundred ohm/sq, and the thickness of the layer is ordinarily from 10 nm-1000 nm, and preferably from 50 nm-200 nm. It is preferable in increasing the light emission efficiency that either the anode or the cathode of the organic EL element is transparent or semi-transparent.

<<Substrate (Also Referred to as Base Plate, Base or Support)>>

The substrate employed for the organic EL element of the present invention is not restricted to specific kinds of materials such as glass and plastic, as far as it is transparent. Examples of the substrate preferably used include glass, quartz and light transmissible plastic film. Specifically preferred one is a resin film capable of providing flexibility to the organic EL element.

Examples of the resin film include films of polyethylene terephthalate (PET), polyethylene naphthalate (PEN), polyethersulfone (PES), polyetherimide, polyetheretherketone, polyphenylene sulfide, polyarylate, polyimide, polycarbonate (PC), cellulose triacetate (TAC) and cellulose acetate propionate (CAP).

The surface of the resin film may have a layer of an inorganic or organic compound or a hybrid layer of both compounds which is preferably a high barrier film having a moisture permeability of not more than 0.01 g/m$^2$·day·at.

The external light emission efficiency of the organic electroluminescence element of the present invention is preferably not less than 1%, and more preferably not less than 2% at room temperature. Herein, external quantum yield (%) is represented by the following formula:

$$\text{External quantum yield (\%)} = ((\text{the number of photons emitted to the exterior of the organic } EL \text{ element})/(\text{the number of electrons supplied to the organic } EL \text{ element})) \times 100$$

A hue improving filter such as a color filter may be used in combination.

When used as an illuminator, a film being subjected to a surface roughening treatment (for example, an antiglare film) may be used together, in order to reduce the emission irregularity.

When used as a multicolored display, at least two organic EL elements having different emission maximum wavelengths are used. A preferable example of manufacturing an organic EL element will now be explained.

<<Preparation Method of Organic EL Element>>

For one example, the preparation of the organic EL element, which has the following constitution will be described: Anode/Hole injection layer/Hole transport layer/Emission layer/Electron transport layer/Cathode buffer layer/Cathode.

A thin layer of a desired material for an electrode such as a material of the anode is formed on a suitable substrate by a vacuum deposition or sputtering method to prepare the anode so that the thickness of the layer is not more than 1 μm and preferably within the range of from 10 to 200 nm. Then organic compound thin layers including the hole injection layer, the hole transport layer, the emission layer, the hole blocking layer and the electron transport layer, which constitute the organic EL element, are formed on the resulting anode.

As methods for formation of the thin layers, as the same as described above, there are a vacuum deposition method and a wet process (for example, a spin coating method, a cast method, an inkjet method, and a printing method), however, a vacuum deposition method, a spin coating method, an inkjet method and a printing method are preferably used, since a uniform layer without a pinhole can be formed. Different methods may be used for formation of different layers. When the vacuum deposition method is used for the thin layer formation method, although conditions of the vacuum deposition differs due to kinds of materials used, vacuum deposition is preferably carried out at a boat temperature of 50-450° C., at a degree of vacuum of from $10^{-6}$ to $10^{-2}$ Pa, at a deposition speed of 0.01-50 nm/second, and at a substrate temperature of −50-300° C. to form a layer with a thickness of 0.1 nm-5 μm.

After these layers has been formed, a thin layer of a material for a cathode is formed thereon to prepare a cathode, employing, for example, a vacuum deposition method or sputtering method to give a thickness of not more than 1 μm, and preferably 50-200 nm. Thus, a desired organic EL element is obtained. It is preferred that the layers from the hole injection layer to the cathode are continuously formed under one time of vacuuming to obtain an organic EL element. However, on the way of the layer formation under vacuum, a different layer formation method by taking the layer out of the vacuum chamber may be inserted. When the different method is used, the process is required to be carried out under a dry inert gas atmosphere.

<<Display Device>>

The display device of the present invention will now be explained.

In the present invention, the display device may be single color or may be multicolor, however, a multicolor display device will now be explained. In the multicolor display of the present invention, the emission layer only is formed using a shadow mask, and the other layers, besides the emission layer, can be formed all over the substrate employing a vacuum method, a cast method, a spin coat method an inkjet method or a printing method.

When the emission layer only is formed by patterning, the layer formation, although not specifically limited, is carried out preferably according to a vacuum deposition method, an inkjet method or a printing method. When a vacuum deposition method is used as the layer formation method, patterning of the layer is preferably carried out employing a shadow mask.

Further, the organic EL element can be prepared in the reverse order, in which the cathode, the electron transport layer, the hole blocking layer, the emission layer, the hole transport layer, and the anode are formed in that order.

When a direct current voltage, a voltage of 2 to 40 V is applied to thus obtained multicolor display, setting the anode as a + polarity and the cathode as a − polarity, light emission is observed. When a voltage with the reverse polarity is applied, no current flows and no light emission is observed. When an alternating current is applied, light emission is observed only when + is applied to the anode and − is applied to the cathode. Arbitrary wave shape of alternating current may be used.

The multicolor display device can be used as a display device, a display, or various light emission sources. The display device or the display, which employs three kinds of organic EL elements emitting a blue light, a red light and a green light can present a full color image.

Examples of the display device or the display include a television, a personal computer, a mobile device or an AV device, a display for text broadcasting, and an information display used in a car. The display device may be used as specifically a display for reproducing a still image or a moving image. When the display device is used as a display for reproducing a moving image, the driving method may be either a simple matrix (passive matrix) method or an active matrix method.

Examples of an illuminator device include a home lamp, a room lamp in a car, a backlight for a watch or a liquid crystal, a light source for boarding advertisement, a signal device, a light source for a photo memory medium, a light source for an electrophotographic copier, a light source for an optical communication instrument, and a light source for an optical sensor, however, are not limited thereto.

<<Illumination Device>>

The illumination device of the present invention will now be explained.

The organic EL element of the present invention may be an organic EL element having a resonator structure. The organic EL element having a resonator structure is applied to a light source for a photo-memory medium, a light source for an electrophotographic copier, a light source for an optical communication instrument, or a light source for a photo-sensor, however, its application is not limited thereto. In the above application, a laser oscillation may be carried out.

The organic EL element of the present invention can be used as a lamp such as an illuminating lamp or a light source for exposure, as a projection device for projecting an image, or as a display for directly viewing a still image or a moving image. When the element is used in a display for reproducing a moving image, the driving method may be either a simple matrix (passive matrix) method or an active matrix method. The display can present a full color image by employing two or more kinds of organic EL elements each emitting light with a different color.

One of the examples of the display containing the organic EL element of the present invention will be explained below employing Figures.

FIG. 1 is a schematic drawing of one example of a display containing an organic EL element. FIG. 1 is a display such as that of a cellular phone, displaying image information due to light emission from the organic EL.

Display 1 contains a display section A having plural pixels and a control section B carrying out image scanning based on image information to display an image in the display section A.

The control section B is electrically connected to the display section A, transmits a scanning signal and an image data signal to each of the plural pixels based on image information from the exterior, and conducts image scanning which emits light from each pixel due to the scanning signal according to the image data signal, whereby an image is displayed on the display section A.

Figure 2:
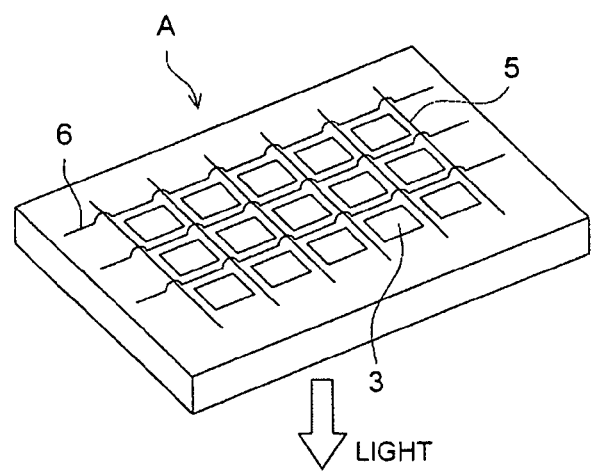
FIG. 2 is a schematic drawing of a display section A.

FIG. 2 is a schematic drawing of a display section A.

The display section A contains a substrate, plural pixels 3, and a wiring section containing plural scanning lines 5 and plural data lines 6. The main members of the display section A will be explained below.

In FIG. 2, light from pixels 3 is emitted in the direction of an arrow (downward).

The plural scanning lines 5 and plural data lines 6 of the wiring section 2 each are composed of an electroconductive material, the lines 5 and the lines 6 being crossed with each other at a right angle, and connected with the pixels 3 at the crossed points (not illustrated).

The plural pixels 3, when the scanning signal is applied from the scanning lines 5, receive the data signal from the data lines 6, and emit light corresponding to the image data received. Provision of red light emitting pixels, green light emitting pixels, and blue light emitting pixels side by side on the same substrate can display a full color image.

Next, an emission process of pixels will be explained.

Figure 3:
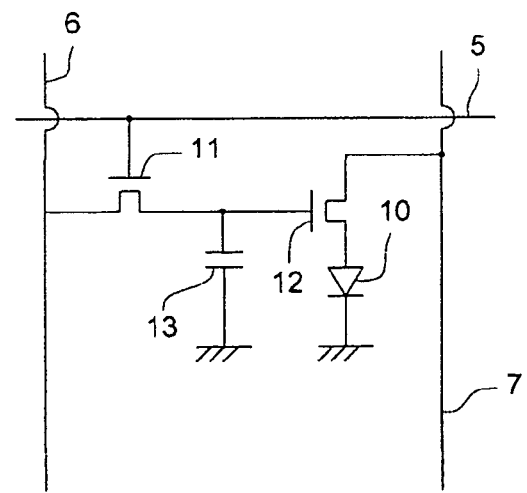
FIG. 3 is an equivalent circuit of a driving unit constituting a pixel.

FIG. 3 is a schematic drawing of a pixel.

The pixel contains an organic EL element 10, a switching transistor 11, a driving transistor 12, and a capacitor 13. When a pixel with a red light emitting organic EL element, a pixel with a green light emitting organic EL element, and a pixel with a blue light emitting organic EL element are provided side by side on the same substrate, a full color image can be displayed.

In FIG. 3, an image data signal is applied through the data lines 6 from the control section B to a drain of the switching transistor 11, and when a scanning signal is applied to a gate of the switching transistor 11 through the scanning lines 5 from the control section B, the switching transistor 11 is switched on, and the image signal data applied to the drain is transmitted to the capacitor 13 and the gate of the driving transistor 12.

The capacitor 13 is charged according to the electric potential of the image data signal transmitted, and the driving transistor 12 is switched on. In the driving transistor 12, the drain is connected to an electric source line 7, and the source to an organic EL element 10. Current is supplied from the electric source line 7 to the organic EL element 10 according to the electric potential of the image data signal applied to the gate.

The scanning signal is transmitted to the next scanning line 5 according to the successive scanning of the control section B, the switching transistor 11 is switched off. Even if the switching transistor 11 is switched off, the driving transistor 12 is turned on since the capacitor 13 maintains a charged potential of image data signal, and light emission from the organic EL element 10 continues until the next scanning signal is applied. When the next scanning signal is applied according the successive scanning, the driving transistor 12 works according to an electric potential of the next image data signal synchronized with the scanning signal, and light is emitted from the organic EL element 10.

That is, light is emitted from the organic EL element 10 in each of the plural pixels 3 due to the switching transistor 11 as an active element and the driving transistor 12 each being provided in the organic EL element 10 of each of the plural pixels 3. This emission process is called an active matrix process.

Herein, light emission from the organic EL element 10 may be emission with plural gradations according to image signal data of multiple value having plural gradation potentials, or emission due to on-off according to a binary value of the image data signals.

The electric potential of the capacitor 13 may maintain till the next application of the scanning signal, or may be discharged immediately before the next scanning signal is applied.

In the present invention, light emission may be carried out employing a passive matrix method as well as the active matrix method as described above. The passive matrix method is one in which light is emitted from the organic EL element according to the data signal only when the scanning signals are scanned.

Figure 4:
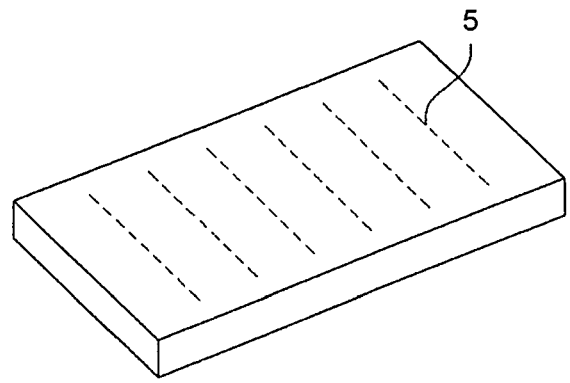
FIG. 4 is a schematic drawing of a display device employing a passive matrix method.
Figure 4:
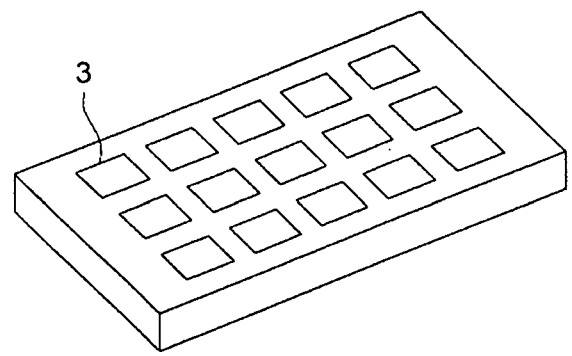
Figure 4:
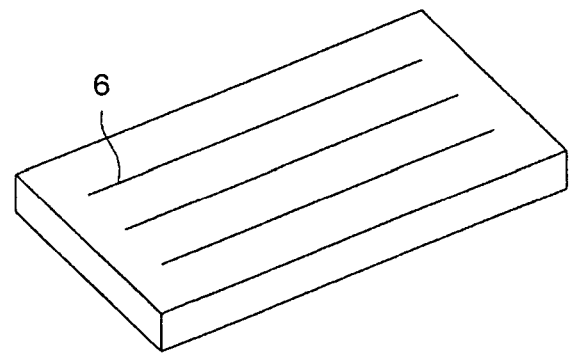

FIG. 4 is a schematic drawing of a display employing a passive matrix method. In FIG. 4, pixels 3 are provided between the scanning lines 5 and the data lines 6, crossing with each other.

When scanning signal is applied to scanning line 5 according to successive scanning, pixel 3 connecting the scanning line 5 emits according to the image data signal.

The passive matrix method has no active element in the pixel 3, which reduces manufacturing cost of a display.

EXAMPLES

Hereafter, the present invention will be explained using the examples, however, the present invention is not limited thereto.

The materials used for formation of the emission host, emission dopant, and hole blocking layer in any one of Examples 1-6 ill be shown below. None of the platinum complexes of Comparatives 1-9 shown below have an aryl group of which free rotation is blocked or an aromatic heterocycle group of which free rotation is blocked.

Comparative 1

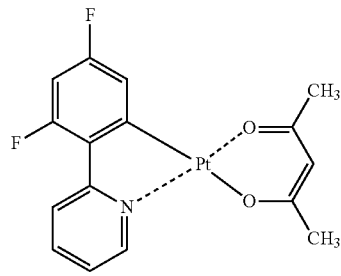

Comparative2

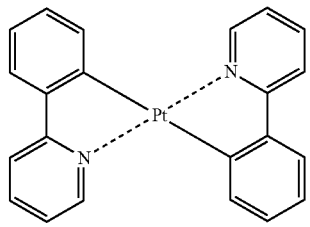

Comparative 3

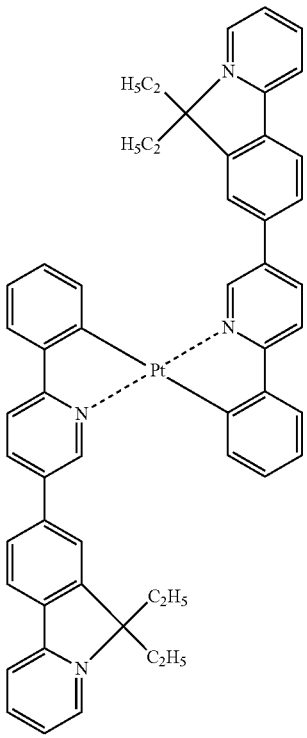

-continued
Comparative 4
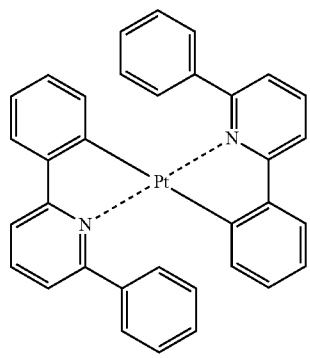
Comparative 5
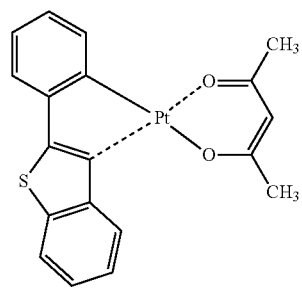
Comparative 6
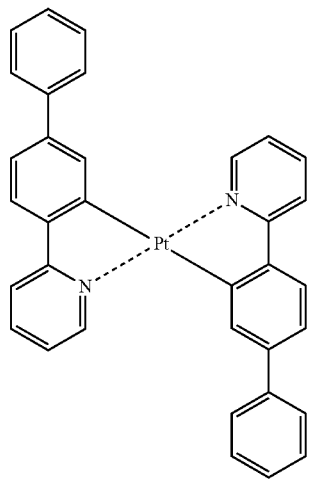
Comparative 7
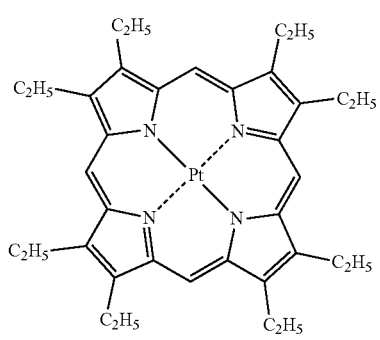
-continued
Comparative 8
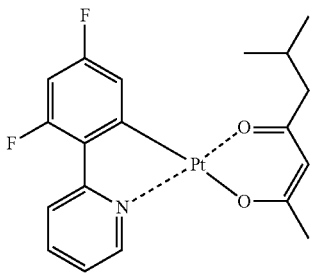
Comparative 9
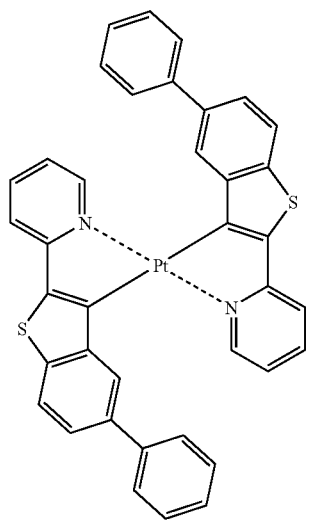
TCBP1
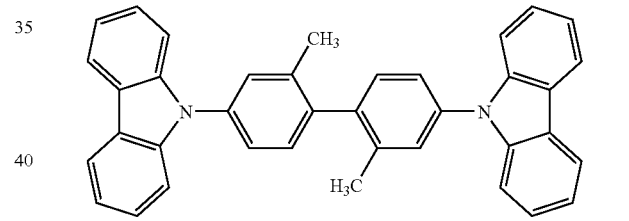
TCBP2
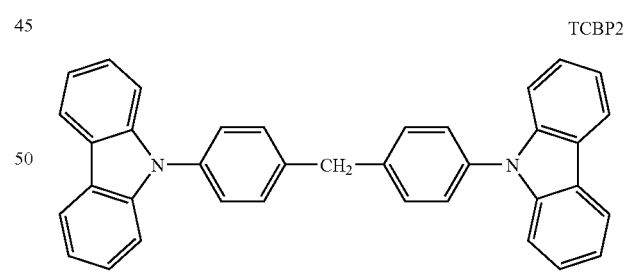
ACZ1
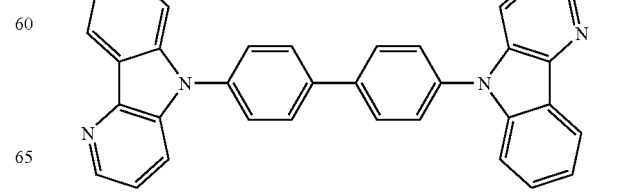

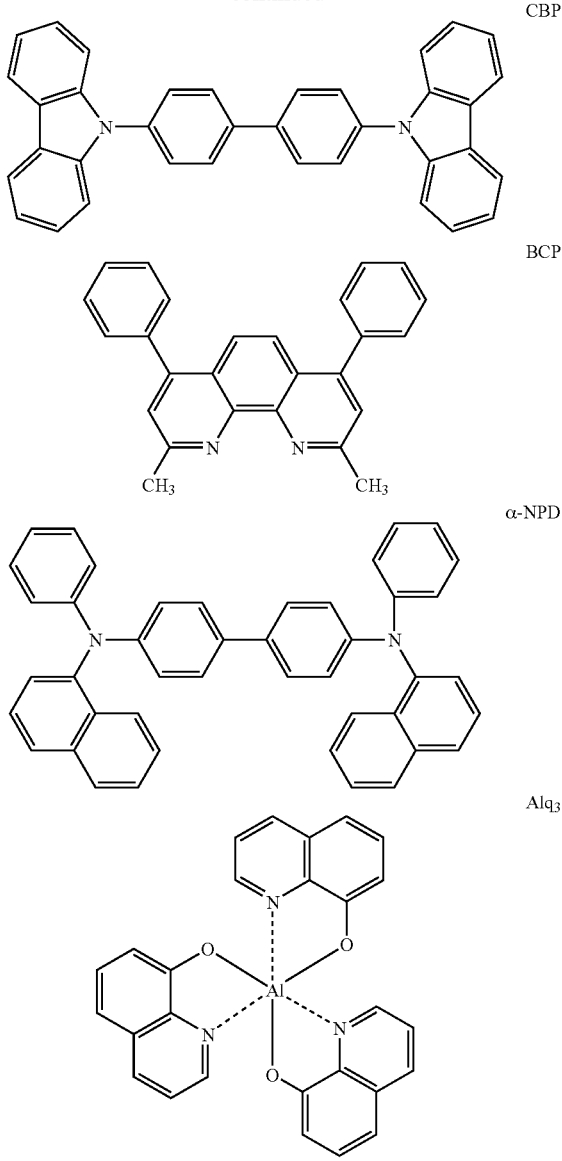

<<Preparation of Organic EL Element OLED1-1>>

Example 1

A pattern was formed on a substrate composed of a glass plate and a 150 nm ITO layer (NA45 manufactured by NH Technoglass Co., Ltd.) as an anode. Then the resulting transparent substrate having the ITO transparent electrode was subjected to ultrasonic washing in iso-propyl alcohol and dried with a dry nitrogen gas and subjected to UV-ozone cleaning for 5 minutes.

Thus obtained transparent substrate was fixed on a substrate holder of a vacuum deposition apparatus available on the market. On the other hand, in five resistive heating tantalum boats, α-NPD, CBP, Ir-10, BCP, and Alq$_3$ were placed one by one, and fixed in the vacuum deposition apparatus (a first vacuum chamber).

Further, lithium fluoride was placed in a resistive heating tantalum boat, and aluminum was placed in a resistive heating molybdenum boat, and fixed in a second vacuum chamber.

After the pressure in the first vacuum chamber was reduced to $4 \times 10^{-4}$ Pa, the boat carrying α-NPD was heated by supplying an electric current to the boat, and α-NPD was deposited onto the transparent substrate at a depositing rate of 0.1 nm/sec-0.2 nm/sec to form a 25 nm thick hole injection/transport layer.

Further, the boat carrying CBP and the boat carrying Ir-10 were independently heated by supplying an electric current, and a emission layer with a thickness of 30 nm was formed, while the ratio of (the deposition rate of CBP which was an emission host): (the deposition rate of Ir-10 which was an emission dopant) was controlled to be 100:7.

Subsequently, the boat carrying BCP was heated by supplying an electric current to the boat, and BCP was deposited at a depositing rate of 0.1 nm/sec-0.2 nm/sec to form a hole blocking layer with a thickness of 10 nm. Further, the boat carrying Alq$_3$ was heated by supplying an electric current, and Alq$_3$ was deposited at a depositing rate of 0.1 nm/sec-0.2 nm/sec to form an electron transport layer with a thickness of 40 nm.

Next, the element in which the electron injection layer was formed was transferred to the second vacuum chamber, and a stainless-steel mask having rectangular holes was set on the electron injection layer using a remote control device.

Figure 5:
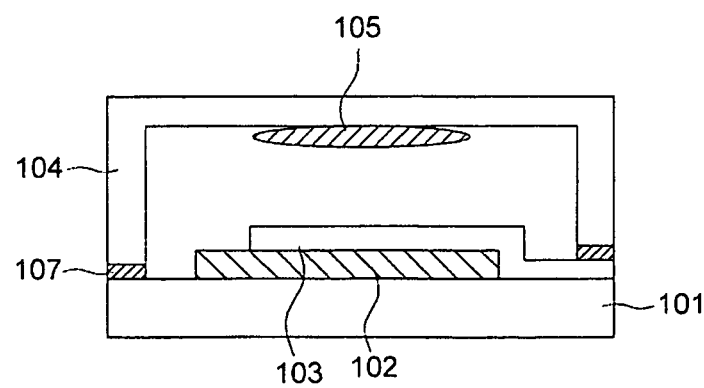
FIG. 5 is a schematic drawing of a sealing structure of Organic EL Element OELE 1-1.

After the second vacuum chamber was evacuated down to $2 \times 10^{-4}$ Pa, the boat carrying lithium fluoride was heated by supplying an electric current, and lithium fluoride was deposited at a depositing rate of 0.1 nm/sec-0.2 nm/sec to form a cathode buffer layer with a thickness of 0.5 nm, and subsequently, the boat carrying aluminum was heated by supplying an electric current, and aluminum was deposited at a depositing rate of 1-2 nm/sec to form a cathode with a thickness of 150 nm. Thus prepared organic EL element was moved, without being in contact with air, to a nitrogen atmosphere glove box (a glove box, the atmosphere being substituted with high purity nitrogen gas of 99.999% or more), and the sealed structure, inside of which was substituted with nitrogen, for example, as shown in FIG. 5, was fabricated to prepare OLED1-1. A dehydrating agent: barium oxide 105 was provided by preliminarily adhering high purity barium oxide powder produced by Sigma-Aldrich Co. in glass sealing container 104 using a semi-permeable fluorine resin film (Microtex: S-NTF8031Q produced by NITTO DENKO Corp.) having an adhesive. UV-curable resin adhesive 107 was used to adhere the organic EL element and the sealing container, and, by irradiating UV rays, the seal was completed and a sealed organic EL element was obtained. In FIG. 5, 101 represents a glass substrate having a transparent electrode, 102 represents an organic EL layer containing above-mentioned hole injection/transport layer, emission layer, hole blocking layer and electron transport layer, and 103 represents a cathode.

<<Preparation of Organic EL Elements OLED1-2 to 1-24>>

Organic EL Elements OLED1-2 to 1-24 were prepared in the same manner as Organic EL Element OLED1-1, except that the emission dopants and the emission hosts were changed as shown in Table 1.

For each of the obtained Organic EL Elements OLED1-1 to 1-24, the following evaluations were carried out.

<<External Quantum Efficiency>>

Electric current of 2.5 mA/cm$^2$ was supplied to each of Organic EL Elements OLED1-1 to 1-24 at an ambient temperature (23-25° C.) to put each element on, and the external quantum efficiency (η) of each sample was determined by measuring the luminance of the emission just after the element was put on. The measurement of luminance was carried out using CS-1000 (produced by Minolta Inc).

Each external quantum efficiency was expressed as a relative value when the value for Organic EL Elements OLED1-1 was set to 100.

<<Emission Life>>

Electric current of 2.5 mA/cm$^2$ was continuously supplied to each of Organic EL Elements OLED1-1 to 1-24 to put each element on, and a period in which an initial luminance of an organic EL element decreased to half of it ($\tau\frac{1}{2}$) was measured. Each emission life was expressed as a relative value when the value for Organic EL Element OLED1-1 was set to 100.

Obtained results were summarized in Table 1.

TABLE 1

| Element No. | Emission Host | Emission Dopant | External Quantum Efficiency | Emission Life | Remarks |
|---|---|---|---|---|---|
| OLED1-1 | CBP | Ir-10 | 100 | 100 | Comp. |
| OLED1-2 | CBP | Ir-12 | 97 | 90 | Comp. |
| OLED1-3 | CBP | Comparative 1 | 95 | 82 | Comp. |
| OLED1-4 | CBP | Comparative 8 | 100 | 105 | Comp. |
| OLED1-5 | CBP | 9 | 116 | 175 | Inv. |
| OLED1-6 | CBP | 13 | 107 | 138 | Inv. |
| OLED1-7 | CBP | 19 | 112 | 140 | Inv. |
| OLED1-8 | CBP | 37 | 115 | 150 | Inv. |
| OLED1-9 | CBP | 38 | 106 | 135 | Inv. |
| OLED1-10 | CBP | 35 | 112 | 160 | Inv. |
| OLED1-11 | CBP | 64 | 109 | 135 | Inv. |
| OLED1-12 | CBP | 68 | 109 | 152 | Inv. |
| OLED1-13 | CBP | 69 | 104 | 130 | Inv. |
| OLED1-14 | CBP | 70 | 109 | 133 | Inv. |
| OLED1-15 | CBP | 71 | 116 | 172 | Inv. |
| OLED1-16 | TCBP1 | 9 | 124 | 180 | Inv. |
| OLED1-17 | TCBP2 | 9 | 123 | 215 | Inv. |
| OLED1-18 | ACZ1 | 9 | 120 | 225 | Inv. |
| OLED1-19 | TCBP1 | 68 | 120 | 160 | Inv. |
| OLED1-20 | TCBP2 | 68 | 120 | 198 | Inv. |
| OLED1-21 | ACZ1 | 68 | 118 | 203 | Inv. |
| OLED1-22 | TCBP1 | 19 | 117 | 148 | Inv. |
| OLED1-23 | TCBP2 | 19 | 120 | 177 | Inv. |
| OLED1-24 | ACZ1 | 19 | 118 | 183 | Inv. |

Inv.: Inventive, Comp.: Comparative

Table 1 revealed that each of the organic EL elements prepared by using one the platinum complexes of the present invention as an organic EL element material clearly attained a higher emission efficiencies and a longer emission life compared to those of the Comparative organic EL elements. Comparative Organic EL Elements OLED1-1, 1-2, and inventive Organic EL Elements OLED1-5 to 1-24 all emitted blue light, while comparative Organic EL Elements OLED1-3 and 1-4 emitted light of aqua color.

Further improved effect of the present invention was observed, when one of the following compound was incorporated in the emission layer, namely, the compound represented by Formula (10) or (11), or the carboline derivative, one of carbon atoms of a hydrocarbon ring constituting the carboline ring of the carboline derivative being replaced with a nitrogen atom. Although the results were not shown in Table 1, further improved effect of the present invention was observed, when one of the following compound was incorporated in the hole blocking layer, namely, the boron derivative, the carboline derivative, or the carboline derivative, one of carbon atoms of a hydrocarbon ring constituting the carboline ring of the carboline derivative being replaced with a nitrogen atom.

Example 2

<<Preparation of Organic EL Elements OLED2-1 to 2-31>>

Organic EL Elements OLED2-1 to 2-31 were prepared in the same manner as in Example 1, except that the emission dopants and the emission hosts were changed as shown in Table 2.

The external quantum efficiency and the emission life of each of the obtained organic EL elements were measured in the same manner as in Example 1.

The external quantum efficiency and the emission life of each of the obtained organic EL elements were expressed as relative values when each of those values of Organic EL Element OLED2-1 was set to 100. The obtained results were summarized in Table 2.

TABLE 2

| Element No. | Emission Host | Emission Dopant | External Quantum Efficiency | Emission Life | Remarks |
|---|---|---|---|---|---|
| OLED2-1 | CBP | Ir-1 | 100 | 100 | Comp. |
| OLED2-2 | CBP | Comparative 2 | 94 | 85 | Comp. |
| OLED2-3 | CBP | Comparative 3 | 102 | 110 | Comp. |
| OLED2-4 | CBP | Comparative 4 | 100 | 101 | Comp. |
| OLED2-5 | CBP | Comparative 6 | 98 | 98 | Comp. |
| OLED2-6 | CBP | 1 | 114 | 177 | Inv. |
| OLED2-7 | CBP | 4 | 106 | 125 | Inv. |
| OLED2-8 | CBP | 5 | 110 | 135 | Inv. |
| OLED2-9 | CBP | 6 | 112 | 168 | Inv. |
| OLED2-10 | CBP | 7 | 110 | 155 | Inv. |
| OLED2-11 | CBP | 16 | 105 | 139 | Inv. |
| OLED2-12 | CBP | 20 | 109 | 165 | Inv. |
| OLED2-13 | CBP | 48 | 104 | 134 | Inv. |
| OLED2-14 | CBP | 49 | 105 | 132 | Inv. |
| OLED2-15 | CBP | 51 | 113 | 179 | Inv. |
| OLED2-16 | CBP | 56 | 108 | 165 | Inv. |
| OLED2-17 | CBP | 57 | 108 | 158 | Inv. |
| OLED2-18 | CBP | 58 | 107 | 160 | Inv. |
| OLED2-19 | CBP | 59 | 109 | 145 | Inv. |
| OLED2-20 | CBP | 60 | 112 | 170 | Inv. |
| OLED2-21 | CBP | 66 | 110 | 149 | Inv. |
| OLED2-22 | CBP | 72 | 112 | 178 | Inv. |
| OLED2-23 | TCBP1 | 6 | 114 | 171 | Inv. |
| OLED2-24 | TCBP2 | 6 | 115 | 211 | Inv. |
| OLED2-25 | ACZ1 | 6 | 114 | 223 | Inv. |
| OLED2-26 | TCBP1 | 72 | 114 | 184 | Inv. |
| OLED2-27 | TCBP2 | 72 | 114 | 223 | Inv. |
| OLED2-28 | ACZ1 | 72 | 113 | 234 | Inv. |
| OLED2-29 | TCBP1 | 20 | 112 | 173 | Inv. |
| OLED2-30 | TCBP2 | 20 | 113 | 190 | Inv. |
| OLED2-31 | ACZ1 | 20 | 113 | 203 | Inv. |

Inv.: Inventive, Comp.: Comparative

Table 2 revealed that each of the organic EL elements prepared by using the organic EL element material of the present invention as an emission dopant attained a higher emission efficiencies and a longer emission life compared to those of the Comparative organic EL elements. The inventive organic EL elements emitted green light.

Further improved effect of the present invention was observed when one of the following compound was incorporated in the emission layer, namely, the compound represented by Formula (10) or (11), or the carboline derivative, one of carbon atoms of a hydrocarbon ring constituting the carboline ring of the carboline derivative being replaced with a nitrogen atom, and when, although the results were not shown in Table 2, one of the following compound was incorporated in the hole blocking layer, namely, the boron derivative, the carboline derivative, or the carboline derivative, one of carbon atoms of a hydrocarbon ring constituting the carboline ring of the carboline derivative being replaced with a nitrogen atom.

Example 3

<<Preparation of Organic EL Elements OLED3-1 to 3-24>>

Organic EL Elements OLED3-1 to 3-24 were prepared in the same manner as in Example 1, except that the emission dopants and the emission hosts were changed as shown in Table 3. The external quantum efficiency and the emission life of each of the obtained organic EL elements were measured in the same manner as in Example 1. The external quantum efficiency and the emission life of each of the obtained organic EL elements were expressed as relative values when each of those values of Organic EL Element OLED3-1 was set to 100. The obtained results were summarized in Table 3.

TABLE 3

| Element No. | Emission Host | Emission Dopant | External Quantum Efficiency | Emission Life | Remarks |
| --- | --- | --- | --- | --- | --- |
| OLED3-1 | CBP | Ir-9 | 100 | 100 | Comp. |
| OLED3-2 | CBP | Comparative 5 | 83 | 91 | Comp. |
| OLED3-3 | CBP | Comparative 7 | 92 | 98 | Comp. |
| OLED3-4 | CBP | Comparative 9 | 98 | 100 | Comp. |
| OLED3-5 | CBP | 23 | 109 | 136 | Inv. |
| OLED3-6 | CBP | 24 | 115 | 144 | Inv. |
| OLED3-7 | CBP | 26 | 105 | 137 | Inv. |
| OLED3-8 | CBP | 28 | 112 | 149 | Inv. |
| OLED3-9 | CBP | 31 | 107 | 132 | Inv. |
| OLED3-10 | CBP | 34 | 106 | 134 | Inv. |
| OLED3-11 | CBP | 54 | 112 | 146 | Inv. |
| OLED3-12 | CBP | 62 | 113 | 150 | Inv. |
| OLED3-13 | CBP | 65 | 112 | 148 | Inv. |
| OLED3-14 | CBP | 73 | 109 | 149 | Inv. |
| OLED3-15 | CBP | 74 | 110 | 142 | Inv. |
| OLED3-16 | TCBP1 | 73 | 114 | 152 | Inv. |
| OLED3-17 | TCBP2 | 73 | 115 | 188 | Inv. |
| OLED3-18 | ACZ1 | 73 | 112 | 190 | Inv. |
| OLED3-19 | TCBP1 | 65 | 114 | 158 | Inv. |
| OLED3-20 | TCBP2 | 65 | 114 | 192 | Inv. |
| OLED3-21 | ACZ1 | 65 | 113 | 204 | Inv. |
| OLED3-22 | TCBP1 | 74 | 112 | 148 | Inv. |
| OLED3-23 | TCBP2 | 74 | 113 | 185 | Inv. |
| OLED3-24 | ACZ1 | 74 | 112 | 197 | Inv. |

Inv.: Inventive, Comp.: Comparative

Table 3 revealed that each of the organic EL elements prepared by using the compound of the present invention as an emission dopant attained a higher emission efficiencies and a longer emission life compared to those of the Comparative organic EL elements. The inventive organic EL elements all emitted red light.

Further improved effect of the present invention (high luminance of emission and elongation of emission life) was observed when one of the following compound was incorporated in the emission layer, namely, the compound represented by Formula (10) or (11), or the carboline derivative, one of carbon atoms of a hydrocarbon ring constituting the carboline ring of the carboline derivative being replaced with a nitrogen atom, and when, although the results were not shown in Table 3, one of the following compound was incorporated in the hole blocking layer, namely, the boron derivative, the carboline derivative, or the carboline derivative, one of carbon atoms of a hydrocarbon ring constituting the carboline ring of the carboline derivative being replaced with a nitrogen atom.

Example 4

<<Preparation of Organic EL Elements OLED4-1 to 4-16>>

Organic EL Element OLED4-1 was prepared in the same manner as Organic EL Element OLED2-1 in Example 2, and Organic EL Elements OLED4-2 to 4-19 were prepared in the same manner as Organic EL Element OLED4-1, except that the emission hosts, the emission dopants and hole blocking material were changed as shown in Table 4.

The external quantum efficiency and the emission life of each of Organic EL Elements OLED4-1 to 4-19 were measured in the same manner as in Example 1.

The external quantum efficiency and the emission life of each of the obtained organic EL elements were expressed as relative values when each of those values of Organic EL Element OLED4-1 was set to 100. The obtained results were summarized in Table 4.

TABLE 4

| Element No. | Emission Host | Emission Dopant | Hole Blocking Material | External Quantum Efficiency | Emission Life | Remarks |
| --- | --- | --- | --- | --- | --- | --- |
| OLED4-1 | CBP | Ir-1 | BCP | 100 | 100 | Comp. |
| OLED4-2 | CBP | Ir-1 | 1 | 119 | 155 | Inv. |
| OLED4-3 | CBP | Ir-1 | 5 | 116 | 150 | Inv. |
| OLED4-4 | CBP | Ir-1 | 7 | 119 | 144 | Inv. |
| OLED4-5 | CBP | Ir-1 | 10 | 117 | 140 | Inv. |
| OLED4-6 | CBP | Ir-1 | 16 | 121 | 168 | Inv. |
| OLED4-7 | CBP | Ir-1 | 19 | 113 | 137 | Inv. |
| OLED4-8 | CBP | Ir-1 | 22 | 119 | 172 | Inv. |
| OLED4-9 | CBP | Ir-1 | 38 | 121 | 154 | Inv. |
| OLED4-10 | CBP | 1 | B1 | 125 | 195 | Inv. |
| OLED4-11 | CBP | 5 | B1 | 114 | 175 | Inv. |
| OLED4-12 | TCBP1 | 1 | B1 | 127 | 104 | Inv. |
| OLED4-13 | TCBP2 | 1 | B1 | 126 | 130 | Inv. |
| OLED4-14 | ACZ1 | 1 | B1 | 127 | 255 | Inv. |
| OLED4-15 | CBP | 1 | ACZ1 | 124 | 210 | Inv. |
| OLED4-16 | CBP | 5 | ACZ1 | 114 | 191 | Inv. |
| OLED4-17 | TCBP1 | 1 | ACZ1 | 126 | 215 | Inv. |
| OLED4-18 | TCBP2 | 1 | ACZ1 | 125 | 245 | Inv. |
| OLED4-19 | ACZ1 | 1 | ACZ1 | 125 | 277 | Inv. |

Inv.: Inventive, Comp.: Comparative

Table 4 revealed that each of the organic EL elements of the present invention attained a higher emission efficiencies and a longer emission life compared to those of the Comparative organic EL element. The inventive organic EL elements all emitted green light.

Further improved effect of the present invention (high luminance and elongation of emission life) was observed when one of the following compound was incorporated in the emission layer, namely, the compound represented by Formula (10) or (11), or the carboline derivative, one of carbon atoms of a hydrocarbon ring constituting the carboline ring of the carboline derivative being replaced with a nitrogen atom, and when one of the following compound was incorporated in the hole blocking layer, namely, the boron derivative, the carboline derivative, or the carboline derivative, one of carbon atoms of a hydrocarbon ring constituting the carboline ring of the carboline derivative being replaced with a nitrogen atom.

Example 5

<<Preparation of Full Color Display Device>>
(Preparation of Blue Light Emitting Element)
Organic EL Element OLED1-5 in Example 1 was used as a blue color emitting element.
(Preparation of Green Light Emitting Element)
Organic EL Element OLED2-7 in Example 2 was used as a green color emitting element.
(Preparation of Red Light Emitting Element)
Organic EL Element OLED3-8 in Example 3 was used as a red color emitting element.

The red, green blue light emitting organic EL elements prepared as above were juxtaposed on the same substrate, and an active matrix full color display device as shown in FIG. 1 was prepared. In FIG. 2, a schematic drawing of only display section A was shown. Namely, on the same substrate, a wiring section containing plural scanning lines 5 and plural data lines 6 and juxtaposed plural pixels 3 (pixels emitting red light, pixels emitting green light and pixels emitting blue light) are provided. The plural scanning lines 5 and plural data lines 6 of the wiring section are composed of an electroconductive material. The lines 5 and the lines 6 are crossing with each other at a right angle to form a lattice, and connected to the pixels 3 at the crossed points (not illustrated). Each of the plural pixels 3 are driven by an active matrix method in which each pixel contains an organic EL element emitting a corresponding color light and active elements including a switching transistor and a driving transistor. When scanning signals are applied through the scanning lines 5, image data signals are received through data lines 6, and emission occurs according to the received image data. By juxtaposing red light emitting pixels, green light emitting pixels, and blue light emitting pixels side by side on the same substrate, a full color display device was prepared.

By driving the full color display device, it was confirmed that a full color moving picture with high luminance, a long life and a clear full color image was obtained.

Example 6

<<Preparation of White Light Emitting Element and White Light Emitting Illumination Device>>

A 20 mm×20 mm pattern of the transparent electrode was formed on the substrate having a transparent electrode of Example 1, and a 25 nm thickness of α-NPD was formed as a hole injection/transport layer on the electrode in the same manner as Example 1. In three above-mentioned resistive heating boats, CBP, Compound 6 of the present invention and Ir-9 were placed one by one, and independently heated by supplying an electric current to each boat so that the ratio of the deposition rate of (CBP, an emission host):(Compound 6, an emission dopant):(Ir-9) was controlled to be 100:5:0.6. Thus an emission layer with the thickness of 30 nm was formed.

Subsequently, a 10 nm thickness of BCP layer was formed as a hole blocking layer and a 40 nm thickness of $Alq_3$ layer was formed as an electron transport layer.

Next, in the same manner as Example 1, a stainless-steel mask having a square hole of the same size as the transparent electrode was placed on the electron injection layer, and a 0.5 nm thickness of lithium fluoride as a cathode buffer layer and a 150 nm thickness of aluminum as a cathode were formed via a vacuum deposition method.

Thus obtained organic EL element was sealed in a container in the same manner and using the same materials as Example 1 to obtain a flat panel lamp. In FIG. 6, a schematic illustration of the flat panel lamp is shown. FIG. 6(*a*) represents a top view and FIG. 6(*b*) represents a cross-section of the flat panel lamp. In FIGS. 6(*a*) and 6 (*b*), 101 represents a glass substrate having a transparent electrode, 102 represents an organic EL layer containing above-mentioned hole injection/transport layer, emission layer, hole blocking layer and electron transport layer, and 103 represents a cathode, 104 represents a glass sealing container, 105 represents a dehydrating agent: barium oxide, and 107 represents a UV-curable resin adhesive.

By applying a current to the flat panel lamp, emission of substantially white light was observed, indicating that the flat panel lamp is usable as an illumination device.

Possibility for Industrial Use

The present invention enables to provide an organic EL element material represented by a platinum complex having a ligand which contains an aryl group of which free rotation is blocked or an aromatic heterocycle group of which free rotation is blocked, and to provide an organic EL element, an illuminating device and a display device exhibiting a high emission efficiency and a long emission life, which can be prepared by using the organic EL element material of the present invention.

What is claimed is:

1. An organic electroluminescence element material comprising a platinum complex having a platinum ion and a ligand comprising an aryl group of which free rotation is blocked or an aromatic heterocycle group of which free rotation is blocked, wherein the platinum complex is an ortho-metallated complex, wherein the ortho-metallated complex is selected from the group consisting of
a platinum complex represented by Formula (7) or a tautomer of a compound represented by Formula (7); and
a platinum complex represented by Formula (8) or a tautomer of a compound represented by Formula (8):

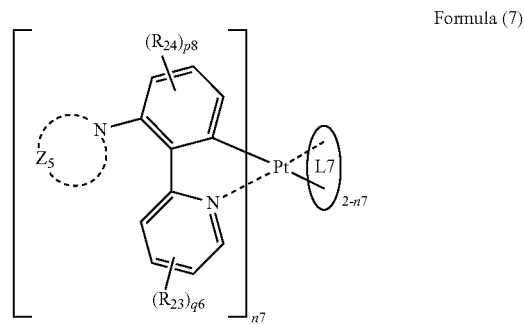

Formula (7)

wherein $R_{23}$ and $R_{24}$ each represent a hydrogen atom or a substituent selected from following Group A; $Z_5$ represents a group of atoms necessary to form an aromatic heterocycle containing a nitrogen atom; n7 represents an integer of 1 or 2, provided that, when n7 is 1, L7 represents a bidentate ligand; p8 represents an integer of 0-3; and q6 represents an integer of 0-4,

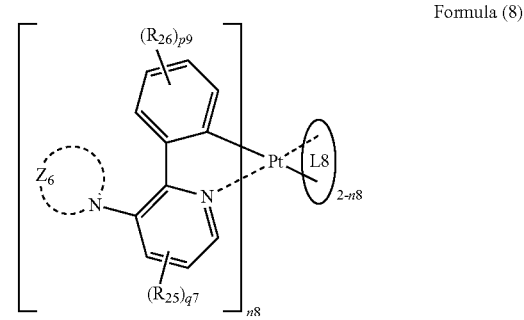

Formula (8)

wherein $R_{25}$ and $R_{26}$ each represent a hydrogen atom or a substituent selected from following Group A; $Z_6$ represents a group of atoms necessary to form an aromatic heterocycle containing a nitrogen atom; n8 represents an integer of 1 or 2, provided that, when n8 is 1, L8 represents a bidentate ligand; p9represents an integer of 0-3; and q7 represents an integer of 0-4, Group A:
an alkyl group, a trifluoromethyl group, an aryl group and an aromatic heterocycle group, wherein these groups may further be substituted.

2. An organic electroluminescence element comprising the organic electroluminescence element material of claim 1.

3. The organic electroluminescence element comprising an emission layer and a hole blocking layer as constituting layers,
    wherein the emission layer and the hole blocking layer each comprise the organic electroluminescence element material of claim 1; and
    the hole blocking layer further comprises a carboline or a carboline of which one of carbon atoms of a hydrocarbon ring constituting a carboline ring of the carboline is replaced with a nitrogen atom.

4. The organic electroluminescence element comprising an emission layer and a hole blocking layer as constituting layers,
    wherein the emission layer and the hole blocking layer each comprise the organic electroluminescence element material of claim 1; and
    the hole blocking layer further comprises a boron derivative.

5. A display device comprising the organic electroluminescence element of claim 1.

6. An illumination device comprising the organic electroluminescence element of claim 1.

7. The organic electroluminescence element material of claim 1, wherein the ortho-metallated complex is a platinum complex represented by Formula (7) or a tautomer of a compound represented by Formula (7).

8. The organic electroluminescence element material of claim 1, wherein the ortho-metallated complex is a platinum complex represented by Formula (8) or a tautomer of a compound represented by Formula (8).

9. An organic electroluminescence element comprising an emission layer as a constituting layer, wherein the emission layer comprises the organic electroluminescence element material of claim 1.

10. The organic electroluminescence element of claim 9, wherein the emission layer comprises a compound represented by Formula (10):

Formula (10)

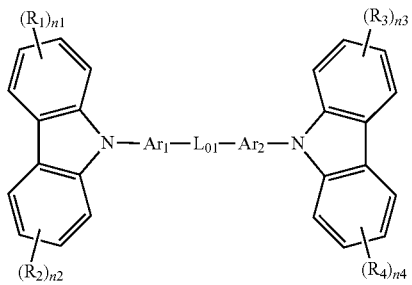

wherein $R_1$, $R_2$, $R_3$ and $R_4$ each represent a hydrogen atom or a substituent; n1, n2, n3, and n4 each represent an integer of 0-4; and $Ar_1$ and $Ar_2$ each represent an arylene group or a divalent aromatic heterocycle group; and $L_{01}$ represents a divalent linking group.

11. The organic electroluminescence element of claim 9, wherein the emission layer comprises a compound represented by Formula (11):

Formula (11)

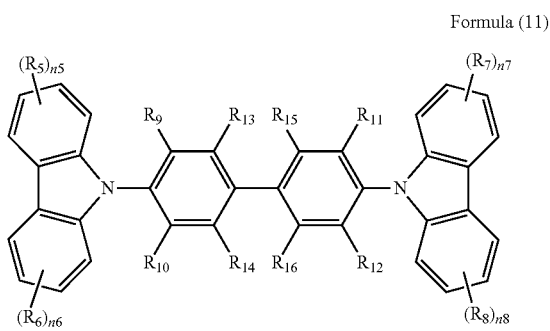

wherein $R_5$-$R_{16}$ each represent a hydrogen atom or a substituent, provided that one of $R_{13}$ -$R_{16}$ represents a substituent; and n5-n8 each represent an integer of 0-4.

12. The organic electroluminescence element of claim 9, wherein the emission layer comprises a carboline or a carboline of which one of carbon atoms of a hydrocarbon ring constituting a carboline ring of the carboline is replaced with a nitrogen atom.

13. The organic electroluminescence element of claim 9 further comprising a hole blocking layer as a constituting layer, wherein the hole blocking layer comprises a carboline or a carboline of which one of carbon atoms of a hydrocarbon ring constituting a carboline ring of the carboline is replaced with a nitrogen atom.

14. The organic electroluminescence element of claim 9 further comprising a hole blocking layer as a constituting layer, wherein the hole blocking layer comprises a boron derivative.

* * * * *